United States Patent
Li et al.

(10) Patent No.: US 9,598,695 B2
(45) Date of Patent: *Mar. 21, 2017

(54) MODULATION OF T CELL SIGNALING THRESHOLD AND T CELL SENSITIVITY TO ANTIGENS

(71) Applicant: The Board of Trustees of the Leland Stanford Junior University, Stanford, CA (US)

(72) Inventors: Qi-Jing Li, Mountain View, CA (US); Chang-Zheng Chen, Stanford, CA (US); Mark M. Davis, Atherton, CA (US); Jacqueline Chau, San Jose, CA (US)

(73) Assignee: The Board of Trustees of the Leland Stanford Junior University, Standford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/165,762

(22) Filed: May 26, 2016

(65) Prior Publication Data

US 2016/0281087 A1    Sep. 29, 2016

Related U.S. Application Data

(60) Division of application No. 14/288,214, filed on May 27, 2014, now Pat. No. 9,364,522, which is a division of application No. 12/792,585, filed on Jun. 2, 2010, now Pat. No. 8,741,860, which is a continuation of application No. 11/977,506, filed on Oct. 24, 2007, now Pat. No. 7,803,784.

(60) Provisional application No. 60/901,177, filed on Feb. 12, 2007, provisional application No. 60/873,764, filed on Dec. 8, 2006, provisional application No. 60/854,407, filed on Oct. 24, 2006.

(51) Int. Cl.
| | |
|---|---|
| A61K 48/00 | (2006.01) |
| C07H 21/02 | (2006.01) |
| C07H 21/04 | (2006.01) |
| C12N 15/113 | (2010.01) |
| G01N 33/50 | (2006.01) |
| A61K 39/00 | (2006.01) |

(52) U.S. Cl.
CPC ............ *C12N 15/113* (2013.01); *A61K 39/00* (2013.01); *G01N 33/505* (2013.01); *G01N 33/5041* (2013.01); *A61K 2039/57* (2013.01); *C12N 2310/11* (2013.01); *C12N 2310/113* (2013.01); *C12N 2310/141* (2013.01); *C12N 2310/315* (2013.01); *C12N 2310/321* (2013.01); *C12N 2310/3515* (2013.01); *G01N 2500/02* (2013.01); *G01N 2800/24* (2013.01)

(58) Field of Classification Search
CPC ............................ A61K 48/00; C12N 15/113
See application file for complete search history.

(56) References Cited

U.S. PATENT DOCUMENTS

| | | |
|---|---|---|
| 7,803,784 B2 | 9/2010 | Li et al. |
| 2005/0256072 A1 | 11/2005 | Aronin et al. |
| 2005/0260648 A1 | 11/2005 | Huffel et al. |
| 2005/0261218 A1 | 11/2005 | Esau et al. |
| 2006/0019286 A1 | 1/2006 | Horvitz et al. |
| 2006/0057595 A1 | 3/2006 | Lao et al. |
| 2006/0099619 A1 | 5/2006 | Remacle et al. |
| 2006/0105360 A1 | 5/2006 | Croce et al. |
| 2006/0134639 A1 | 6/2006 | Huffel et al. |
| 2006/0185027 A1 | 8/2006 | Bartel et al. |
| 2008/0176766 A1 | 7/2008 | Brown et al. |

FOREIGN PATENT DOCUMENTS

WO    WO2005/118806 A2    12/2005

OTHER PUBLICATIONS

Chen et al., "MicroRNAs modulate hematopoietic lineage differentiation," Science, Jan. 2, 2004, pp. 83-86, 303 (5654), AAAS, Washington, DC.
Krützfeldt et al., "Silencing of microRNAs in vivo with 'antagomirs'," Nature, Dec. 1, 2005, pp. 685-689, 438(7068), Nature Publishing Group, London, United Kingdom.
Davis et al., "Improved targeting of miRNA with antisense oligonucleotides", Nucleic Acids Research, 2006, pp. 2294-2304, 34(8), Oxford University Press, Oxford, United Kingdom.
Ramkissoon et al., "Hematopoietic-specific microRNA expression in human cells", Leukemia Research, 2006, pp. 643-647, 30, Elsevier, Amsterdam, Netherlands.
"International Search Report and Written Opinion of the International Searching Authority", PCT International Searching Authority, Sep. 3, 2008, Int'l App. No. PCT/US07/22601, 11 pages.

(Continued)

*Primary Examiner* — Amy Bowman
(74) *Attorney, Agent, or Firm* — Pamela J. Sherwood; Bozicevic, Field & Francis LLP

(57) ABSTRACT

MicroRNAs (miRNAs) are a diverse and abundant class of ~22-nucleotide (nt) endogenous regulatory RNAs that play a variety of roles in animal cells by controlling gene expression at the posttranscriptional level. Increased miR-181a expression in mature T cells is shown to cause a marked increase in T cell activation and augments T cell sensitivity to peptide antigens. Moreover, T cell blasts with higher miR-181a expression become reactive to antagonists. The effects of miR-181a on antigen discrimination are in part achieved by dampening the expression of multiple negative regulators in the T cell receptor (TCR) signaling pathway, including PTPN22 and the dual specificity phosphatases DUSP5 and DUSP6. This results in a reduction in the TCR signaling threshold, thus quantitatively and qualitatively enhancing T cell sensitDynaivity to antigens.

8 Claims, 35 Drawing Sheets

(56) References Cited

OTHER PUBLICATIONS

Mieister et al., "Sequence-specific inhibition of microRNA- and siRNA-induced RNA silencing", RNA. Mar. 2004 pp. 544-550, 10(3),Cold Spring Harbor Laboratory Press, Cold Spring Harbor, NY.
Zhou et al., "Effects of microRNA miR-181a on gene expression profiles of K562 cells", May 2006, pp. 606-609, 26(5).
Guimaraes-Sternberg et al. "MicroRNA modulation of megakaryoblast fate involves cholinergic signaling", Leuk Res., May 2006, pp. 583-595, 30(5), Elsevier, Amsterdam, Netherlands.
Laufer, "T-cell sensitivity: a microRNA regulates the sensitivity of the T-cell receptor", Immunol Cell Biol., Jul. 2007, pp. 346-347, 85(5), Nature Publishing Group, London, United Kingdom.
Neilson et al., "Dynamic regulation of miRNA expression in ordered stages of cellular development", Genes Dev. Mar. 2007, pp. 578-589, 21(5), Cold Spring Harbor Laboratory Press, Huntington, New York.
Li et al. "miR-181a is an intrinsic modulator of T cell sensitivity and selection", Cell, Apr. 6, 2007, pp. 147-161,129 (1), Elsevier, Amsterdam, Netherlands.
Li et al., "MiR-181a reduces the T cell receptor signaling threshold and enhances sensitivity to antigens", Molecular Biology of the Cell; 46th annual meeting of the American Society for Cell Biology, 2006, vol. 17, No. suppl S. Abstract.
Mahato et al., "Modulation of gene expression by antisense and antigene oligodeoxynucleotides and small Interfering RNA", Expert Opin. Drug Deilv., 2005, pp. 3-28, vol. 2, No. 1.
Scherer et al., "Approaches for the sequence-specific knockdown of mRNA", Nature Biotechnology, Nov. 26, 2003, pp. 1457-1465, vol. 21, No. 12.

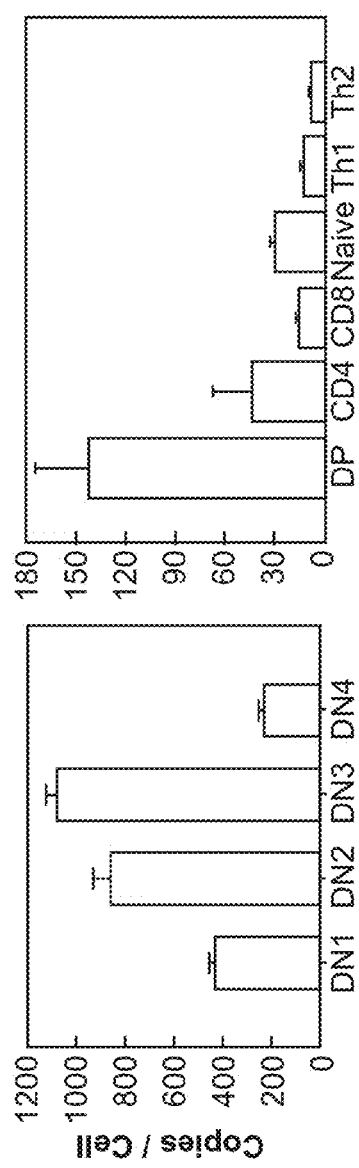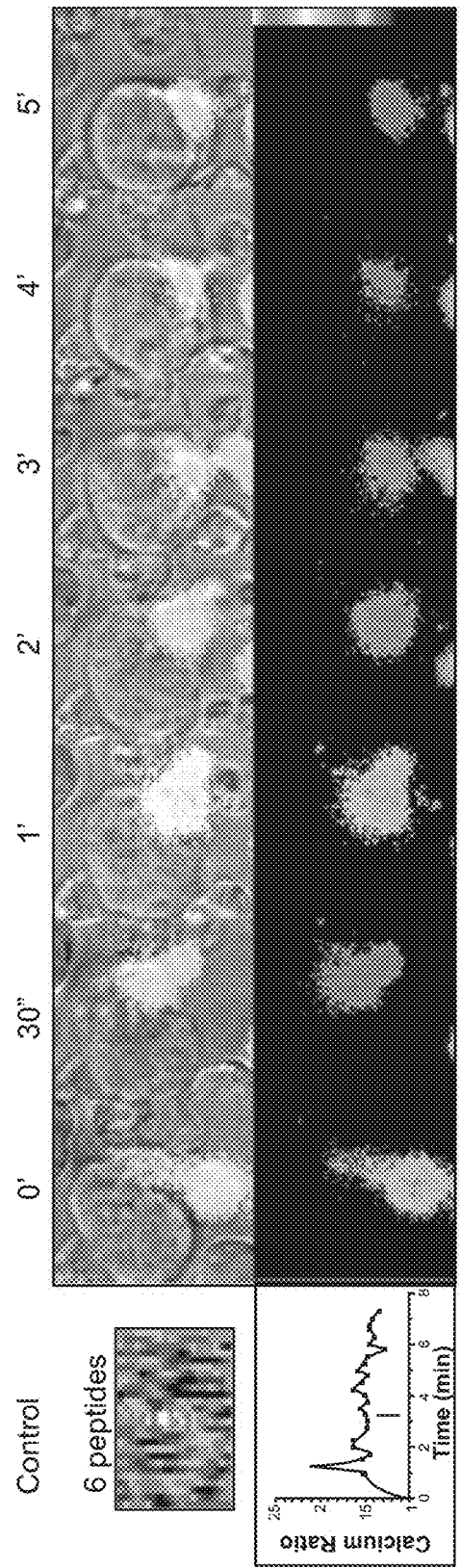
FIG. 1A
FIG. 1B
FIG. 1C

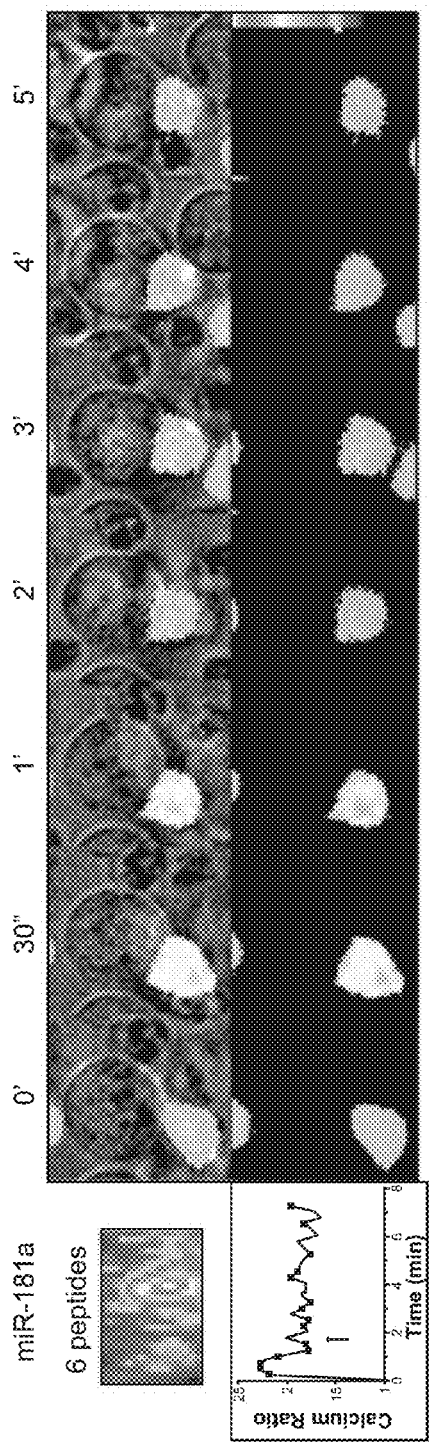
FIG. 1D
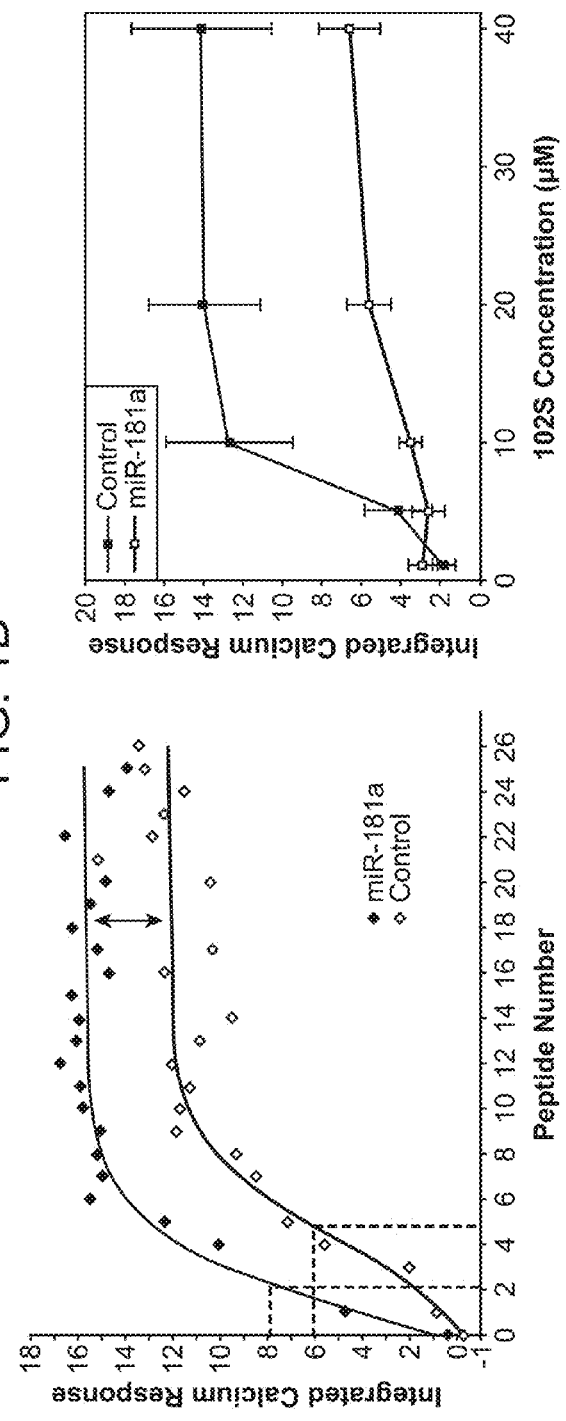
FIG. 1E
FIG. 1F

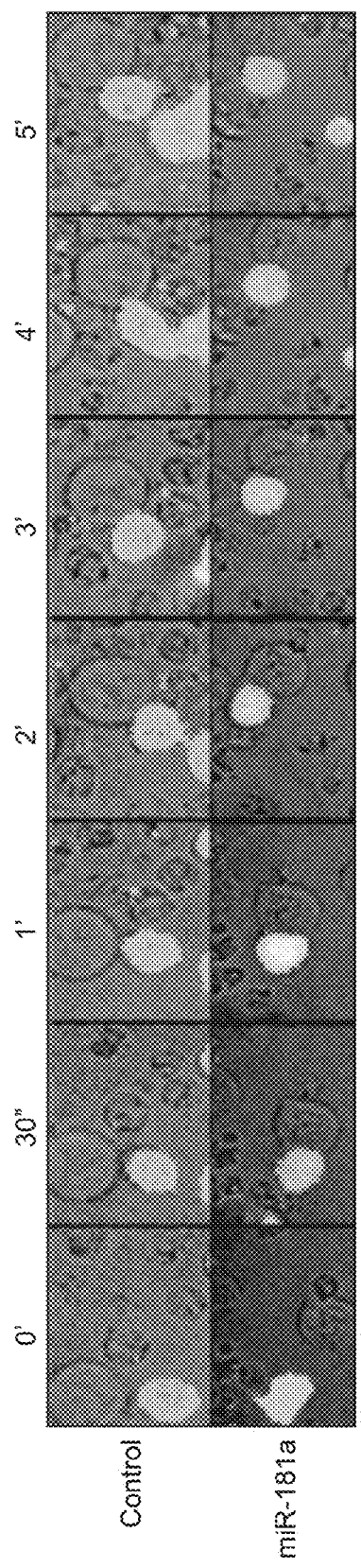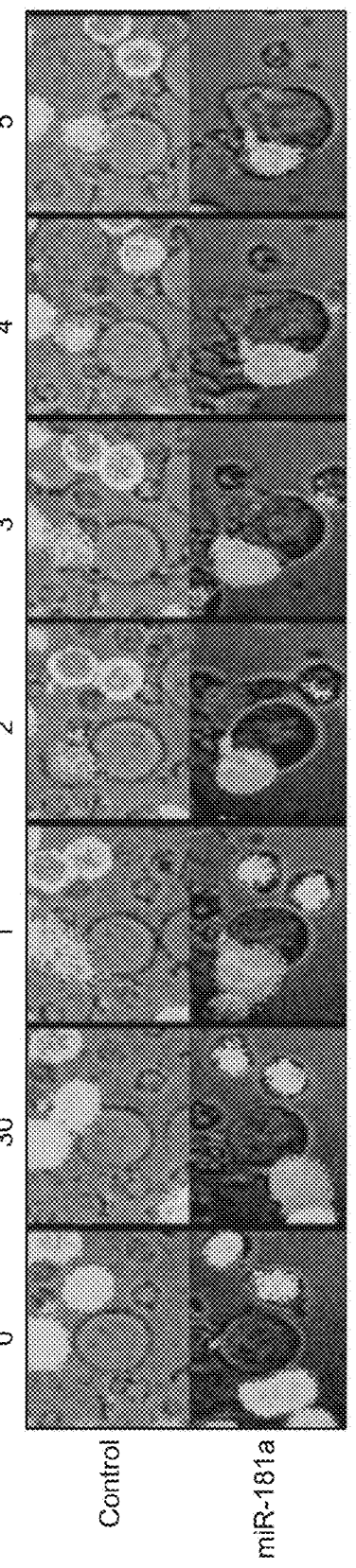

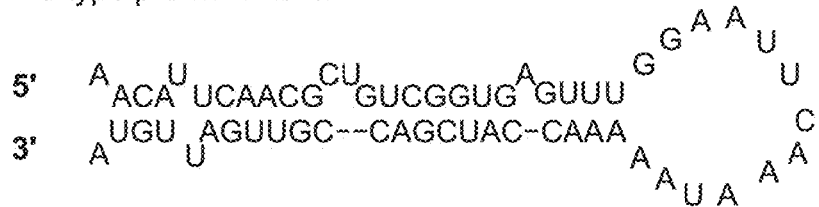
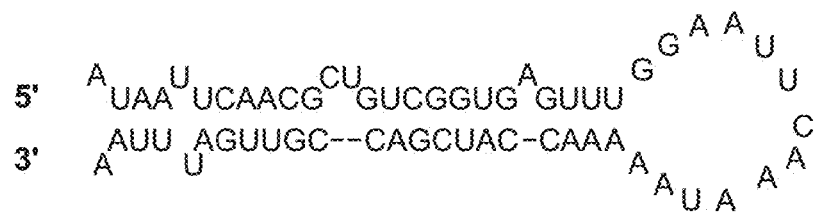
FIG. 12A
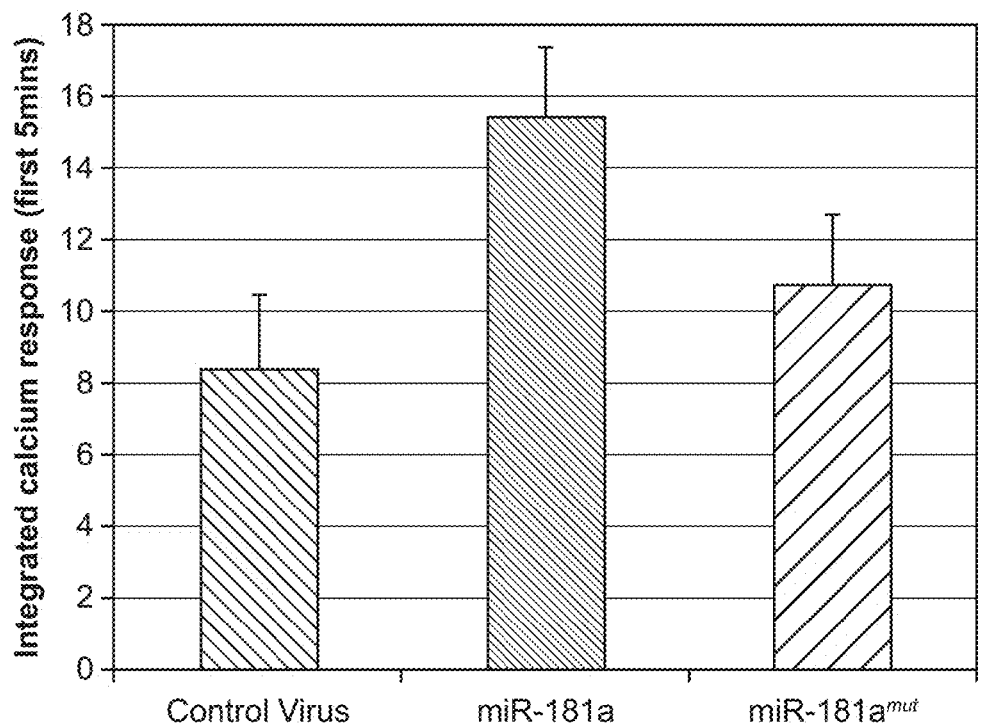
FIG. 12B

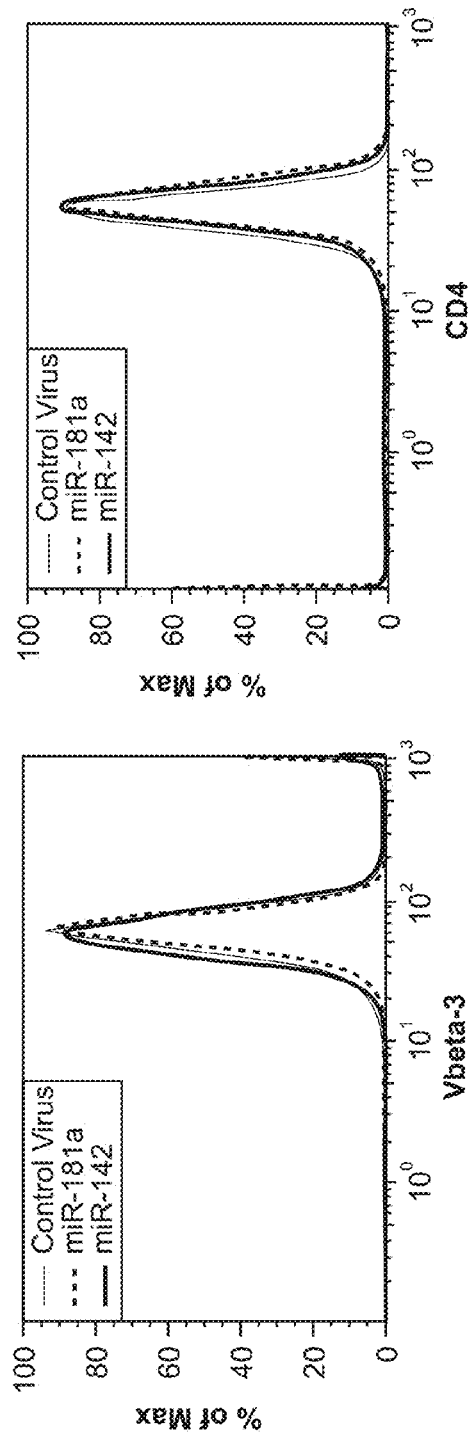
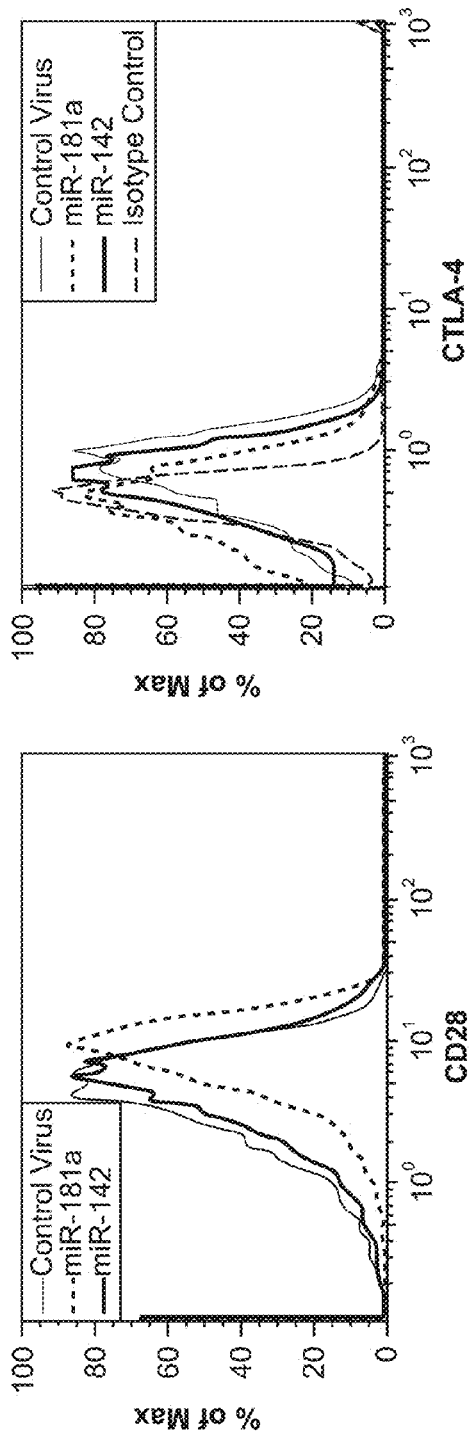
FIG. 13A
FIG. 13B

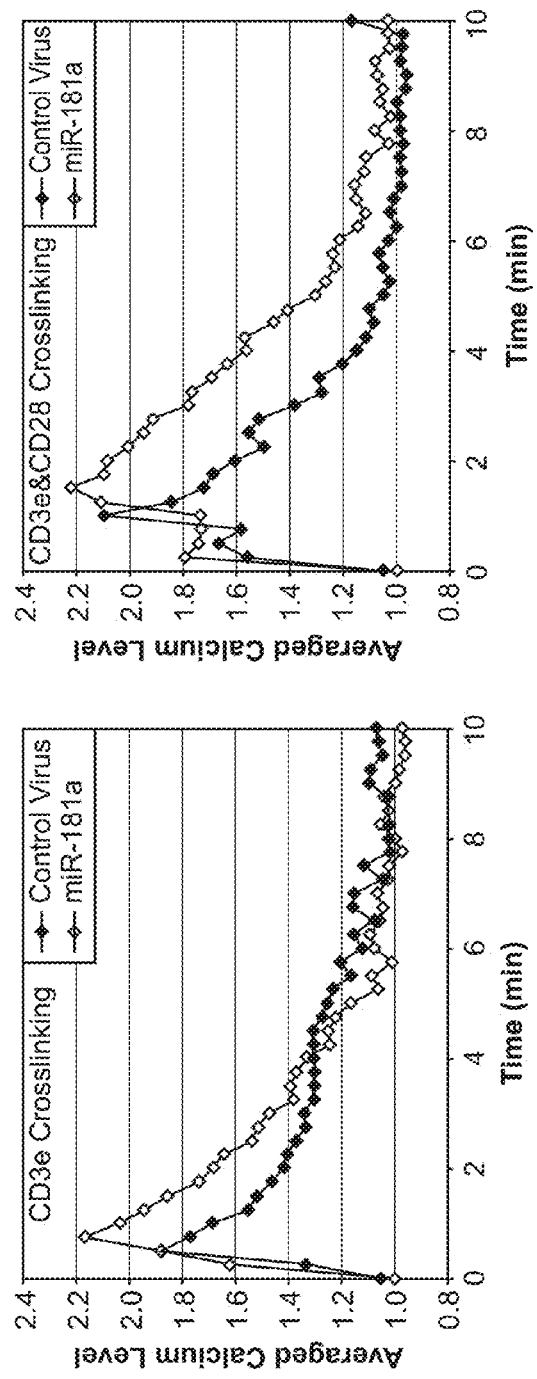
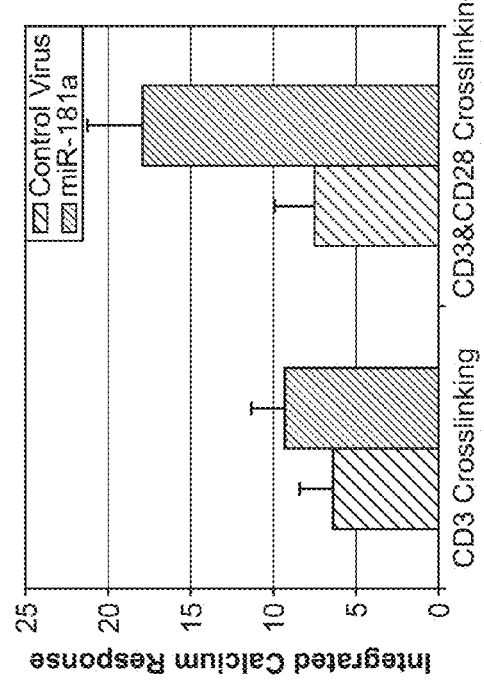
FIG. 13C
FIG. 13D

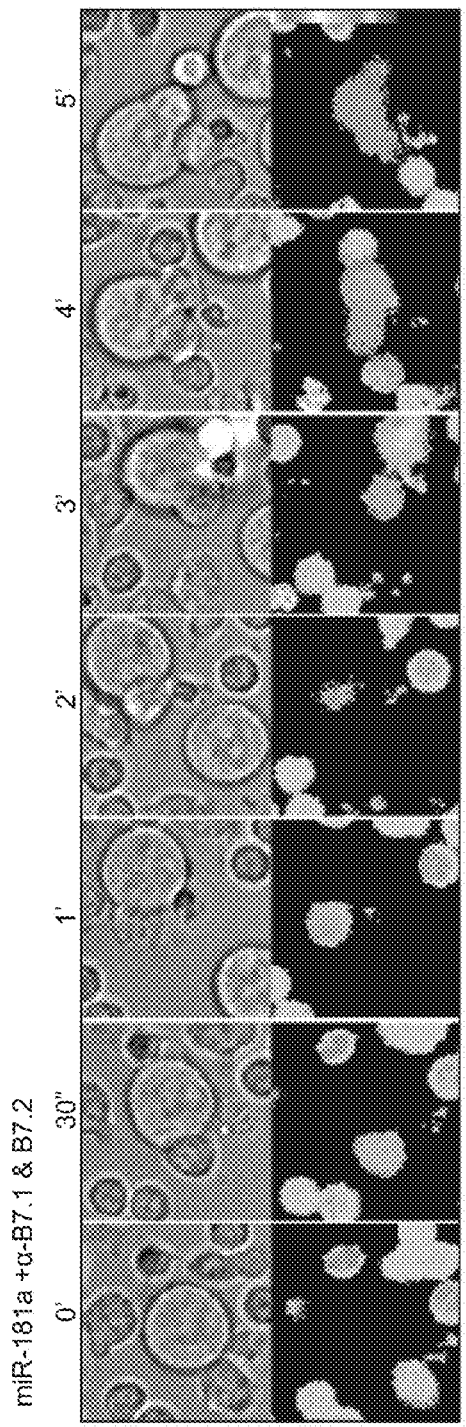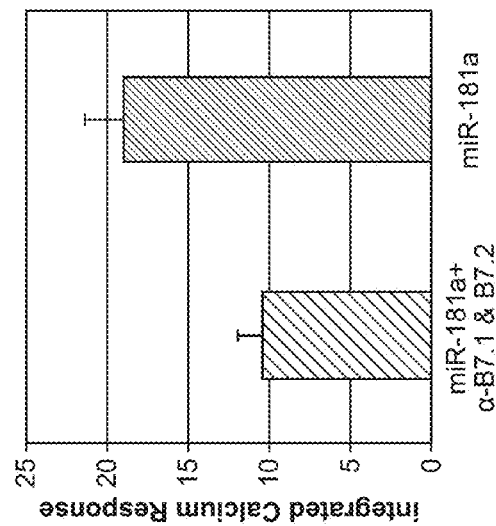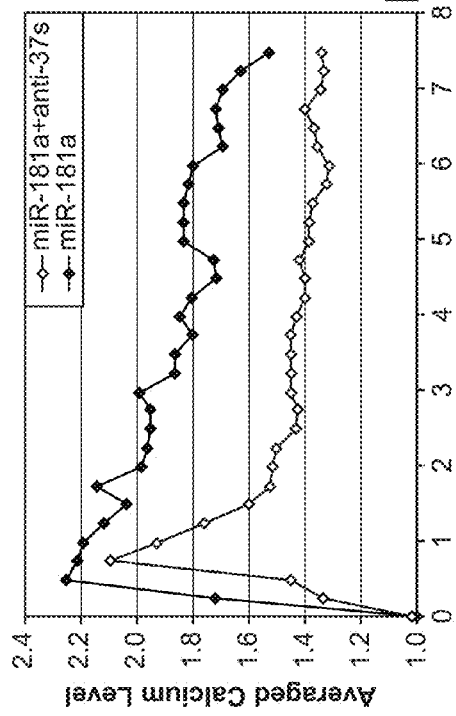

MODULATION OF T CELL SIGNALING THRESHOLD AND T CELL SENSITIVITY TO ANTIGENS

GOVERNMENT SUPPORT

This invention was made with Government support under contracts HL081612 and AI022511 awarded by the National Institutes of Health. The Government has certain rights in the invention.

BACKGROUND OF THE INVENTION

One of the key features of a functioning immune system is its ability to distinguish antigens of foreign origin from those derived endogenously and to mount an immune response against the former. With respect to T cells, this goal is achieved through antigen recognition by T cell receptors (TCRs) and a highly ordered developmental process in the thymus and in secondary lymphoid organs. TCRs constantly sample diverse self- or foreign-peptide antigens presented in major histocompatibility complexes (MHCs) on the surface of antigen presenting cells (APCs) and elicit discrete intracellular signals and T cell responses. The mature T cell's response to antigens is largely dictated by the binding characteristics of its TCR for a given peptide-MHC complex. In general, peptide-MHC (pMHC) ligands with slower dissociation rates produce stronger TCR signals and lead to higher T cell reactivity to the antigenic peptides.

Variations in the antigenic peptide affinities to TCRs may lead to both quantitative and qualitative changes in its ability to activate TCR signaling pathways and T cell responses. Typically, the most stable pMHC complexes with respect to TCR binding are agonists, while the less stable variants are weak agonists and then antagonists, which are not able to activate T cells more than partially themselves and also block the response to agonist ligand. Although a number of models have been proposed to explain the kinetic discrimination in T cell activation, exactly how T cells sense quantitative changes in antigenic peptide affinities through their TCRs and produce both quantitatively and qualitatively different responses remains an intensive area of study.

In addition, T cell responsiveness and TCR signaling to a specific ligand also vary with different developmental stages, suggesting that T cell sensitivity to antigens might be intrinsically regulated during development. For example, in immature CD4+CD8+ double positive thymocytes, low affinity antigenic peptides that are unable to activate mature effector T cells are sufficient to induce strong activation and clonal deletion; antagonists that are normally inhibitory to effector T cells can induce positive selection. These observations demonstrate that T cell sensitivity is intrinsically regulated to ensure the proper development of specificity and sensitivity to foreign antigens while avoiding self-recognition. However, little is known about how intrinsic molecular programs are regulated, and how they influence T cell sensitivity toward antigens.

Methods of regulating T cell signaling thresholds and sensitivity to antigens is of great interest for clinical and research purposes. The present invention provides a means to regulate these functions.

Publications: MicroRNAs (miRNAs) are an abundant class of non-coding RNAs that are believed to be important in many biological processes through regulation of gene expression. These ~22-nt RNAs can repress the expression of protein-coding genes by targeting cognate messenger RNAs for degradation or translational repression. The mechanisms by which miRNAs exert these effects are unclear, as is whether they have any specific role in the adaptive immune response.

Chen et al. (2004) Science 303:83 describe the modulation of hematopoietic lineage differentiation by microRNAs. Krutzfeldt et al. (2005) Nature 438:685 describe the silencing of microRNAs in vivo with antagomirs.

The miR-181a RNA is represented in published US Patent Applications: 20060185027, Systems and methods for identifying miRNA targets and for altering miRNA and target expression; 20060134639, Method for the determination of cellular transcriptional regulation; 20060105360, Diagnosis and treatment of cancers with microRNA located in or near cancer associated chromosomal features; 20060099619, Detection and quantification of miRNA on microarrays; 20060057595, Compositions, methods, and kits for identifying and quantitating small RNA molecules; 20060019286, High throughput methods relating to microRNA expression analysis; 20050261218, Oligomeric compounds and compositions for use in modulation small non-coding RNAs; 20050260648, Method for the determination of cellular transcriptional; 20050256072, Dual functional oligonucleotides for use in repressing mutant gene expression.

SUMMARY OF THE INVENTION

Methods and compositions are provided for regulating T cell signaling threshold and T cell sensitivity to antigen by modulating expression of a microRNA rheostat. Target cells and tissues of interest for modulation include bone marrow, e.g. stem cells, lymphocyte progenitor cells, etc.; thymocytes; peripheral blood, e.g. T helper cells, cytotoxic T cells, memory T cells, regulatory T cells, and the like. By altering the signaling threshold with respect to an antigen of interest, the T cell mediated immune response can be tailored to provide for increased responsiveness, e.g. against antigens associated with tumors, chronic infections, etc.; or to provide for decreased responsiveness, e.g. against allergens, autoantigens, transplantation antigens, etc.

In one embodiment of the invention, miR-181a and the targets of miR-181a as described herein are used in the screening of candidate agents for activity in regulation of T cell signaling threshold and T cell sensitivity to antigen. Embodiments of interest include screening for agents that act on at least two or more of the pathways regulated by miR-181a.

In other embodiments, the genetic sequence encoding miR-181a, and/or the expression levels of miR-181a are determined in connection with diagnostic applications, where alterations in the sequence or level of expression are correlated with aberrations in the regulation of T cell signaling threshold and T cell sensitivity to antigen.

It is shown herein that increasing expression of the microRNA miR-181a in T cells quantitatively augments the output of T cell receptor signaling, as indicated, inter alia, by the elevation of intracellular calcium, cytokine production, and cell proliferation. Accompanying the increase in T cell sensitivity to antigen, these cells can also become reactive to peptide antigens that are otherwise incapable of activating T cells, and which may otherwise block T cell activation. The change in reactivity to peptide antigens is attributable in part to selective down-regulation of multiple negative regulatory proteins, including the ERK specific dual specificity phosphatases DUSP5 and DUSP6. In some embodiments of the invention, the T cell signaling threshold and T cell sensitivity to antigen is achieved by modulation of DUSP5 and/or DUSP6 activity.

Increasing miR-181a expression in T cell blasts results in decreased phosphatase levels, which leads to an increase in the amount of activated Lck and ERK kinases without antigenic stimulation and a reduction in the threshold required for T cell activation. In addition, the surface densities of costimulatory molecules CD28 and CTLA-4 are changed. These results demonstrate that miR-181a controls multiple pathways that regulate the sensitivity of T cells to antigen. By reducing negative feedback mechanisms and potentiating positive ones, T cells are manipulated to exhibit quantitatively and qualitatively different responses to antigen stimulation.

These and other embodiments of the invention will be apparent from the description that follows. The compositions, methods, and techniques described in this disclosure hold considerable promise for use in diagnostic, drug screening, and therapeutic applications.

BRIEF DESCRIPTION OF THE FIGURES

FIG. 1A-1F Effects of miR-181a on agonist stimulated T cell calcium response. (A) Developmental regulation of miR-181a expression in various purified T cell populations determined by RT-PCR. (B) qPCR analysis of miR-181a ectopic expression in effector T cell blasts. (C & D), Calcium flux in T cells ectopically expressing control virus (C) or miR-181a virus (D) in response to defined number of agonist MCC peptide. Top left, the peptide images representing the integrated intensity of 6 MCC peptides at the T cell and APC (T:APC) interface. Bottom left, relative cytosolic calcium concentration as a function of time after stimulation, as measured from ratioed fura-2 images; the arrow indicates the time point at which the peptide image (shown in top left) was taken. Top right, overlaid differential interference contrast (DIC) images and ratioed calcium images taken at different time points after stimulation. Bottom right, corresponding ratioed calcium images. Fluorescence intensity of calcium signal is represented in a false color scale. (E) Integrated calcium signals as a function of defined number of MCC ligands. Ratioed calcium images were measured every 15 seconds in responding T cells and integrated for 5 minutes from the time of initial calcium increase. Each data point represents the average calcium signals of three or more responding T cells. Lines are fitted with the same sigmoidal dose-response (variable slope) equation. The dashed lines indicate the number of peptides required to reach half maximal calcium responses. The double arrow illustrates the absolute increase of calcium signal plateau. (F) Effects of miR-181a on T cell calcium responses to APCs preloaded with various concentrations of the weak agonist MCC 102S (averaged integrated calcium value ±SD, n=30). All calcium response curves (C-F) are color-coded for control (blue) or miR-181a (red) T cell blasts.

FIG. 2A-2F Effects of miR-181a on antagonist function. (A & B) Overlaid DIC and calcium ratio images taken at various time points after the control (top panel) or the miR-181a T cell blasts (lower panel) were stimulated with APCs preloaded with (A) mixed agonist MCC (0.1 μM) and antagonist MCC 99R (20 μM) or (B) antagonist MCC 99R (20 μM) alone. (C) Average calcium level was plotted against time. Each data point represents the average calcium level of 30 or more responding T cells in each of the experimental groups. Time zero was designated as the image stack before the first 20% calcium increase for the miR-181a T cell blasts or the frame of initial T:APC contact in the DIC channel for non-responding T cells. (D) Induction of IL-2 production by antagonist MCC 99R. Virally-infected and selected T cell blasts were set to rest by day10 after preparation, then co-cultured with γ-irradiated CH27 cells preloaded with either the null peptide MCC 99A (10 μM), the antagonist MCC 99R (10 μM), or the agonist MCC (1 μM). Supernatants were collected at 24 hours after stimulation and analyzed for IL-2 production by ELISA ([Il-2] ±SD, n=3). (E) Induction of T cell proliferation by the antagonist MCC 99R. Virally-infected and selected T cell blasts were stained with the fluorescent dye CFSE and co-cultured with γ-irradiated CH27 cells preloaded with null peptide MCC 99A (10 μM), antagonist MCC 99R (10 μM), or agonist MCC (1 μM) on day12 after preparation. T cells were harvested and analyzed by FACS 24 hours after co-culture. Percentage of T cells undergoing proliferation was calculated as described (Gudmundsdottir et al., 1999). Representative experiments of three independent analyses are shown. (F) Effects of miR-181a on T cell calcium responses to the antagonist 102G. Virally-infected T cell blasts were stimulated with APCs preloaded with various concentrations of the antagonists MCC 99R and 102G (fura ratio ±SD, n=30).

for 5 mins. SHP-1 was co-precipitated with Lck whereas SHP-2 was undetectable under the same condition.

Figure 5A:
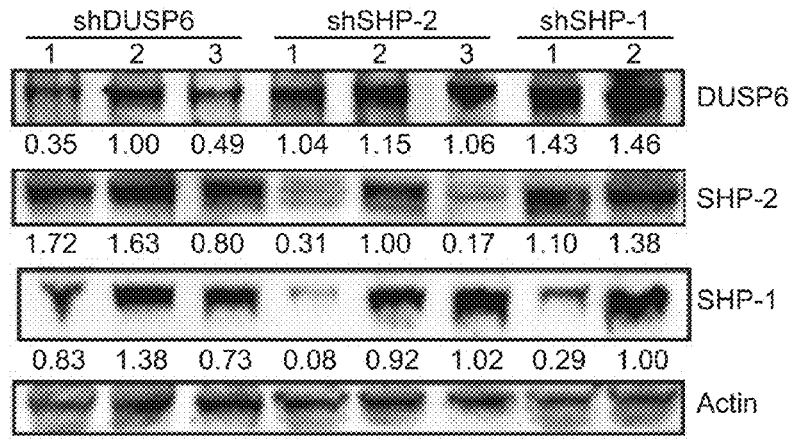
Figure 5B:
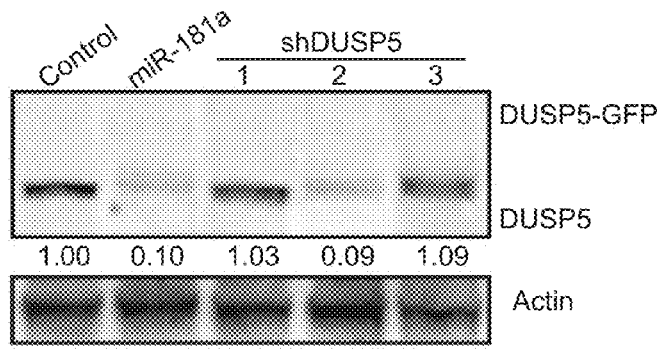
Figure 5C:
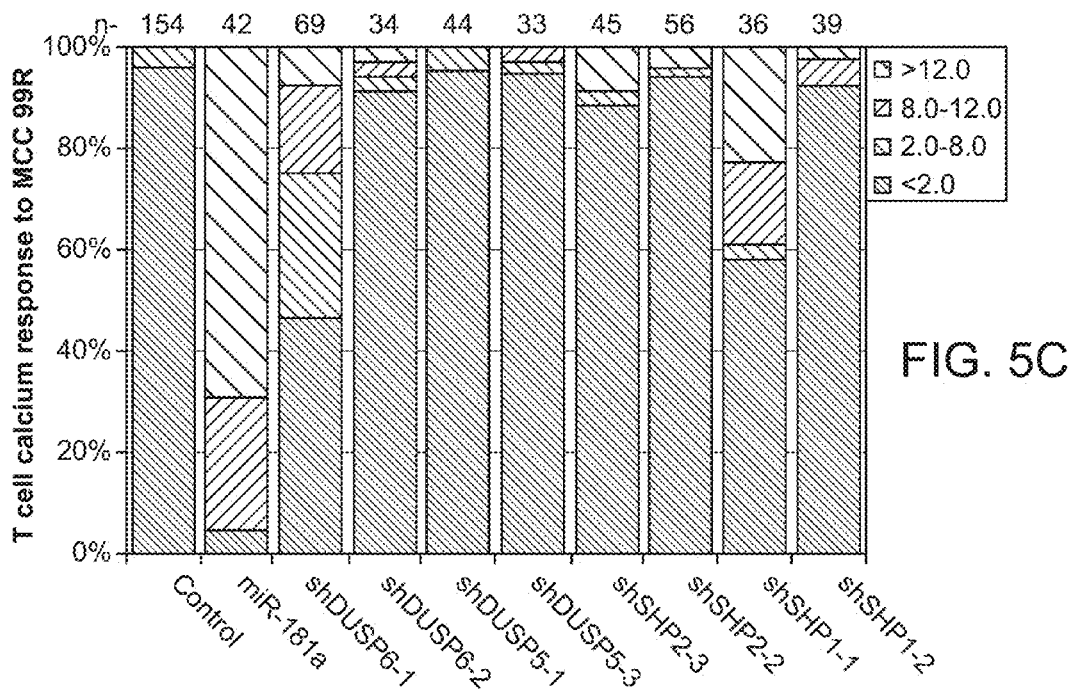

FIGS. 5A-5C shRNAs against individual miR-181a targets cannot fully recapitulate miR-181a function. (A&B) The efficacy and specificity of shRNA constructs that were designed to target DUSP6, SHP-2, SHP-1, and DUSP5, respectively, as determined by Western-blot analyses. (C) Calcium responses to antagonist MCC 99R stimulation in T cell ectopically expressing miR-181a or shRNAs against individual miR-181a targets, DUSP6, DUSP5, SHP-2, or SHP-1, respectively. Both the strength of calcium response and percentage of T cells activated were measured and summarized. Integrated calcium flux during the first 5 minutes after activation was used to evaluate the strength of TCR signaling. T cells with continuous calcium elevation at 50% above the baseline (designated as 1) for one minute were designated as activated T cells. Integrated calcium ratio was arbitrarily categorized using the response of the control T cell blasts to the agonist MCC as a reference and shown in color codes (<2, no response; 2-8.0, weak response; 8.0-12.0, medium response; >12.0, strong response).

FIGS. 6A-6E Restoring individual targets abrogates miR-181a effects on T cell sensitivity. (A) Western blot analysis shows restored DUSP6 expression. Abolishing T cell reactivity to the antagonist MCC 99R by restoring DUSP6 expression in miR-181a T cell blasts. (B) Restoring DUSP6 expression is sufficient to override the effects of miR-181a on the basal level and the post-stimulation kinetics of ERK phosphorylation. The gray line marks the basal level of ERK activation in control cells and the brown line indicates the full activation level of ERK in control T cells upon TCR activation. (C) Overlaid DIC and calcium ratio images taken at various time points after T cells ectopically expressing miR-181a alone (top panel) or miR-181a and DUSP6 together (lower panel) were stimulated with APCs preloaded with antagonist MCC 99R (20 μM). (D) Cytosolic calcium concentration as a function of time in T cells ectopically expressing control virus (grey), miR-181a alone (red), miR-181a and DUSP6 (dark blue line), miR-181a and wild type DUSP5 (green line), miR-181a and NLS mutated DUSP5 (light blue), and miR-181a and SHP-2 (purple). (E) Effects of individual target restoration on IL-2 production. Virally infected and selected T cell blasts were set to rest by day 12 after initial preparation, then co-cultured with γ-irradiated CH27 cells preloaded with either the null peptide MCC 99A (20 μM), the antagonist MCC 99R (10 μM), or MCC 102G (20 μM). Supernatants were collected at 24 hours after stimulation and analyzed for IL-2 production by ELISA ±SD, n=3).

Figure 7A:
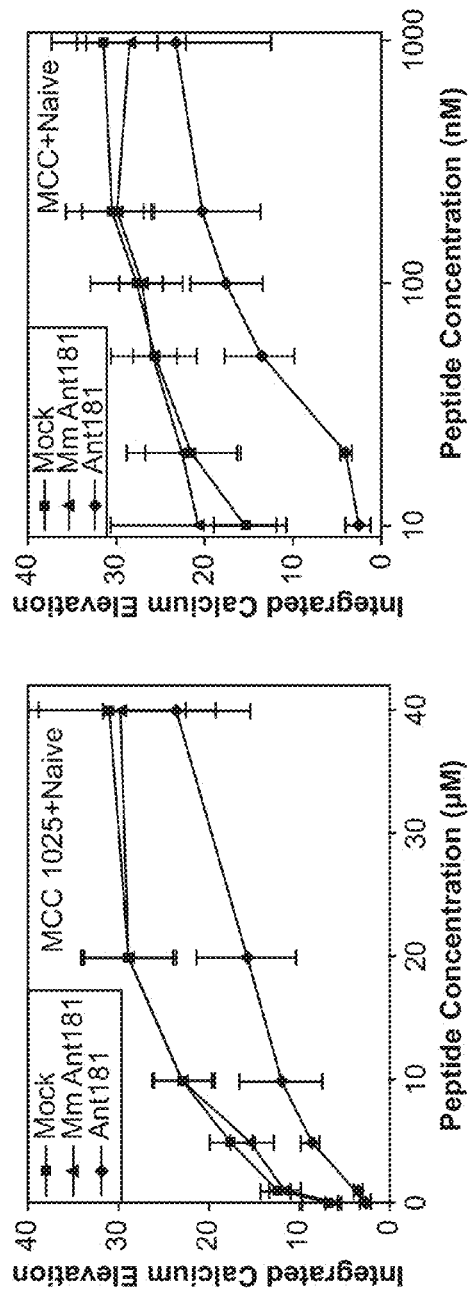
Figure 7B:
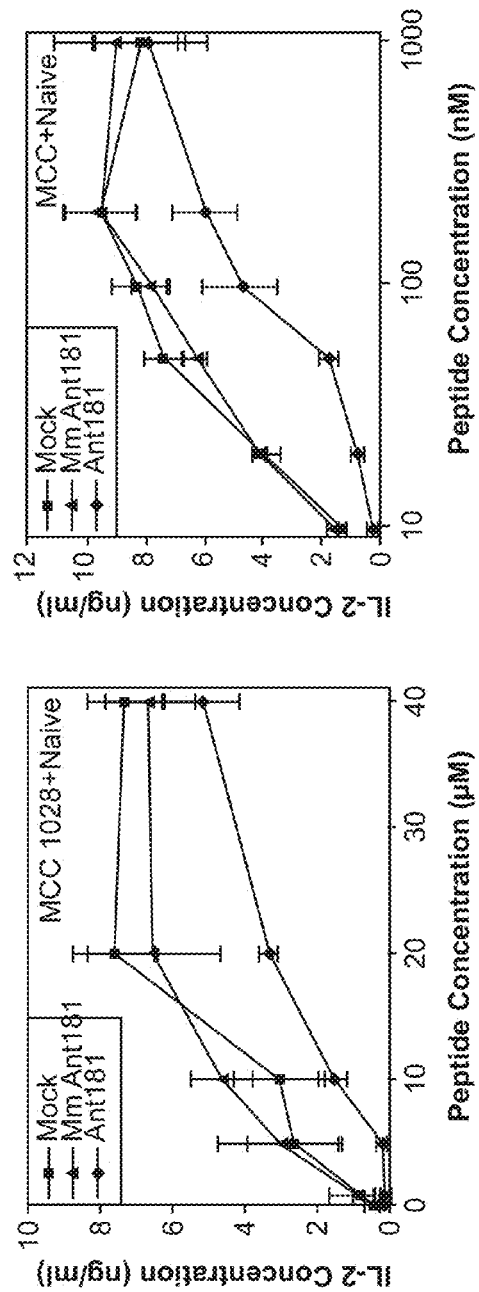

FIGS. 7A-7B. Reducing miR-181a expression dampens T cell sensitivity to antigens in naïve T cells. Naïve T cells isolated from the lymph nodes of 5C.C7 TCR transgenic mice on the Rag2-/- background were transfected with 50 μg/ml antagomir-181 (Ant181) or its mismatch control (Mm Ant181), and cultured for 16 hours in the presence of 5 ng/ml IL-7 before antigen stimulation. CH27 cells were loaded with various concentrations of agonist MCC or weak agonist MCC 102S and served as APC. T cell responses were measured by (A) calcium imaging or (B) IL-2 ELISA. (A) Effects of antagomir-181a on calcium responses (averaged integrated calcium value ±SEM, n=30); (B) Effects of antagomir-181a on IL-2 production ([IL-2]±SD, n=3). T cells were stimulated by co-culturing with γ-irradiated CH27 cells preloaded with antigenic peptide at a serial titration. Supernatants were collected 24 hours after stimulation.

FIGS. 8A-8D. MiR-181a controls thymocyte selection. (A) MiR-181a controls DP thymocyte negative selection. Fetal thymic organ cultures were established from e17 5C.C7 TCR transgenic mouse embryos on an li-/- B10BR background. Antagomir-181a (50 μg/ml) or the mock control was applied right after the initiation of the culture. 100 nM MCC, 5 μM MCC 99R or PBS control was introduced 24 hours after antagomir treatment. Single cell suspensions were prepared from cultured thymi 48 hours after peptide application. Data illustrated here represent 6 replicated experiments. (B) MiR-181a controls DP thymocyte positive selection. FTOC was performed with thymi dissected from e15 or e16 5C.C7 wild type embryos (absent of SP cell) and antagomir-181a (50 μg/ml) or the mock control was applied right after the initiation of culture. Thymocytes were collected after 4-5 days and stained for CD4 and CD8 to discriminate thymocyte populations. CD69 and CD62L stainings were also performed to verify the post-selection phenotype of SP cells. Data illustrated here represent 6 replicated experiments. (C) Antagomir-181a impairs DP cell responsiveness to antigen. DP cells were prepared from the thymus of adult 5C.C7 li-/- mice and pretreated with Cy3 labeled antagomir-181a at various concentrations for 12 hours. CH27 cells served as APC after loading with 0.5 μM MCC (solid line), 0.5 μM MCC 102S (dotted line) or PBS as a control (grey line). DP cells and APCs were cocultured for 3 hours then stained for CD4, CD8 and the T cell early activation marker CD69. Left panel, dose-dependent uptake of antagomir-181a in DP cells; right panel, the responsiveness of DP cells represented by surface CD69 elevation. (D) Antagomir-181a inhibits ERK activation in DP thymocytes. DP cells were prepared from the thymus of adult 5C.C7 li-/- mice and pretreated with 50 μg/ml antagomir-181a for 12 hours. CH27 cells served as APC after loading with 10 μM MCC 99R or PBS alone (grey line). The kinetics of ERK phosphorylation was probed as described in FIG. 4C.

Figure 9A:
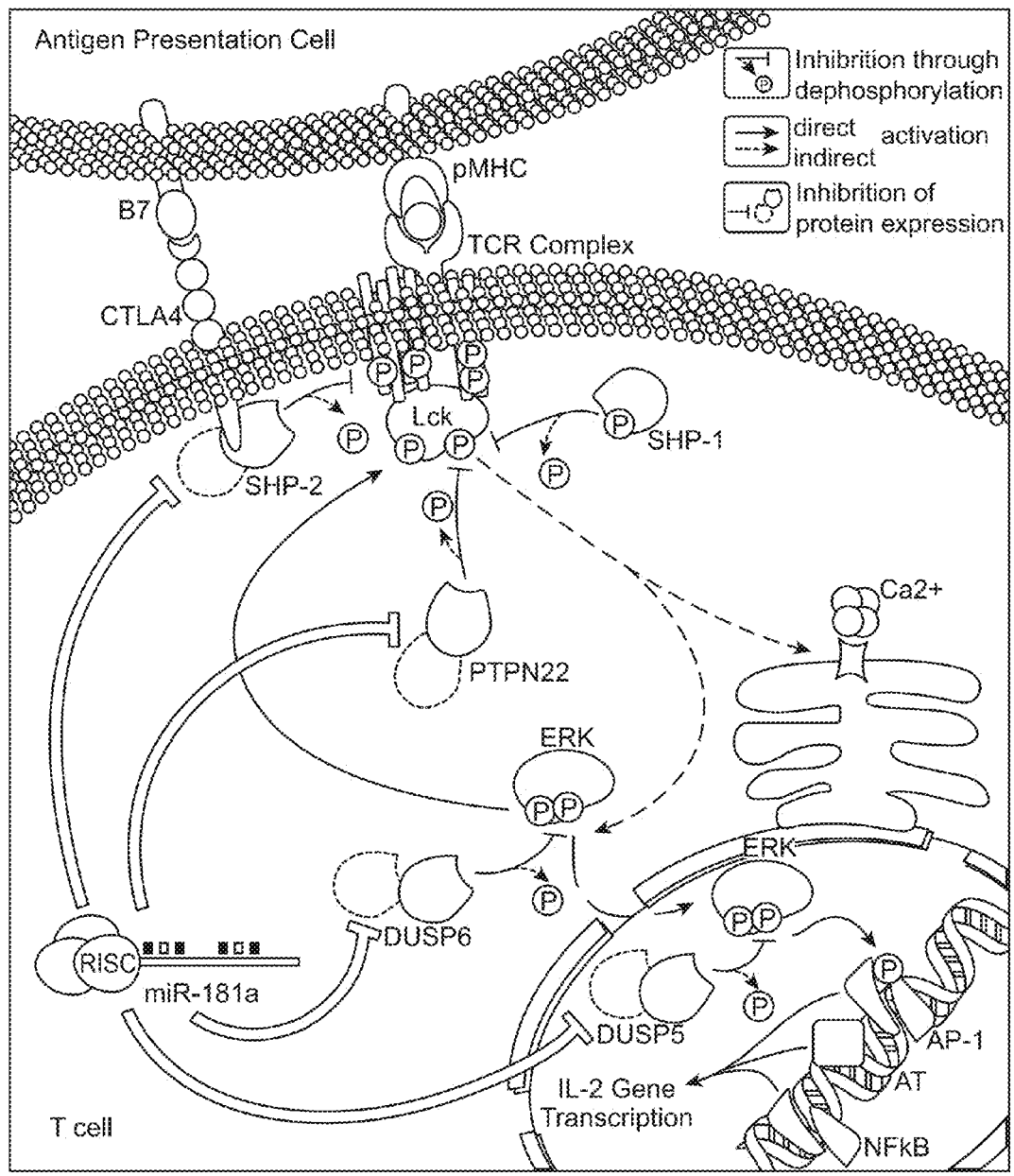
Figure 9B:
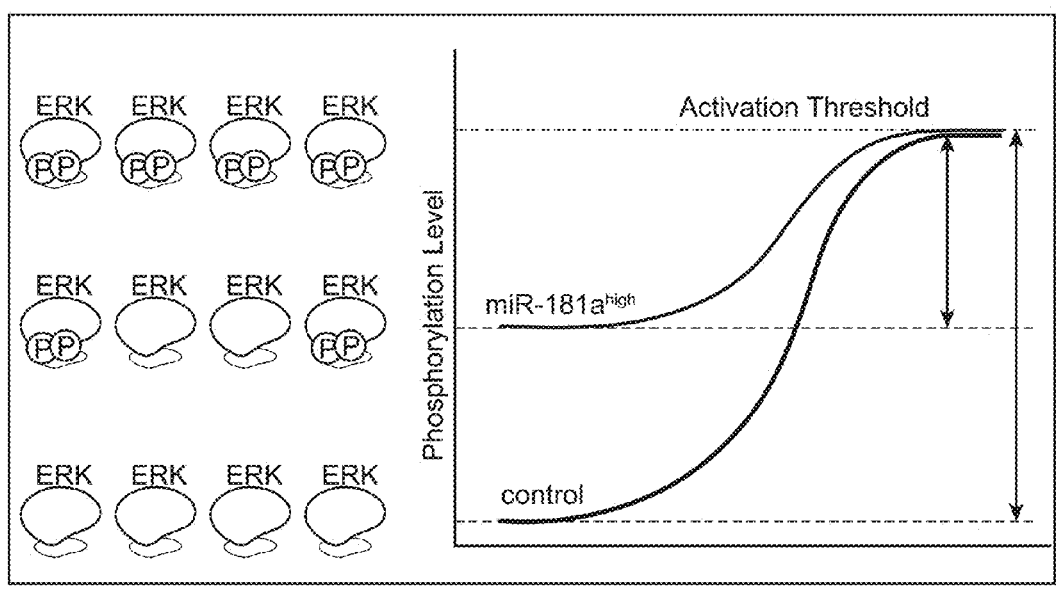

FIGS. 9A-9B Schematics of the miR-181a T cell sensitivity rheostat. (A) Molecular targets of miR-181a that controls TCR signaling threshold and T cell sensitivity. (B) A model for tuning TCR signaling threshold and T cell sensitivity to antigens. Selected signaling components are depicted.

Figure 10:
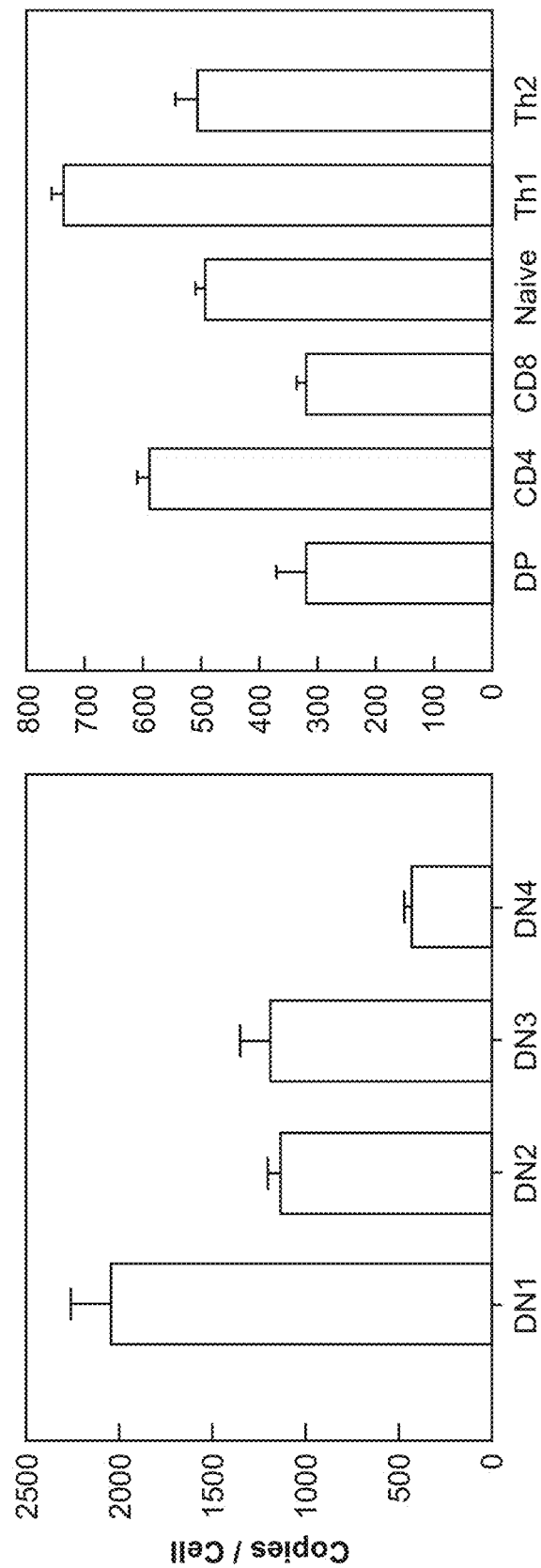

FIG. 10 qPCR analysis of developmental regulation of miR-142 expression in various purified T cell populations.

Figure 11A:
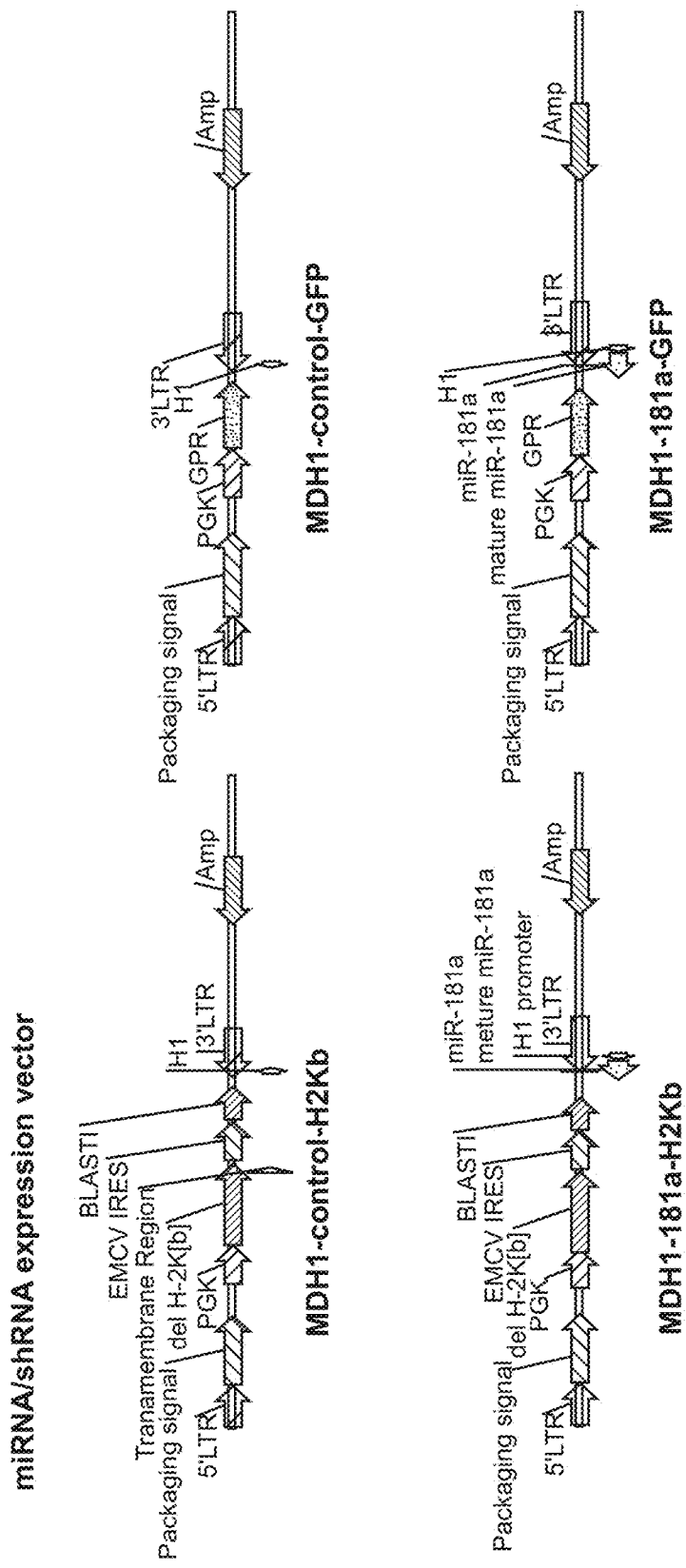
Figure 11B:
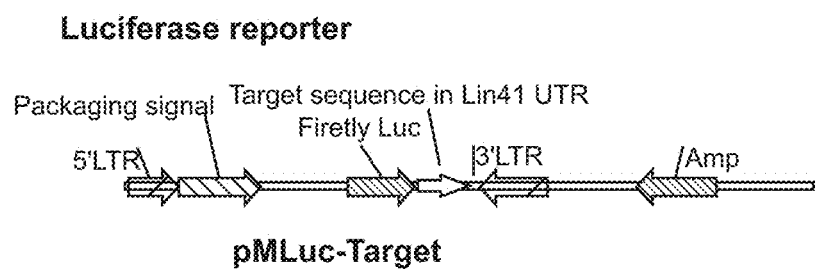
Figure 11C:
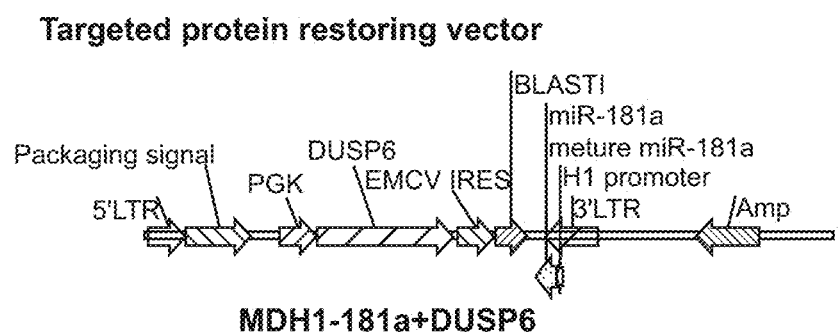
Figure 15A:
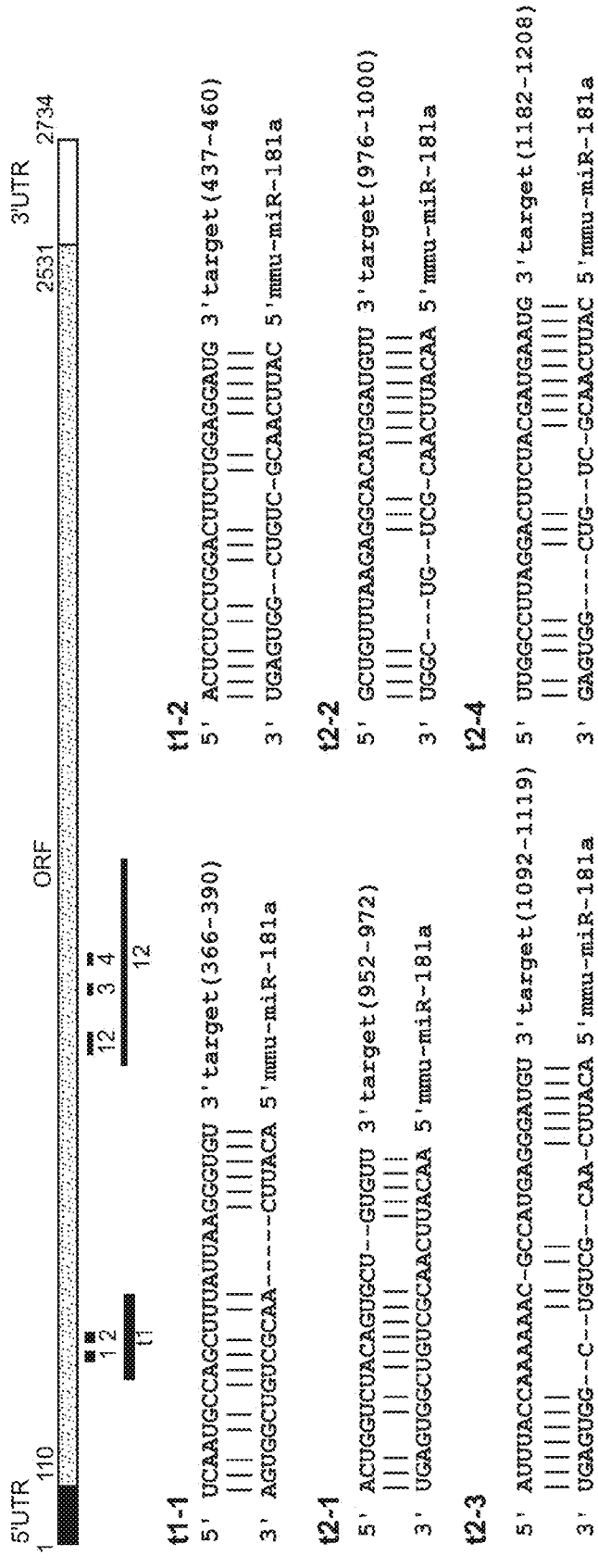
Figure 15B:
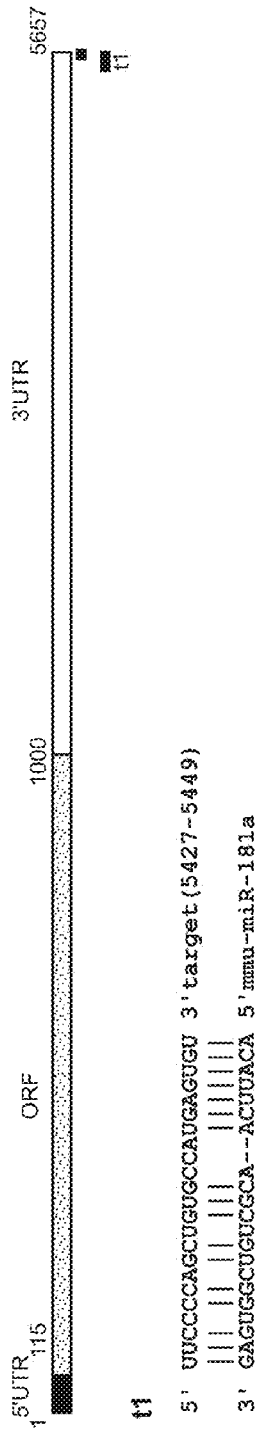
Figure 15C:
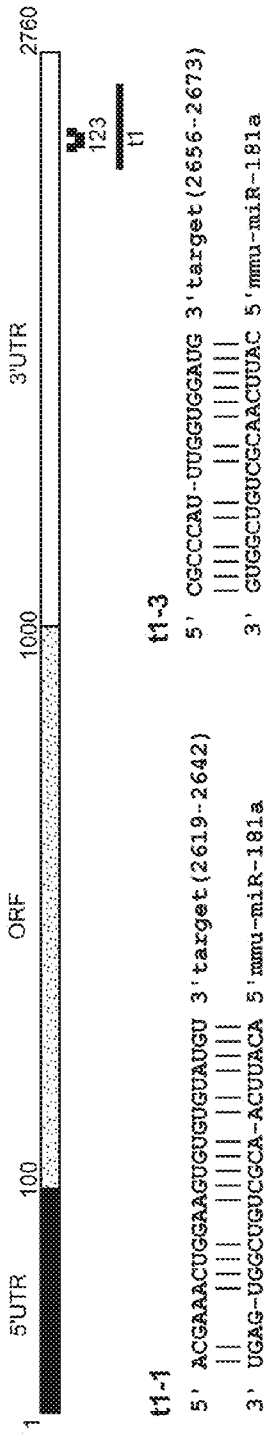
Figure 15D:
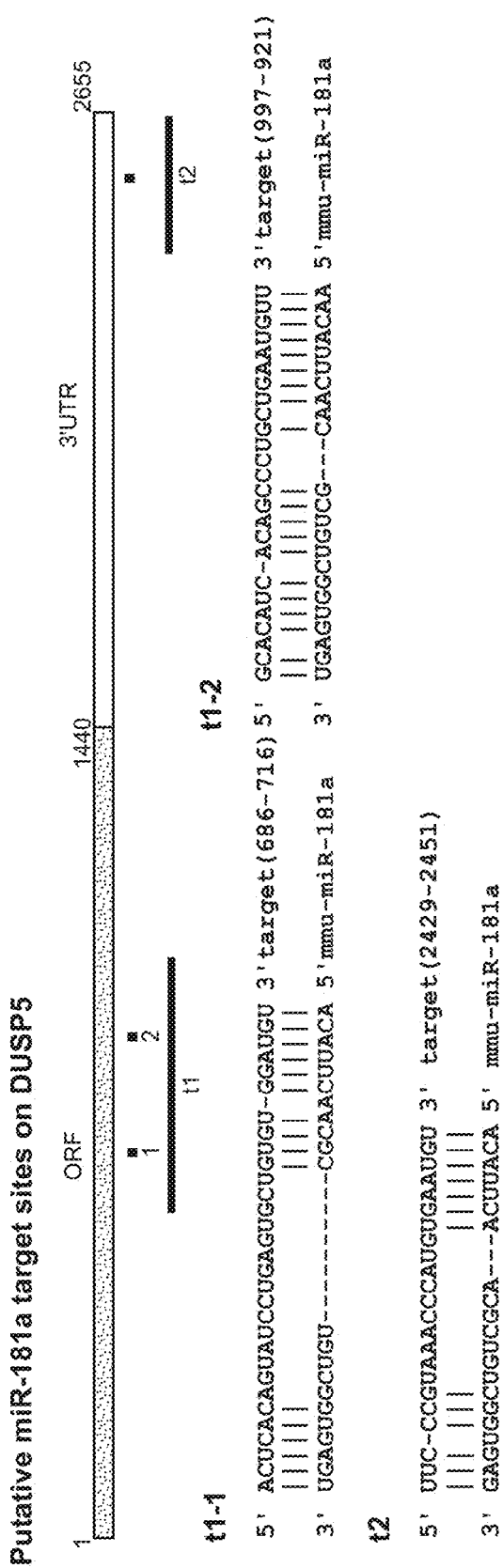

FIGS. 11A-11C. Schematics of miRNA and shRNA expression constructs (A), luciferase reporter constructs (B), and target restoring vectors (C).

FIGS. 12A-12B. A miR-181a mutant with dramatically reduced activity in augmenting TCR signaling strength. (A) Schematic representation of the wild-type (SEQ ID NO:1) and the mutant (SEQ ID NO:2) miR-181a precursor. The 5' 2nd and 3rd nucleotides of the mature miR-181a sequence were altered. Compensatory mutations were introduced into the precursor to preserve the secondary structure of pre-miR-181a. (B) 5C.C7 T cell blasts expressing control, miR-181a, or a miR-181a null mutant were stimulated with CH27 APCs preloaded with 0.1 μM of the agonist MCC. Calcium response of individual T cells was recorded by multichannel video-microscopy and analyzed with Meta-Morph software. 40 cells from each group were randomly selected and the integrated increases in cytosolic calcium concentration were scored for the first 5 minutes of the reaction. Err bar: SD.

FIGS. 13A-13D. (A & B) Effects of miR-181a expression on various T cell surface molecule expression. (A) Surface expression of 5C.C7 TCR and CD4 coreceptor on the miR-181a T cell blasts. Day6 5C.C7 T cells ectopically expressing miR-181a, miR-142, or control virus were stained with antibodies against 5C.C7 TCR (anti-Vβ3-PE)

and CD4 coreceptor (anti-CD4-PE-Cy5), and analyzed by flow cytometry. Histograms show the Vβ3 TCR or CD4 fluorescence intensity of the GFP$^+$ and CD4$^{high}$ cells. (B) Surface expression of the costimulation molecules CD28 and CTLA-4 on the miR-181a T cell blasts. T cell blasts were stained with antibodies against CTLA-4 (PE), CD4 (PE-Cy5), and CD28 (PE-Cy7), and analyzed by flow cytometry. Histograms show the CD28 and CTLA-4 fluorescence intensities of the GFP$^+$ and CD4$^{high}$ populations. Representative histograms of four independent experiments are shown in (A) and (B). (C & D) Effects on the costimulation pathway may in part contribute to the increased TCR signal strength in the miR-181a T cell blasts. 5C.C7 T cells ectopically expressing either miR-181a or control virus were activated by anti-CD3ε cross-linking or anti-CD3ε and CD28 double cross-linking. T cells were first incubated with either biotin-anti-CD3ε (10 μg/ml) and biotin-syrian hamster IgG control (10☐ μg/ml), or biotin-anti-CD3ε (10 μg/ml) and biotin-anti-CD28 (10 μg/ml). Calcium response was monitored with video-microscopy after adding streptavidin (2 μg/ml) to cross-link the TCR alone or TCR plus CD28. 30 T cells were randomly selected from each experimental group and the averaged intracellular calcium concentration was plotted as a function of time (C) and the integrated calcium responses during the first 5 minutes of stimulation are shown (D).

FIGS. 14A-14C. The effect of miR-181a on antagonist to agonist conversion is independent of its effects on the costimulation pathway. CH27 APCs preloaded with the antagonist MCC 99R (10 μM) were incubated with anti-B7.1 (10 μg/ml) and anti-B7.2 (10 μg/ml) at room temperature for 20 minutes to block the costimulation pathway and then used to challenge miR-181a T cell blasts for calcium image analysis. (A) Representative movie montages show that miR-181a T cell blasts react to the antagonist MCC 99R in the presence of costimulation blockade. DIC (top panel) and corresponding ratioed calcium images (bottom panel) taken at different time points after stimulation are shown. Fluorescence intensity of calcium signal is represented in a false color scale. (B) Average calcium level is plotted again time. Each data point represents the average calcium level of 30 responding T cells in each experimental group. (C) Integrated calcium responses during the first 5 minutes of stimulation are shown.

FIGS. 15A-15D. Alignment of miR-181a with predicted target sites from PTPN22 (A) SEQ ID NO 3, SEQ ID NO 4, SEQ ID NO 5, SEQ ID NO 6, SEQ ID NO 7, SEQ ID NO 8; SHP-2 (B) SEQ ID NO 9, DUSP6 (C) SEQ ID NO 10, SEQ ID NO 11, SEQ ID NO 12, and DUSP5 (D) SEQ ID NO 13, SEQ ID NO 14, SEQ ID NO 15.

Figure 16:
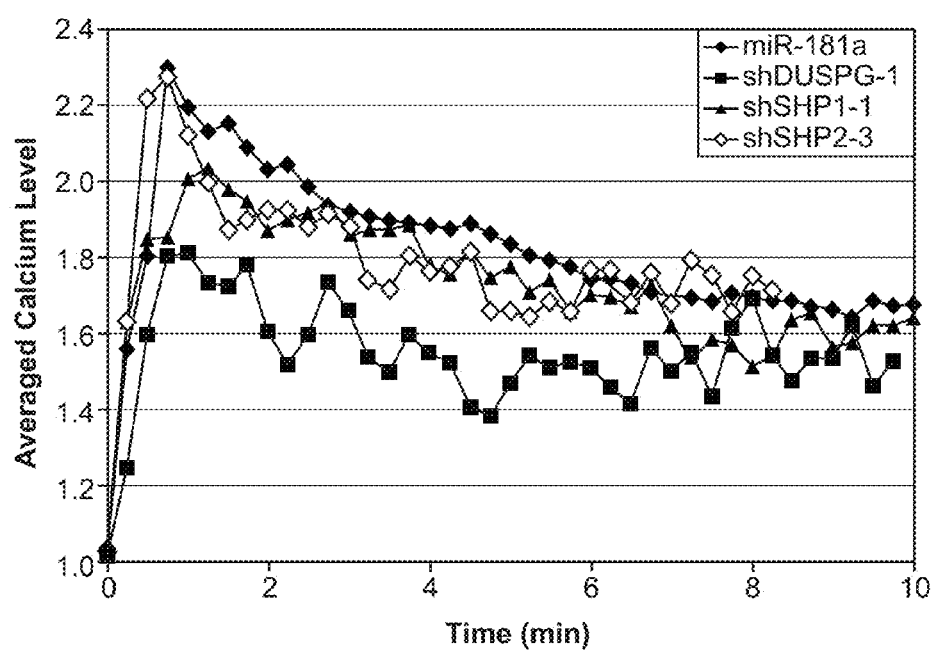

FIG. 16. Calcium responses to the antagonist MCC 99R in T cell blasts ectopically expressing shRNAs targeting individual miRNA-181a targets. Average calcium level was plotted again time. Each curve represents the average calcium level of 30 or more T cells in each experimental group. Only those T cells with medium to strong calcium responses (>8.0) are shown.

Figure 17A:
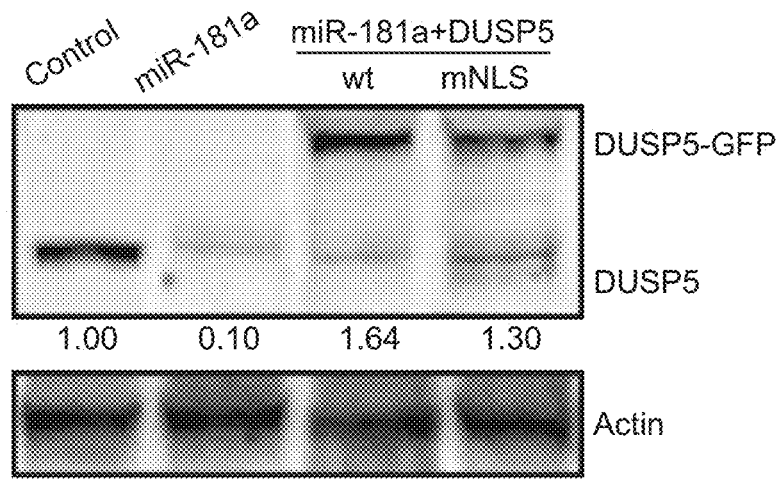
Figure 17B:
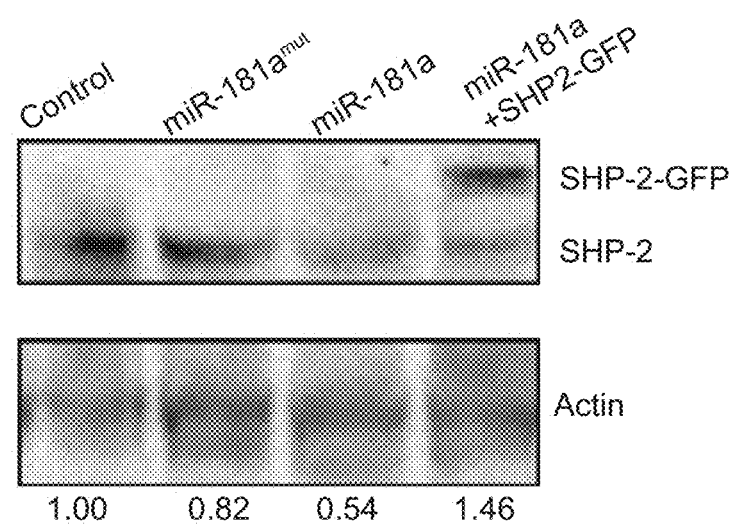

FIGS. 17A-17B. Effects of restoring individual target gene expression in the miR-181a T cell blasts on T cell reactivity to the antagonist MCC 99R. (A) Western-blot analysis of DUSP5-GFP expression in the miR-181a T cell blasts. Infected T cells were selected for blasticidin resistance and lysed at day 6 for Western blot analysis. Relative DUSP5 expression level was determined by densitometry and normalized to the actin loading control. (B) Western-blot analysis of SHP-2-GFP fusion protein expression in the miR-181a T cell blasts. DUSP5 and SHP-2 expression was restored by co-expression of miR-181a and the SHP-2-GFP fusion protein in the above-described vector described.

Figure 18A:
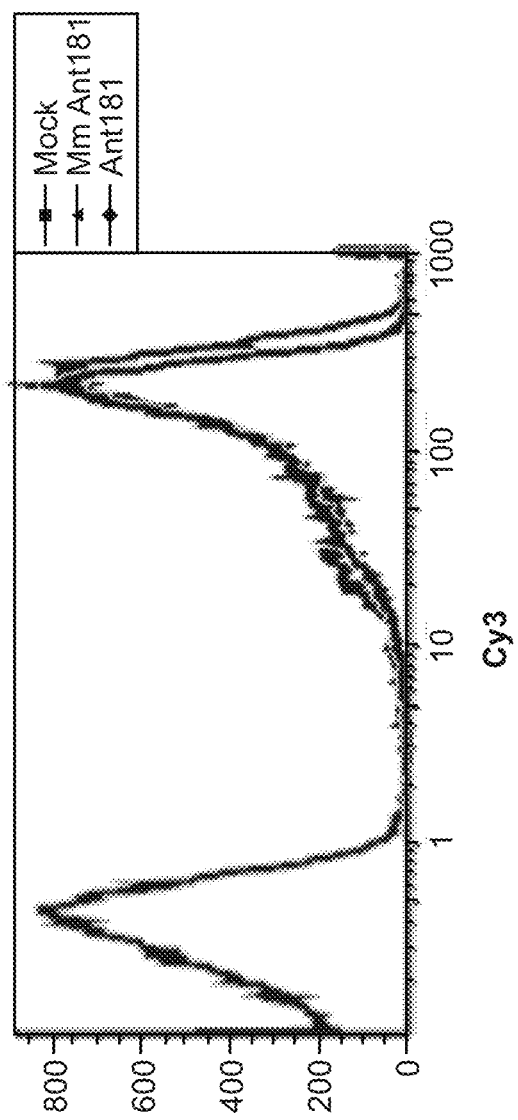
Figure 18B:
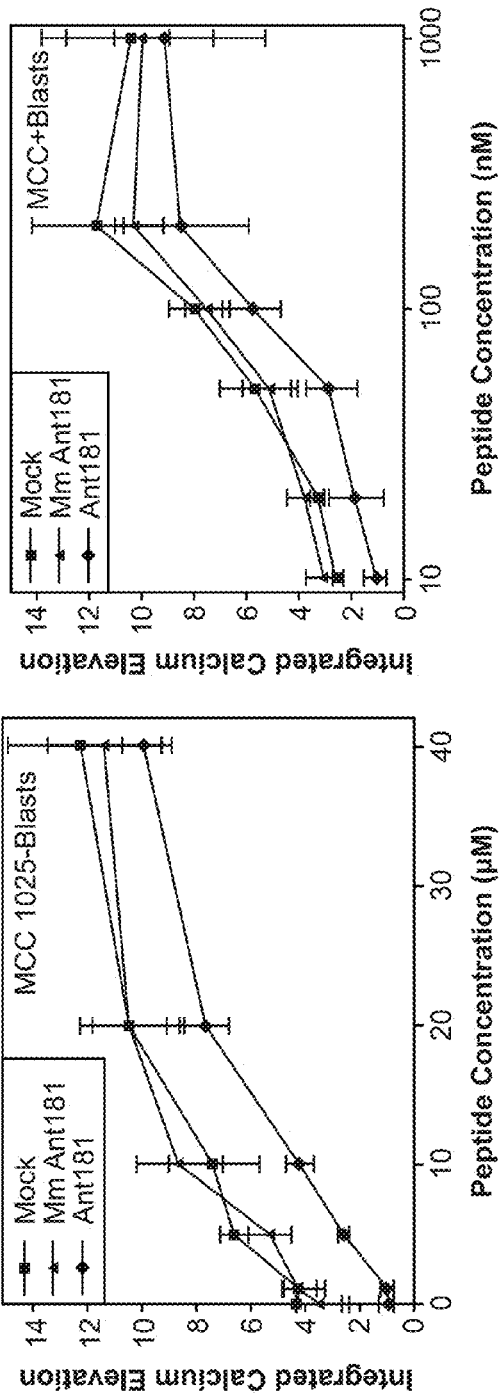
Figure 18C:
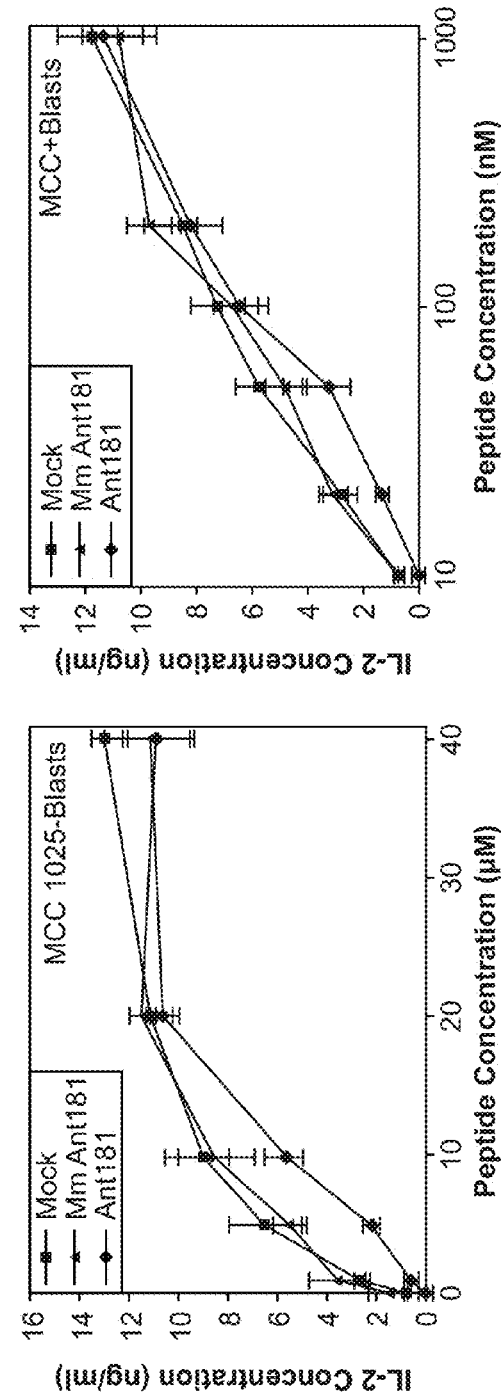

FIGS. 18A-18C. Knocking-down miR-181a expression reduces T cell sensitivity to antigens in primed T cell blasts. (A) FACS analysis of antagomir uptake in T cell blasts. T cell blasts were transfected with 5' Cy3 labeled antagomir-181a or its mismatch control (501?g/ml). Cells were gated on CD4 positive and analyzed at Cy3 channel. (B & C) Effects of antagomir-181a on calcium responses (B) and IL-2 production (C) in mature T cell blasts stimulated with APCs preloaded with various concentrations of agonist MCC or weak agonist MCC 102S (averaged integrated calcium value ±SEM, n=30; [IL-2]±SD, n=3). T cell blast responses to antigens were quantified by calcium flux or IL-2 secretion at 16 hours after antagomir transfection.

Figure 19:
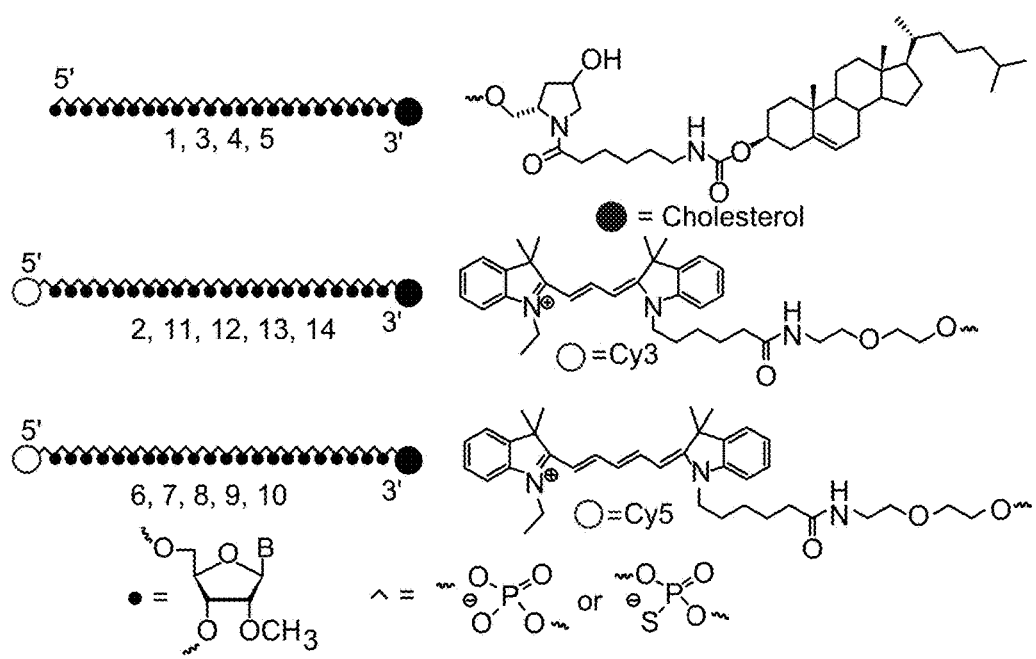

FIG. 19. Antagomir design with and without reporter group Cy3 (Quasar 570) or Cy5 (Quasar 670) at the 5'-end.

DETAILED DESCRIPTION OF THE EMBODIMENTS

Methods and compositions for altering T cell signaling threshold and sensitivity in a target cell are provided. In the subject methods, the activity of a miRNA is modulated. In some embodiments, the amount of the targeted miRNA in the target cell is reduced, e.g., by introducing a miRNA inhibitory agent in the target cell, thereby increasing the T cell signaling threshold in the targeted cell. In another embodiment, the amount of the targeted miRNA in a cell is increased, e.g. by introducing miRNA or an miRNA expression vector in the target cell, thereby decreasing the T cell signaling threshold in the target cell. Also provided are pharmaceutical compositions, kits and systems for use in practicing the subject methods. The subject invention finds use in a variety of applications, including the treatment of subjects suffering from undesirable T cell activity, e.g. in autoimmune diseases, graft rejection, allergic responses, etc.; and in subjects suffering from inadequate T cell activity, e.g. in directing immune responses to chronically infected cells, to tumor cells, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention provides methods and compositions modulating T cell signaling threshold and T cell sensitivity to antigen. In further describing the subject invention, the subject methods are described first in greater detail, followed by a review of various representative applications in which the subject invention finds use as well as kits that find use in practicing the subject invention.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

MicroRNAs (miRNAs) are an abundant class of non-coding RNAs that are believed to be important in many biological processes through regulation of gene expression. These noncoding RNAs that can play important roles in development by targeting the messages of protein-coding genes for cleavage or repression of productive translation. Humans have between 200 and 255 genes that encode miRNAs, an abundance corresponding to almost 1% of the protein-coding genes.

MicroRNAs of interest for use in the methods of the invention include those natural RNAs expressed in cells of the immune system. For example, see Min and Chen (2006) Methods Mol Biol. 342:209-27 for methods and strategies for dissecting miRNA function during hematopoietic lineage differentiation. Chowdhury and Novina (2005) Adv Immunol. 88:267-92, describe RNAi and RNA-based regulation of immune system function. Chowdhury and Novina (2005) Immunol Cell Biol. 83(3):201-10 discuss potential roles for short RNAs in lymphocytes. Each of these references is herein specifically incorporated by reference for the teaching of microRNAs expressed in cells of the immune system, and for the specific microRNAs disclosed.

miR-181a has been identified as one of three miRNAs that are specifically expressed in hematopoietic cells, with expression dynamically regulated during early hematopoiesis and lineage commitment. The role of miR-181 in the B-lymphoid cells has been described by Chen et al., supra. miR-181 is very strongly expressed in the thymus, the primary lymphoid organ, which mainly contains T lymphocytes. It is also strongly expressed in the brain and lung and is detectable in bone marrow and the spleen. Mature miR-181 expression has been reported in bone marrow cells and up-regulated in differentiated B lymphocytes, which are marked by the B220 surface antigen.

The nucleotide sequence of representative miR-181a sequences is provided in Table 1. It can be seen that the sequence is very highly conserved among primate and mammalian species.

TABLE 1 miR-181a Sequences

| organism | Genbank accession | DNA sequence | RNA sequence |
|---|---|---|---|
| Bos Taurus | DQ274916 | SEQ ID NO: 16<br>aacattcaacgctgtcggtgag | SEQ ID NO: 17<br>aacauucaacgcugucggugag |
| Macaca nemestrina | AY866169 | SEQ ID NO 18<br>aacattcaacgctgtcggtgag | SEQ ID NO 19<br>aacauucaacgcugucggugag |
| Saguinus labiatus | AY866168 | SEQ ID NO 20<br>aacattcaacgctgtcggtgag | SEQ ID NO 21<br>aacauucaacgcugucggugag |
| Macaca mulatta | AY866167 | SEQ ID NO 22<br>aacattcaacgctgtcggtgag | SEQ ID NO 23<br>aacauucaacgcugucggugag |

TABLE 1-continued miR-181a Sequences

| organism | Genbank accession | DNA sequence | RNA sequence |
|---|---|---|---|
| Pan troglodytes | AY866166 | SEQ ID NO 24<br>aacattcaacgctgtcggtgag | SEQ ID NO 25<br>aacauucaacgcugucggugag |
| Pan paniscus | AY866165 | SEQ ID NO 26<br>aacattcaacgctgtcggtgag | SEQ ID NO 27<br>aacauucaacgcugucggugag |
| Gorilla gorilla | AY866164 | SEQ ID NO 28<br>aacattcaacgctgtcggtgag | SEQ ID NO 29<br>aacauucaacgcugucggugag |
| Homo sapiens | | SEQ ID NO 30<br>aacattcaacgctgtcggtgagt | SEQ ID NO 31<br>aacauucaacgcugucggugagu |
| Mus musculus | AJ560723 | SEQ ID NO 32<br>aacattcaacgctgtcggtgagt | SEQ ID NO 33<br>aacauucaacgcugucggugagu |

As used herein, the term miR-181a may refer to any of the provided sequences, usually in reference to a 22 or 23 nucleotide polynucleotide comprising the sequence aacattcaacgctgtcggtgag. Included in the scope of the term "microRNA" is included synthetic molecules with substantially the same activity as the native microRNA, e.g. synthetic oligonucleotides having altered chemistries, as are known in the art.

In practicing the subject methods, an effective amount of a miR181a agent is introduced into the target cell, where any convenient protocol for introducing the agent into the target cell may be employed. The target cell is usually a cell of the T lymphocyte lineage, including, without limitation, hematopoietic stem cells, committed lymphocyte progenitors, pro-T cells, pre-T cells, thymocytes, mature T cells, and memory T cells. Mature T cells include th1 helper T cells, th2 helper T cells, th3 helper T cells, cytotoxic T cells, natural killer T cells (NKT cells), T regulatory cells, and the like.

The subject methods are used for prophylactic or therapeutic purposes. As used herein, the term "treating" is used to refer to both prevention of disease, and treatment of pre-existing conditions. For example, the prevention of autoimmune disease may be accomplished by administration of the agent prior to development of overt disease. The treatment of ongoing disease, where the treatment stabilizes or improves the clinical symptoms of the patient, is of particular interest.

As is known in the art, miRNAs are single stranded RNA molecules that range in length from about 20 to about 25 nt, such as from about 21 to about 24 nt, e.g., 22 or 23 nt. The target miR181a may or may not be completely complementary to the introduced miR181a agent. If not completely complementary, the miRNA and its corresponding target viral genome are at least substantially complementary, such that the amount of mismatches present over the length of the miRNA, (ranging from about 20 to about 25 nt) will not exceed about 8 nt, and will in certain embodiments not exceed about 6 or 5 nt, e.g., 4 nt, 3 nt, 2 nt or 1 nt.

The miR181a agent may increase or decrease the levels of miR181a in the targeted cell. Where the agent is an inhibitory agent, it inhibits the activity of the target miRNA by reducing the amount of miR181a RNA present in the targeted cells, where the target cell may be present in vitro or in vivo. By "reducing the amount of" is meant that the level or quantity of the target miRNA in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods.

Where the miR-181a agent increases the activity of the targeted miRNA in a cell, the amount of miR181a is increased in the targeted cells, where the target cell may be present in vitro or in vivo. By "increasing the amount of" is meant that the level or quantity of the target miRNA in the target cell is increased by at least about 2-fold, usually by at least about 5-fold, e.g., 10-fold, 15-fold, 20-fold, 50-fold, 100-fold or more, as compared to a control, i.e., an identical target cell not treated according to the subject methods.

By miRNA inhibitory agent is meant an agent that inhibits the activity of the target miRNA. The inhibitory agent may inhibit the activity of the target miRNA by a variety of different mechanisms. In certain embodiments, the inhibitory agent is one that binds to the target miRNA and, in doing so, inhibits its activity. Representative miRNA inhibitory agents include, but are not limited to: antisense oligonucleotides, and the like. Other agents of interest include, but are not limited to: Naturally occurring or synthetic small molecule compounds of interest, which include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing appropriate screening protocols.

The antisense reagent may be antisense oligonucleotides (ODN), particularly synthetic ODN having chemical modifications from native nucleic acids, or nucleic acid constructs that express such antisense molecules as RNA. The antisense sequence is complementary to the targeted miRNA, and inhibits its expression. One or a combination of antisense molecules may be administered, where a combination may comprise multiple different sequences.

Antisense molecules may be produced by expression of all or a part of the target miRNA sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5-O-phosphorothioate, 3'-CH2-5'-O-phosphonate and 3'-NH-5-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Anti-sense molecules of interest include antagomir RNAs, e.g. as described by Krutzfeldt et al., supra., herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing miRNAs in vivo, chemically modified, cholesterol-conjugated single-stranded RNA analogues complementary to miRNAs were developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

Also of interest in certain embodiments are RNAi agents. In representative embodiments, the RNAi agent targets the precursor molecule of the microRNA, known as pre-microRNA molecule. By RNAi agent is meant an agent that modulates expression of microRNA by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

Where it is desirable to increase miR-181a expression in a cell, e.g. to increase the sensitivity of a T cell to antigen, an agent may be miR-181a microRNA itself, including any of the modified oligonucleotides described above with respect to antisense, e.g. cholesterol conjugates, phosphorothioates linkages, and the like. Alternatively, a vector that expresses miR-181a, including the pre-miRNA sequence relevant to the targeted organism.

Expression vectors may be used to introduce the target gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g.

plasmid; retrovirus, e.g. lentivirus; adenovirus; and the like, where the vectors are able to transiently or stably be maintained in the cells, usually for a period of at least about one day, more usually for a period of at least about several days to several weeks.

The expression cassette will generally employ an exogenous transcriptional initiation region, i.e. a promoter other than the promoter which is associated with the T cell receptor in the normally occurring chromosome. The promoter is functional in host cells, particularly host cells targeted by the cassette. The promoter may be introduced by recombinant methods in vitro, or as the result of homologous integration of the sequence by a suitable host cell. The promoter is operably linked to the coding sequence of the autoantigen to produce a translatable mRNA transcript. Expression vectors conveniently will have restriction sites located near the promoter sequence to facilitate the insertion of autoantigen sequences.

Expression cassettes are prepared comprising a transcription initiation region, which may be constitutive or inducible, the gene encoding the autoantigen sequence, and a transcriptional termination region. The expression cassettes may be introduced into a variety of vectors. Promoters of interest may be inducible or constitutive, usually constitutive, and will provide for high levels of transcription in the vaccine recipient cells. The promoter may be active only in the recipient cell type, or may be broadly active in many different cell types. Many strong promoters for mammalian cells are known in the art, including the .beta.-actin promoter, SV40 early and late promoters, immunoglobulin promoter, human cytomegalovirus promoter, retroviral LTRs, etc. The promoters may or may not be associated with enhancers, where the enhancers may be naturally associated with the particular promoter or associated with a different promoter.

A termination region is provided 3' to the coding region, where the termination region may be naturally associated with the variable region domain or may be derived from a different source. A wide variety of termination regions may be employed without adversely affecting expression.

The various manipulations may be carried out in vitro or may be performed in an appropriate host, e.g. E. coli. After each manipulation, the resulting construct may be cloned, the vector isolated, and the DNA screened or sequenced to ensure the correctness of the construct. The sequence may be screened by restriction analysis, sequencing, or the like.

As indicated above, the miRNA agent can be introduced into the target cell(s) using any convenient protocol, where the protocol will vary depending on whether the target cells are in vitro or in vivo. A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

For example, the inhibitory agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. Methods for oral introduction include direct mixing of RNA with food of the organism. Physical methods of introducing nucleic acids include injection directly into the cell or extracellular injection into the organism of an RNA solution. The agent may be introduced in an amount which allows delivery of at least one copy per cell. Higher doses (e.g., at least 5, 10, 100, 500 or 1000 copies per cell) of the agent may yield more effective inhibition; lower doses may also be useful for specific applications.

When liposomes are utilized, substrates that bind to a cell-surface membrane protein associated with endocytosis can be attached to the liposome to target the liposome to T cells and to facilitate uptake. Examples of proteins that can be attached include capsid proteins or fragments thereof that bind to T cells, antibodies that specifically bind to cell-surface proteins on T cells that undergo internalization in cycling and proteins that target intracellular localizations within T cells. Gene marking and gene therapy protocols are reviewed by Anderson et al. (1992) Science 256:808-813.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc.

Depending n the nature of the agent, the active agent(s) may be administered to the host using any convenient means capable of resulting in the desired modulation of miR-181a in the target cell. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means.

Introduction of an effective amount of an miR-181a agent into a mammalian cell as described above results in a modulation of target gene(s) expression, resulting in a modification of the T cell signaling threshold and sensitivity to antigen.

The above described methods work in any mammalian cell, where representative mammal cells of interest include, but are not limited to cells of: ungulates or hooved animals, e.g., cattle, goats, pigs, sheep, etc.; rodents, e.g., hamsters, mice, rats, etc.; lagomorphs, e.g., rabbits; primates, e.g., monkeys, baboons, humans, etc.; and the like.

Before, during, or after treatment, the host may be assessed for immune responsiveness to a candidate antigen by various methods known in the art. The diagnosis may determine the level of reactivity, e.g. based on the number of reactive T cells found in a sample, as compared to a negative control from a naive host, or standardized to a data curve obtained from one or more patients. In addition to detecting the qualitative and quantitative presence of reactive T cells, the T cells may be typed as to the expression of cytokines known to increase or suppress inflammatory responses. It may also be desirable to type the epitopic specificity of the reactive T cells.

T cells may be isolated from patient peripheral blood, lymph nodes, or preferably from the site inflammation. Reactivity assays may be performed on primary T cells, or the cells may be fused to generate hybridomas. Such reactive T cells may also be used for further analysis of disease progression, by monitoring their in situ location, T cell receptor utilization, etc. Assays for monitoring T cell responsiveness are known in the art, and include proliferation assays and cytokine release assays.

Proliferation assays measure the level of T cell proliferation in response to a specific antigen, and are widely used in the art. In an exemplary assay, patient lymph node, blood or spleen cells are obtained. A suspension of from about $10^4$ to $10^7$ cells, usually from about $10^5$ to $10^6$ cells is prepared and washed, then cultured in the presence of a control antigen, and test antigens. The test antigens may be any peptides of interest. The cells are usually cultured for several days. Antigen-induced proliferation is assessed by the monitoring the synthesis of DNA by the cultures, e.g. incorporation of $^3$H-thymidine during the last 18 H of culture.

Enzyme linked immunosorbent assay (ELISA) assays are used to determine the cytokine profile of reactive T cells, and may be used to monitor for the expression of such cytokines as IL-2, IL-4, IL-5, γIFN, etc. The capture antibodies may be any antibody specific for a cytokine of interest, where supernatants from the T cell proliferation assays, as described above, are conveniently used as a source of antigen. After blocking and washing, labeled detector antibodies are added, and the concentrations of protein present determined as a function of the label that is bound.

The peptides may be defined by screening with a panel of peptides derived from the test protein. The peptides will have at least about 8 and not more than about 30 amino acids, more usually not more than about 20 amino acids in length. A panel of peptides may represent the length of a protein sequence, i.e. all residues are present in at least one peptide.

Where the miR-181a agent is acting to decrease expression of miR-181a, the net effect is to increase the threshold for antigen signaling, and to decrease the sensitivity of a T cell to antigen. The effect may be mediated in mature T cells, e.g. non-naïve T cells that have been exposed to an antigen of interest. Alternatively the target cell may be a progenitor to such mature T cells. Conditions of interest for downregulating T cells responses include allergic responses, autoimmune diseases, and in conjunction with transplantation, where graft rejection may occur as a result of T cell mediated immune responses.

Immune related diseases include: autoimmune diseases in which the immune response aberrantly attacks self-antigens, examples of which include but are not limited to multiple sclerosis (MS), acute disseminated encephalomyelitis (ADEM), rheumatoid arthritis (RA), type I autoimmune diabetes (IDDM), atherosclerosis, systemic lupus erythematosus (SLE), anti-phospholipid antibody syndrome, Guillain-Barre syndrome (GBS) and its subtypes acute inflammatory demyelinating polyradiculoneuropathy, and the autoimmune peripheral neuropathies; allergic diseases in which the immune system aberrantly attacks molecules such as pollen, dust mite antigens, bee venom, peanut oil and other foods, etc.; and tissue transplant rejection in which the immune system aberrantly attacks antigens expressed or contained within a grafted or transplanted tissue, such as blood, bone marrow cells, or solid organs including hearts, lungs, kidneys and livers; and the immune response against tumors. Samples are obtained from patients with clinical symptoms suggestive of an immune-related disease or with an increased likelihood for developing such a disease based on family history or genetic testing.

Other immune related diseases include allergy, or hypersensitivity, of the immune system, including delayed type hypersensitivity and asthma. Most cases of "atopic" or "allergic" asthma occur in subjects whom also exhibit immediate hypersensitivity responses to defined environmental allergens, and challenge of the airways of these subjects with such allergens can produce reversible airway obstruction. Both T cells and mast cells (and other FcRI+ cells) can have effector cell and immunoregulatory roles in these disorders.

NKT cells constitute a lymphocyte subpopulation that are abundant in the thymus, spleen, liver and bone marrow and are also present in the lung. They develop in the thymus from the CD4$^+$CD8$^+$ progenitor cells and circulate in the blood, have distinctive cytoplasmic granules, and can be functionally identified by their ability to kill certain lymphoid tumor cell lines in vitro without the need for prior immunization or activation. The mechanism of NKT cell killing is the same as that used by the cytotoxic T cells generated in an adaptive immune response; cytotoxic granules are released onto the surface of the bound target cell, and the effector proteins they contain penetrate the cell membrane and induce programmed cell death. There is evidence that suggests NKT cells are involved in the pathogenesis of conditions including asthma and certain autoimmune diseases.

Where a patient is undergoing transplantation, it may be desirable to downregulate generally or specifically the patient immune response. In such cases, the therapeutic miR-181a agent may be introduced prior to, concurrently with, or following the transplantation.

Where the miR-181a agent is acting to increase expression of miR-181a, the net effect is to decrease the threshold for signaling, and to increase the sensitivity of a T cell to antigen. Conditions of interest for upregulating T cell responsiveness include conditions where there is an inadequate immune response, e.g. in the induction of immune responsiveness to cancer, to chronically infected cells, and the like.

Upregulation of miR-181a finds use in eliciting an immune response in an autologous, allogeneic or xenogeneic host. For example, where a tumor cell or a chronically infected cell expresses a protein, or over-expresses the protein relative to normal cells, a cytolytic immune response may be induced, where the tumor cell or infected cell is preferentially killed. The antigen for such purposes may be from the same or a different species. As used herein, the term antigen is intended to refer to a molecule capable of eliciting an immune response in a mammalian host, which may be a humoral immune response, i.e. characterized by the production of antigen-specific antibodies, or a cytotoxic immune response, i.e. characterized by the production of antigen specific cytotoxic T lymphocytes. The miR-181a agent is administered in combination with the tumor antigen.

Several methods exist which can be used to induce an immune response against weakly antigenic protein, i.e. autologous proteins, etc. The immunogen is usually delivered in vivo to elicit a response, but in some cases it is advantageous to prime antigen presenting cells, e.g. dendritic cells, ex vivo prior to introducing them into the host animal.

In one embodiment, polypeptide antigens are mixed with an adjuvant that will augment specific immune reponses to the antigen, wherein the adjuvant comprises an agent that upregulated miR-181a in the targeted cell. Vaccine antigens may be presented using microspheres, liposomes, may be produced using an immunostimulating complex (ISCOM), as is known in the art.

Diagnostic and Prognostic Methods

In another embodiment of the invention, the detection of changes in miR-181a sequence, including changes in the promoter region, and the like, or expression of miR-181a is used as a marker in diagnostic or prognostic evaluation of a patient for conditions associated with T cell function, which conditions include, without limitation, a predisposition to autoimmune disease, a predisposition to T cell mediated immunodeficiency, a predisposition to atopy, and the like. Diagnostic methods include detection of specific markers correlated with specific stages in the pathological processes leading to conditions associated with T cell mediated immune dysfunction.

In general, such methods involve detecting altered levels or activity of miR-181a in the cells or tissue of an individual or a sample therefrom. A variety of different assays can be utilized to detect changes in expression, including both methods that detect the microRNA, the unprocessed transcripts, and evaluation of genomic sequences. More specifically, the diagnostic and prognostic methods disclosed herein involve obtaining a sample from an individual and determining qualitatively or quantitatively, the activity of miR-181a in the sample. Usually this determined value or test value is compared against some type of reference or baseline value. For example, a sequence that differs from the wild-type miR-181a sequence is a marker, as is altered expression levels relative to the wild-type.

Nucleic acids that are specific for the sequence of miR-181a are used to screen patient samples for altered activity of the microRNA, or for the presence of altered DNA in the cell. Samples can be obtained from a variety of sources. For example, since the methods are designed primarily to diagnosis and assess risk factors for humans to T cell mediated immune disorders, samples are typically obtained from a human subject. However, the methods can also be utilized with samples obtained from various other mammals, such as primates, e.g. apes and chimpanzees, mice, cats, rats, and other animals. Such samples are referred to as a patient sample.

Samples can be obtained from the tissues or fluids of an individual, as well as from cell cultures or tissue homogenates. For example, samples can be obtained from peripheral blood, serum, semen, saliva, tears, urine, fecal material, etc., preferably a hematopoietic cell sample. Also included in the term are derivatives and fractions of such cells and fluids. Samples can also be derived from in vitro cell cultures, including the growth medium, recombinant cells and cell components. The number of cells in a sample will often be at least about $10^2$, usually at least $10^3$, and may be about $10^4$ or more. The cells may be dissociated, in the case of solid tissues, or tissue sections may be analyzed. Alternatively a lysate of the cells may be prepared.

The various test values determined for a sample from an individual believed to have an immune dysfunction are typically are compared against a baseline value to assess the extent of altered activity or expression, if any. This baseline value can be any of a number of different values. In some instances, the baseline value is a value established in a trial using a healthy cell or tissue sample that is run in parallel with the test sample. Alternatively, the baseline value can be a statistical value (e.g., a mean or average) established from a population of control cells or individuals. For example, the baseline value can be a value or range which is characteristic of a control individual or control population. For instance, the baseline value can be a statistical value or range that is reflective of expression levels for the general population, or more specifically, healthy individuals not susceptible to T cell mediated immune dysfunction.

Some of the diagnostic and prognostic methods that involve the detection of miR-181a begin with the lysis of cells and subsequent purification of nucleic acids from other cellular material, particularly RNA transcripts. A nucleic acid derived from an RNA transcript refers to a nucleic acid for whose synthesis the RNA transcript, or a subsequence thereof, has ultimately served as a template. Thus, a cDNA reverse transcribed from an RNA, an RNA transcribed from that cDNA, a DNA amplified from the cDNA, an RNA transcribed from the amplified DNA, are all derived from the RNA transcript and detection of such derived products is indicative of the presence and/or abundance of the original transcript in a sample. Thus, suitable samples include, but are not limited to, RNA transcripts, cDNA reverse transcribed from the RNA, cRNA transcribed from the cDNA, DNA amplified from nucleic acids, and RNA transcribed from amplified DNA.

A number of methods are available for analyzing nucleic acids for the presence of a specific sequence, e.g. upregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2, 7-dimethoxy-4, 5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes for an ischemia associated gene or ischemia pathway gene is then contacted with the cells and the probes allowed to hybridize with neuroprotective gene nucleic acids. Excess probe is digested, washed away and the amount of hybridized probe measured. This approach is described in greater detail by Harris, D. W. (1996) Anal. Biochem. 243:249-256; Singer, et al. (1986) Biotechniques 4:230-250; Haase et al. (1984) Methods in Virology, vol. VII, pp. 189-226; and Nucleic Acid Hybridization: A Practical Approach (Hames, et al., eds., 1987).

A variety of so-called "real time amplification" methods or "real time quantitative PCR" methods can also be utilized to determine the quantity of ischemia associated gene or ischemia pathway gene mRNA present in a sample. Such methods involve measuring the amount of amplification product formed during an amplification process. Fluorogenic nuclease assays are one specific example of a real time quantitation method that can be used to detect and quantitate miR-181a. In general such assays continuously measure PCR product accumulation using a dual-labeled fluorogenic oligonucleotide probe—an approach frequently referred to in the literature simply as the "TaqMan" method.

The probe used in such assays is typically a short (ca. 20-25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. For measuring miR-181a, the probe is designed to have at least substantial sequence complementarity with a probe binding site on the miR-181a transcript. Upstream and downstream PCR primers that bind to regions that flank the miR-181a gene may also added to the reaction mixture. Probes may also be made by in vitro transcription methods.

When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter dye from the polynucleotide-quencher complex and resulting in an increase of reporter emission intensity that can be measured by an appropriate detection system.

Compound Screening

Compound screening may be performed using an in vitro model, a genetically altered cell or animal, purified microRNA, purified protein corresponding to polypeptides demonstrated herein to be regulated by miR-181a, and the like. One can identify ligands or substrates that bind to, modulate, inhibit, potentiate, or mimic the action of the microRNA. Assays may include functional analysis of T cell function, e.g. as provided in the Examples, where calcium uptake, cytokine production, etc. is monitored in a T cell in the absence or presence of a candidate agent. Other assays include analysis of expression of proteins identified herein as being regulated by miR-181a. Assays may also include analysis of the specific phosphatase proteins for enzymatic activity, to the effect of the microRNA on phosphatase expression, etc.

In one embodiment, compound screening is performed to determine the activity of a candidate agent with respect to dampening the activity of multiple negative regulators in the T cell receptor (TCR) signaling pathway, including PTPN22 (PTP-PEST) and the dual specificity phosphatases DUSP5 and DUSP6 (PYST1). In such a screening assay, for example, a candidate agent may be tested for coordinate down-regulation of the activity of PTPN22, DUSP5 and DUSP6. Such an agent may be tested by contacting the purified proteins with a candidate agent, e.g. a phosphatase inhibitor with specificity broad enough to inhibit at least partially each of these enzymes, and testing the activity of the phosphatase in a suitable assay, e.g. against known substrates. For example, see Kovanen et al. (2003) J Biol Chem. 278(7):5205-13; Dowd et al. (1998) J Cell Sci. 111 (Pt 22):3389-99; Matthews et al. (1992) Mol Cell Biol. 12(5):2396-405, each herein specifically incorporated by reference for teachings of assays relevant to the specific phosphatases. Alternatively, a cell may be contacted with a candidate agent for regulation of transcription or translation of each of these enzymes. In such assays, the miR-181a may serve as a positive control for coordinately regulating expression of these proteins.

The microRNA or phosphatase polypeptides include those that, by virtue of the degeneracy of the genetic code, are not identical in sequence to the disclosed nucleic acids, and variants thereof. Variant sequences can include amino acid (aa) or nucleotide substitutions, additions or deletions. The substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain and/or, where the polypeptide is a member of a protein family, a region associated with a consensus sequence). Variants also include fragments of the polypeptides disclosed herein, particularly biologically active fragments and/or fragments corresponding to functional domains. Fragments of interest will typically be at least about 10 to at least about 15 residues in length, usually at least about 50 residues in length, and can be as long as 300 residues in length or longer, but will usually not exceed about 500 residues in length.

Transgenic animals or cells derived therefrom are also used in compound screening. Transgenic animals may be made through homologous recombination, where the normal locus corresponding to a genetic sequence identified herein is altered. Alternatively, a nucleic acid construct is randomly integrated into the genome. Vectors for stable integration include plasmids, retroviruses and other animal viruses, YACs, and the like. A series of small deletions and/or substitutions may be made in the coding sequence to determine the role of different exons in kinase activity, oncogenesis, signal transduction, etc. Of interest is the use of miR-181a to construct transgenic animal models for immune dysfunction, where expression of the regulated polypeptides in the T cell signaling pathway are altered. Specific constructs of interest include antisense sequences that block expression of the targeted gene and expression of dominant negative mutations. A detectable marker, such as lac Z may be introduced into the locus of interest, where up-regulation of expression will result in an easily detected change in phenotype. One may also provide for expression of the target gene or variants thereof in cells or tissues where it is not normally expressed or at abnormal times of development. By providing expression of the target protein in cells in which it is not normally produced, one can induce changes in cell behavior.

Compound screening identifies agents that coordinately modulate activity of the miR-181a regulated polypeptides. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. Knowledge of the 3-dimensional structure of the encoded protein, derived from crystallization of purified recombinant protein, could lead to the rational design of small drugs that specifically inhibit activity. These drugs may be directed at specific domains.

The term "agent" as used herein describes any molecule, e.g. protein or pharmaceutical, with the capability of altering or mimicking the physiological function of a ischemia associated kinase corresponding to Ischemia associated genes. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to polypeptides in the TCR signaling pathway, e.g. PTN22, DUSP5 and DUSP6, as at least some of the compounds so identified are likely modulators of the activity of these proteins. The binding assays usually involve contacting a protein with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. The proteins utilized in such assays can be naturally expressed, cloned or synthesized.

Certain screening methods involve screening for a compound that modulates the expression of polypeptides in the TCR signaling pathway, e.g. PTN22, DUSP5 and DUSP6, usually coordinately modulates expression. Such methods generally involve conducting cell-based assays in which test compounds are contacted with one or more cells expressing polypeptides in the TCR signaling pathway, e.g. PTN22, DUSP5 and DUSP6 and then detecting and an increase in polypeptides in the TCR signaling pathway. Some assays are performed with cells of the immune system, e.g. T cells.

Expression can be detected in a number of different ways. The expression level of a gene in a cell can be determined by probing the mRNA expressed in a cell with a probe that specifically hybridizes with a transcript (or complementary nucleic acid derived therefrom) of the gene. Probing can be conducted by lysing the cells and conducting Northern blots or without lysing the cells using in situ-hybridization techniques. Alternatively, a protein can be detected using immunological methods in which a cell lysate is probe with antibodies that specifically bind to the protein.

Other cell-based assays are reporter assays. Certain of these assays are conducted with a heterologous nucleic acid construct that includes a promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) Nature 282:864-869), luciferase, β-galactosidase and alkaline phosphatase (Toh, et al. (1980) Eur. J. Biochem. 182:231-238; and Hall et al. (1983) J. Mol. Appl. Gen. 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. As indicated above, the baseline value can be a value for a control sample or a statistical value that is representative of a control population (e.g., healthy individuals). Expression levels can also be determined for cells that do not express one of the signaling pathway genes as a negative control. Such cells generally are otherwise substantially genetically the same as the test cells.

A variety of different types of cells can be utilized in the reporter assays. Certain cells are T cells. Other eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal that serves as a model for humans and then determining if the T cell signaling pathway has been altered. The animal models utilized in validation studies generally are mammals. Specific examples of suitable animals include, but are not limited to, primates, mice, and rats.

Certain methods are designed to test not only the ability of a lead compound to alter activity in an animal model, but to provide protection against immune dysfunction. In such methods, a lead compound is administered to the model animal (i.e., an animal, typically a mammal, other than a human). The animal is subsequently subjected to an immune challenge, e.g. immunization with an autoantigen, allergic challenge, etc. Compounds able to achieve the desired effect are good candidates for further study.

Active test agents identified by the screening methods described herein can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

EXPERIMENTAL

Example 1

T cell sensitivity to antigen is intrinsically regulated during maturation to ensure proper development of tolerance and immunity, but the molecules that govern this refinement remain elusive. Here we show that miR-181a, a member of an abundant class of ~22 nucleotide endogenous small regulatory RNAs, can quantitatively modulate T cell sensitivity to antigens by controlling the expression of multiple target genes. Increasing miR-181a expression in mature T cells causes a marked increase in T cell activation and augments T cell sensitivity to peptide antigens. Moreover, T cell blasts with higher miR-181a expression become reactive to antagonists—the inhibitory peptide antigens that are normally incapable of T cell activation alone but can block agonist ligand stimulation. These effects are in part achieved by reducing the expression of multiple negative regulators in the T cell receptor (TCR) signaling pathway, including PTPN22 and the dual specificity phosphatases DUSP5 and DUSP6. This results in an increase in the steady state levels of phosphorylated intermediates in the TCR signaling pathway and a reduction in the TCR signaling threshold, thus quantitatively and qualitatively enhancing T cell sensitivity to antigens. Consistent with the observation that higher miR-181a expression correlates with greater T cell sensitivity in immature T cells, inhibiting miR-181a expression by a specific "antagomir" reduces the sensitivity to antigens in naïve T cells and affects positive and negative selection in thymocytes. Thus miR-181a acts as a 'rheostat' that tunes T cell sensitivity at various stages of T cell development.

One of the key features of a functioning immune system is its ability to distinguish antigens of foreign origin from those derived endogenously and to mount an immune response against the former. With respect to T cells, this goal is achieved through antigen recognition by T cell receptors (TCRs) and a highly ordered developmental process in the thymus and in secondary lymphoid organs. TCRs constantly sample a diverse set of self and foreign peptide antigens presented in major histocompatibility complexes (MHCs) on the surface of antigen presenting cells (APCs) and these interactions elicit discrete intracellular signals and T cell responses. The mature T cell's response to antigen is largely dictated by the binding characteristics of its TCR for a given peptide-MHC complex (pMHC). In general, pMHC ligands with slower dissociation rates produce stronger TCR signals and lead to higher T cell reactivity to the antigenic peptides. Even in cases where there is not an apparent correlation with dissociation rate in solution, recent theoretical work suggests that this may well reflect the stability of TCR:pMHC complex in the context of cell-cell interactions.

Variations in the antigenic peptide affinities to TCRs may lead to both quantitative and qualitative changes in its ability to activate TCR signaling pathways and T cell responses. Typically, the most stable pMHC complexes with respect to TCR binding are agonists, while the less stable variants are weak agonists and then antagonists, which are not able to activate T cells more than partially themselves and also block responses to agonist ligand. Although a number of models have been proposed to explain the kinetic discrimination in T cell activation, exactly how T cells sense quantitative changes in antigenic peptide affinities through their TCRs and produce both quantitatively and qualitatively different responses remains an intensive area of study.

In addition, T cell responsiveness and TCR signaling to a specific ligand also vary with different developmental stages, suggesting that T cell sensitivity to antigens is intrinsically regulated during development. For example, in immature CD4+CD8+ double positive thymocytes, low affinity antigenic peptides that are unable to activate mature effector T cells are sufficient to induce strong activation and clonal deletion; antagonists that are normally inhibitory to effector T cells can induce positive selection. These observations demonstrate that T cell sensitivity is intrinsically regulated to ensure the proper development of specificity and sensitivity to foreign antigens while avoiding self-recognition. However, little is known about how intrinsic molecular programs influence T cell sensitivity toward antigens.

Recent studies suggest that miRNA-mediated gene regulation may represent a fundamental layer of posttranscriptional genetic programs in metazoan genomes and have broad effects on gene expression. MiRNA genes are an integral component of animal genomes and are dynamically regulated during development. These ~22-nt RNAs can repress the expression of protein-coding genes by targeting cognate messenger RNAs for degradation or translational repression. The cellular protein machineries involved in miRNA processing and function were also shown to play important functional roles, for example in the development of limbs and T cells in mice.

Furthermore, many miRNAs are differentially regulated in hematopoietic lineages and some have been shown to play roles in controlling the development of immune cells. The mechanisms by which miRNAs exert these effects are unclear, as is whether they have any specific role in the adaptive immune response.

Dynamic Regulation of miR-181a Expression During T Cell Development. Among many known hematopoietic miRNAs, miR-181a is preferentially expressed in the B cell but not T cell lineages in the mouse bone marrow. Ectopic expression of miR-181a in hematopoietic stem/progenitor cells results in a marked increase in B cell differentiation, while accompanied by a decrease in the percentage of T lymphocytes in the peripheral blood of transplanted mice. Interestingly, miR-181a is also strongly expressed in the mouse thymus, which consists mainly of T cells, suggesting that miR-181a may play some role in the development and function of T cells.

We examined how miR-181a expression is regulated during T cell development and maturation. T cell differentiation in the thymus can be divided into discrete stages characterized by the expression of CD4 and CD8 coreceptors. CD4 and CD8 double-negative (DN) cells, which are the early T cell progenitors in the thymus, can differentiate into CD4 and CD8 double positive cells (DP), and then further differentiate into mature CD4 or CD8 single-positive (SP) cells. DN cells can be further fractionated based on the expression of CD44 and CD25 into DN1 (CD44+ CD25−), DN2 (CD44+ CD25+), DN3 (CD44− CD25+), and DN4 (CD44− CD25−) cell populations, in the order of their appearance during development. We purified these thymic T cell populations by FACS sorting according to surface marker expression. We also obtained CD4+ naïve T cells from the lymph nodes of Rag2−/−5C.C7-αβTCR transgenic mice and derived Th1 and Th2 effector cells.

Further analysis of miR-181a expression in these immature and mature T cell populations using a quantitative real-time PCR assay revealed a very dynamic regulation of miR-181a expression during T cell maturation (FIG. 1A). MiR-181a expression is high in the early T cell differentiation stages in thymus, and its expression is significantly up-regulated from ~427 to ~858 to ~1077 copies/cell in the DN1-3 cell populations, respectively. MiR-181a expression then decreases in the later stages. Its expression drops sharply to ~225, 141, 42, 14 copies/cell in DN4, DP, CD4 SP, and CD8 SP thymocytes, respectively. Similarly, we noticed a further decrease of miR-181a expression to ~29 copies/cell in naïve cells, but only ~12 and ~8 copies/cell in the blasts of Th1 and Th2 cells, respectively (FIG. 1A). The results section till this point are duplicate of para 00145 to 00147. Do we let it be present in duplicate as it is relevant to the rest of the example here? Notably, when comparing to the mature Th1 and Th2 effector cells, miR-181a expression levels seem to be relatively higher in DP populations—the T cell populations that are more sensitive to pMHCs with low or intermediate affinities.

In comparison, miR-142-3p, a hematopoietic-specific miRNA, has distinct expression patterns during T cell development and maturation. The dynamic regulation of miR-181a expression in various T cell populations indicates that miR-181a plays a role in T cell maturation and functional differentiation (FIG. 1A). Indeed, using a OP9-DL1 (delta-like-1) stromal and thymocyte coculture assay, we have shown that ectopic expression of miR-181a in DN thymic progenitor cells cause a quantitative increase in the percentage of DP cells and a decrease in the CD8+ cells, suggesting that miR-181a can influence the development of thymic progenitor cells during both pre-TCR and TCR dependent stages.

MiR-181a Augments TCR Signaling Strength. To investigate miR-181a's role, if any, in antigen recognition by mature T cells, we assessed the effect of its expression on TCR signaling in CD4$^+$ T cell blasts. We increased the expression of miR-181a in primed T cell blasts derived from 5C.C7 TCR transgenic mice by retroviral transduction. Ectopic expression resulted in an approximately three to five-fold increase in miR-181a levels in the mature T cell blasts. T cells were then stimulated with CH27 antigen presenting cells (APCs) pre-loaded with a non-saturating amount of agonist peptide derived from Moth Cytochrome C (MCC a.a.88-103), and then TCR signaling strength was determined by measuring calcium elevation using video microscopy and ratio imaging.

Figure 2D:
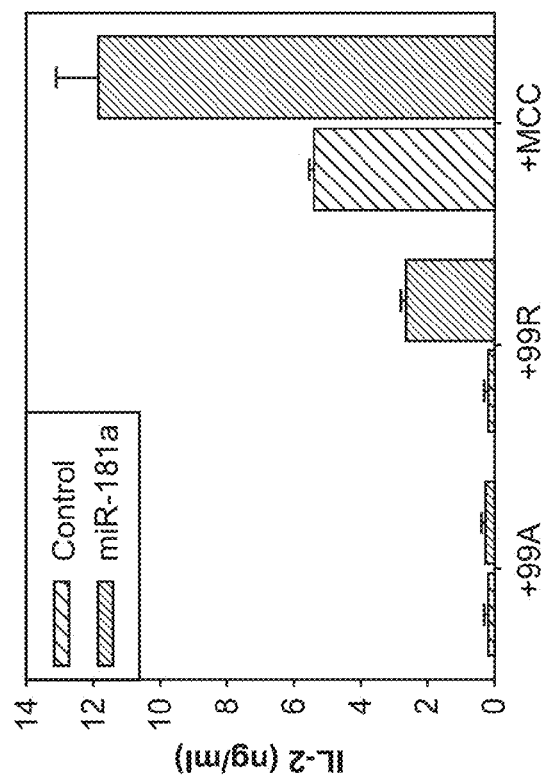

Elevated miR-181a expression in T cell blasts resulted in a substantial increase in intracellular calcium upon stimulation by the MCC peptide antigen, whereas a mutant miR-181a with alterations in its 5' 2 and 3 nucleotides largely abolished this activity (FIG. 12). Furthermore, miR-181a expression in T cells increased IL-2 production by two-fold compared to the control (FIG. 2D). These results show that increased miR-181a expression augments TCR mediated T cell activation.

To quantify the effects of miR-181a on TCR signaling, we measured TCR signal output in response to antigen stimulation at the single cell level (FIGS. 1B&C). The TCR signal input is defined as the number of antigenic peptide MHC complexes at the interface between T cells and APCs, and the output is measured by the calcium concentration changes in the T cell cytosol. In T cell blasts infected with control virus (the control T cell blasts), ~5 MCC peptides are needed to produce a half-maximal calcium response (EC50) (FIGS. 1B&D). This response is essentially identical to that of uninfected T cell blasts, suggesting that viral infection did not cause discernable changes in TCR signaling.

In comparison, in the T cell blasts transduced with the miR-181a construct (the miR-181a T cell blasts), only ~2 MCC peptides are required to reach the EC50 (FIGS. 1C&D), showing that miR-181a expression increases T cell sensitivity by more than two-fold. Also notable is that, signal output in the miR-181a expressing T cells is about 40% higher than that in the control T cells, as indicated by the plateau calcium flux (FIG. 1D). These observations demonstrate that miR-181a expression in mature T blast cells augments both the strength and sensitivity of TCR signaling. The effects of miR-181a may be understated in this measurement since the MCC peptide is a strong agonist and may allow little room for further improvement. Indeed, a more dramatic increase in TCR signaling by miR-181a was observed when the miR-181a T cell blasts were challenged with MCC 102S—a weak antigenic peptide (FIG. 1E), showing that miR-181a expression potentiates the strength of TCR signal responses and quantitatively augments T cell sensitivity to both weak and strong agonist peptides.

Figure 2C:
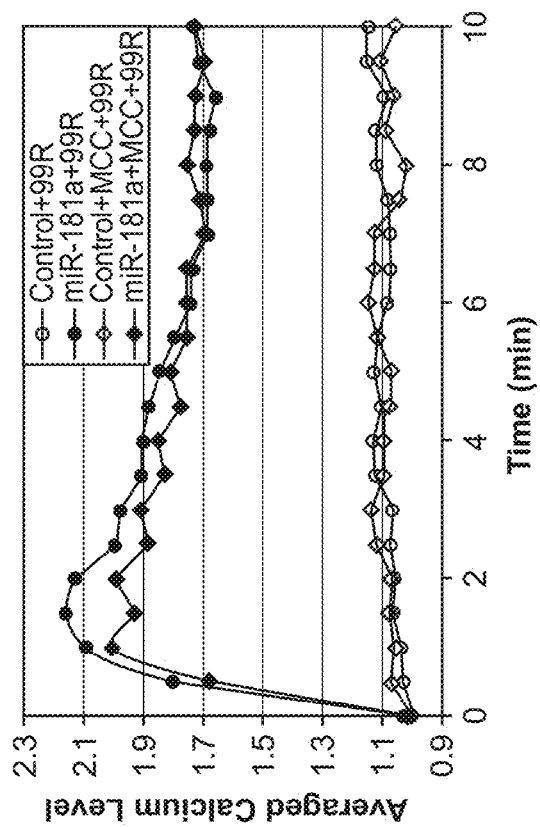

MiR-181a Converts Antagonists into Agonists. In addition to these quantitative changes in T cell sensitivity, we also explored whether miR-181a could alter antigen discrimination and allow T cells to respond to antagonists, which are antigenic peptide variants that are unable to stimulate TCR responses by themselves but block T cell activation when they are presented together with a normally stimulatory concentration of agonist. Under a standard test condition, when the antagonist MCC 99R is present in large excess to the agonist MCC, TCR signaling is blocked in control T cell blasts, where no calcium influx was detected (FIG. 2A). Interestingly, under the same conditions, MCC 99R cannot block the activation of the miR-181a T cell blasts, demonstrating that miR-181a overrides TCR antagonism (FIG. 2A). Since we have shown that miR-181a expression in T cell blasts can augment the TCR response to agonists (FIG. 1), it was possible that this reversal of the antagonist function simply is the result of increased TCR responses to the agonist beyond the ability of antagonist to block. However, when T cells were challenged with antagonist alone, we found that the antagonist MCC 99R can stimulate a calcium response in miR-181a T cell blasts, demonstrating that miR-181a expression enables T cells to recognize MCC 99R as an agonist (FIG. 2B). MCC 99R stimulation resulted in a more than two-fold increase in the peak cytosolic calcium response and sustained calcium elevation for more than 10 minutes, indicating that the antagonist induces a full-scale calcium response in these cells (FIG. 2C).

Figure 2F:
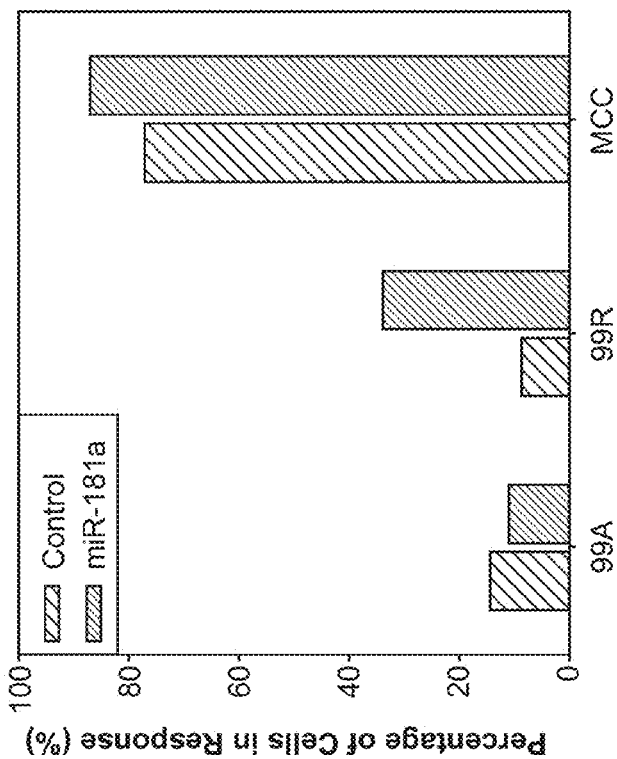
Figure 2E:
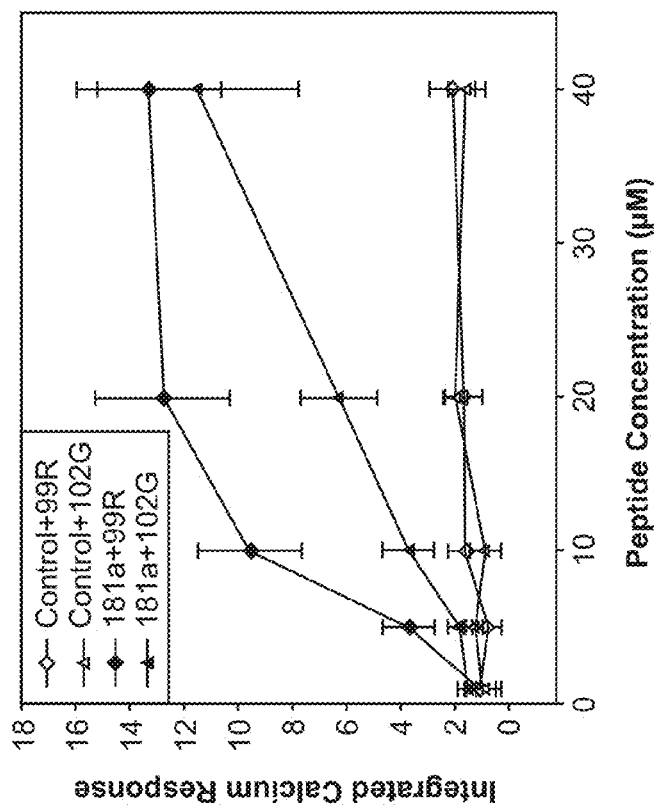

To further determine whether miR-181a expression converts antagonist MCC 99R into a full agonist, we examined whether MCC 99R can stimulate IL-2 production and T cell proliferation. In the miR-181a T cell blasts, MCC 99R is able to stimulate production of the cytokine IL-2 (FIG. 2D) as well as T cell proliferation (FIG. 2E), although somewhat weaker than the responses generated by MCC peptide in control cells. Moreover, this dramatic functional switch is not limited to the MCC 99R antagonist. Similar results are seen with another antagonist, MCC 102G (FIG. 2F). Taken together, these results show that ectopic miR-181a expression in T cell blasts not only quantitatively enhances T cell signaling strength and T cell sensitivity to antigens, but it also enables T cell blasts to respond to antagonists.

MiR-181a Represses Multiple Negative Regulators in the TCR Signaling Pathway. To understand how miR-181a influences T cell reactivity to antigens, we first examined whether miR-181a regulates the expression of TCR or other surface molecules that are known to play important roles in TCR signaling strength and sensitivity. Interestingly, miR-181a expression in T cell blasts does not change TCR density on the cell surface based on antibody staining and flow cytometry analysis (FIG. 13A). Furthermore, miR-181a expression in T cell blasts causes no discernable difference in surface CD4 expression (FIG. 13A), thus eliminating the possibility that miR-181a augments T cell sensitivity by altering CD4 coreceptor expression.

Interestingly, we did detect an increase in the costimulatory molecule CD28 and a decrease in its antagonistic partner CTLA-4 on the miR-181a T cell blasts (FIG. 13B). Modulating the expression of costimulatory molecules by miR-181a seems to have a positive effect on TCR signal strength as indicated by sustained calcium flux (FIGS. 13C&D), which may have contributed to the increase in the calcium response plateau observed in FIG. 1D. However, miR-181a T cell blasts can still respond to MCC 99R while CD28 costimulation is inhibited by antibody blockade of CD28 ligands (B7.1 and B7.2) on the APC's surface, indicating that miR181a's effect on costimulation does not contribute to the conversion of antagonists to agonists (FIG. 14).

Thus, these observations suggest that miR-181a is likely to modulate TCR sensitivity to antigens by controlling the intracellular TCR signaling molecules. By challenging T cell clones bearing two distinct TCRs with their respective peptide agonist and antagonist, several studies have shown that antagonists elicit negative signals that can actively repress the agonist-induced responses from the other TCR. The tyrosine phosphatase SHP-1 has been proposed to be the negative feedback regulator triggered by antagonists and the activation of ERK kinases appears to override this suppression. However, our computational analysis does not shown any putative miR-181a binding sites in SHP-1 gene. Furthermore, miR-181a expression in T cell blasts shows no change in SHP-1 expression at either protein (FIG. 3B) or RNA level. Thus, SHP-1 is not a direct target of miR-181a, suggesting that other components of the TCR signaling pathway may contribute to TCR antagonism.

Figure 3A:
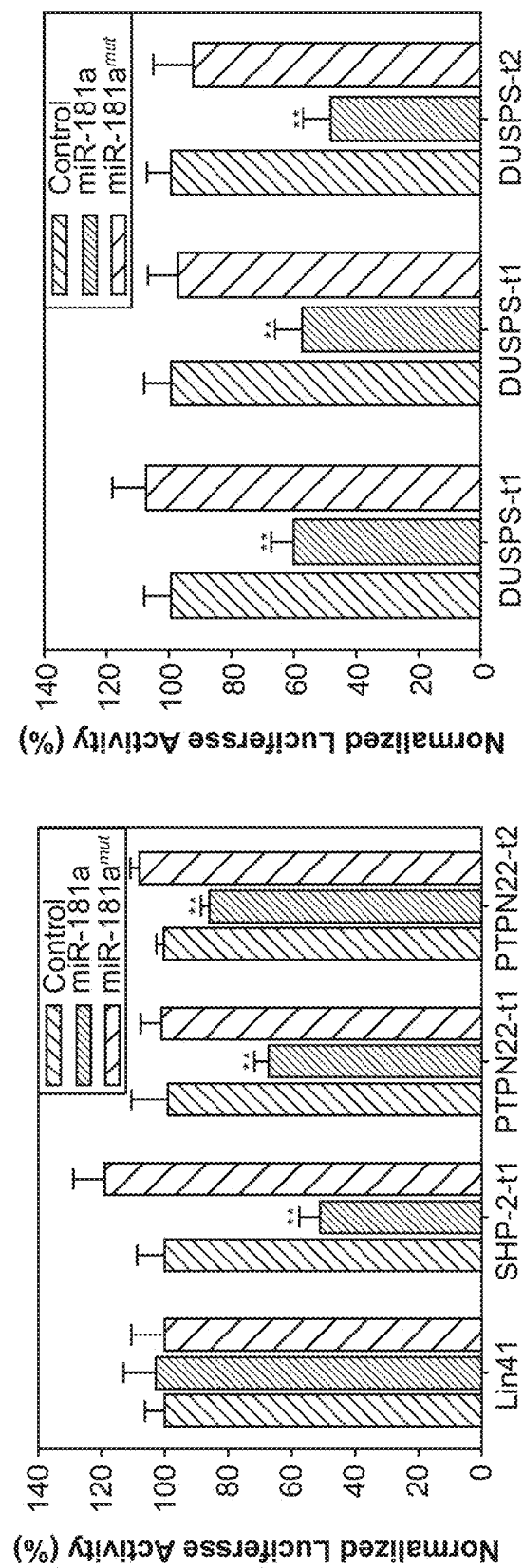
FIGS. 3A-3C MiR-181a represses multiple phosphatases in T cell blasts. (A) Effects of miR-181a and miR-181a$^{mut}$ expression on luciferase reporter constructs containing putative miR-181a target sites are shown as the relative luciferase activity (normalized to the Rennilla control and compared to the control reporter vector). Representative analyses of four independent experiments are shown (relative luciferase activity ±SD, n=3; Student's t test, **: $P<0.01$). (B) MiR-181a regulation of phosphatase expression at the protein level. Western blot analyses were performed to determine the protein levels of SHP-1, SHP-2, PTPN22, DUSP6 and DUSP5 in T cells ectopically expressing either the control virus, miR-181a, or miR-181a$^{mut}$ virus. Membranes were stripped and re-probed with anti-β-actin as a loading control. Relative protein expression levels were determined by densitometry and normalized to the loading controls. (C) Effects of miR-181a on its target messenger RNA levels in T cell blasts were determined by qPCR analyses and indicated as relative expression level (normalized to β-actin and compared to the levels in the control T blast).
Figure 3B:
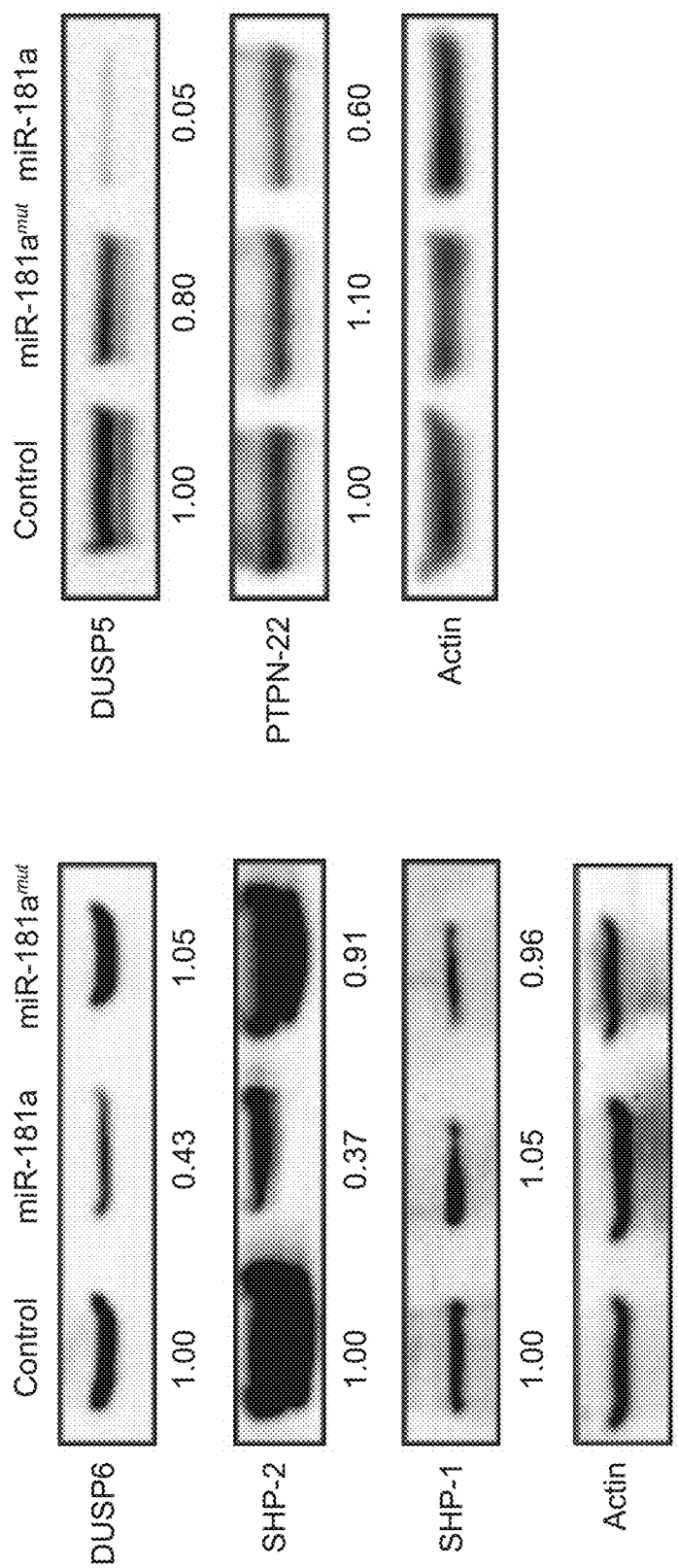
Figure 3C:
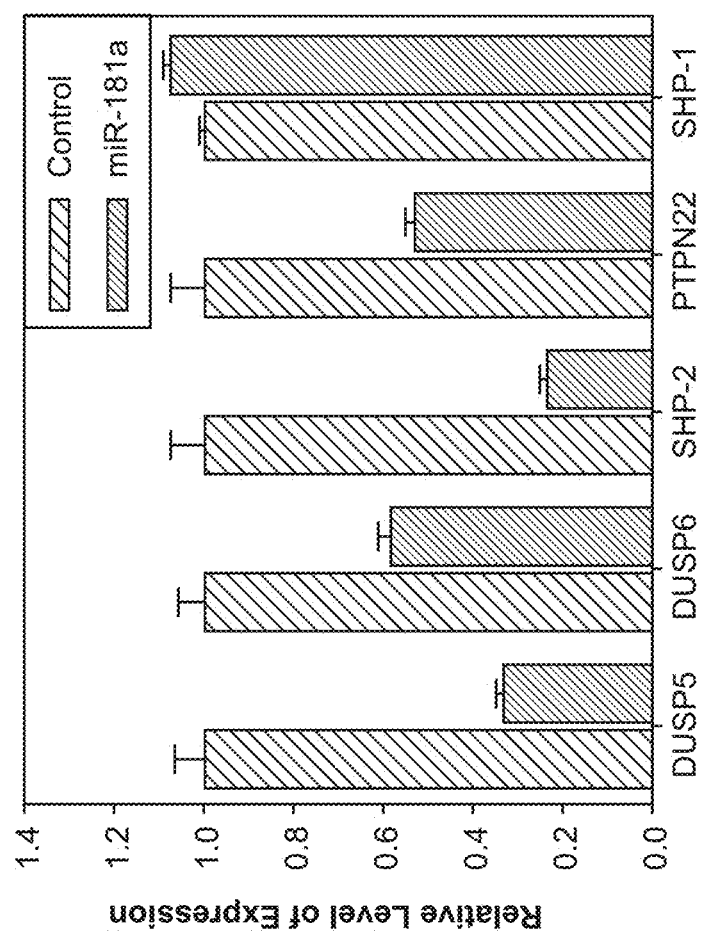

Since a number of tyrosine and serine phosphatases besides SHP-1 have been implicated in the suppression of TCR signaling, we examined potential miR-181a target sites in the phosphatases that are involved in TCR proximal signaling (non-receptor type tyrosine phosphatase, PTPNs) and ERK de-phosphorylation (dual specificity phosphatases, DUSPs). We searched for potential miR-181a pairing sites in both open reading frames (ORFs) and untranslated regions (UTRs) of the candidate genes. We found that the tyrosine phosphatases SHP-2 and PTPN22, and the ERK specific phosphatases DUSP5 and DUSP6 each contain multiple putative miR-181a pairing sites (FIG. 15). Those potential target sites with near perfect seed pairing and/or the lowest free energy of binding were selected for further validation using a luciferase reporter assay (FIG. 15). Fusion luciferase reporters bearing predicted target sequences from SHP-2, PTPN22, DUSP5, or DUSP6, respectively, were specifically repressed by miR-181a (FIG. 3A), but not by an miR 181a mutant with its 5' second and third nucleotides altered (FIG. 3A) or miR-142. Furthermore, Western blot analyses revealed that SHP-2, PTPN22, DUSP5, and DUSP6 protein levels are quantitatively reduced by miR-181a, but not by an miR-181a mutant (FIG. 3B). As indicated by qPCR analyses, the reduction of target protein levels correlates well with the decreases in corresponding messenger RNA levels in the miR-181a T blasts, suggesting that miR-181a can reduce the mRNA levels of the target genes. These results demonstrate that miR-181a directly represses the expression of multiple phosphatases.

Figure 4A:
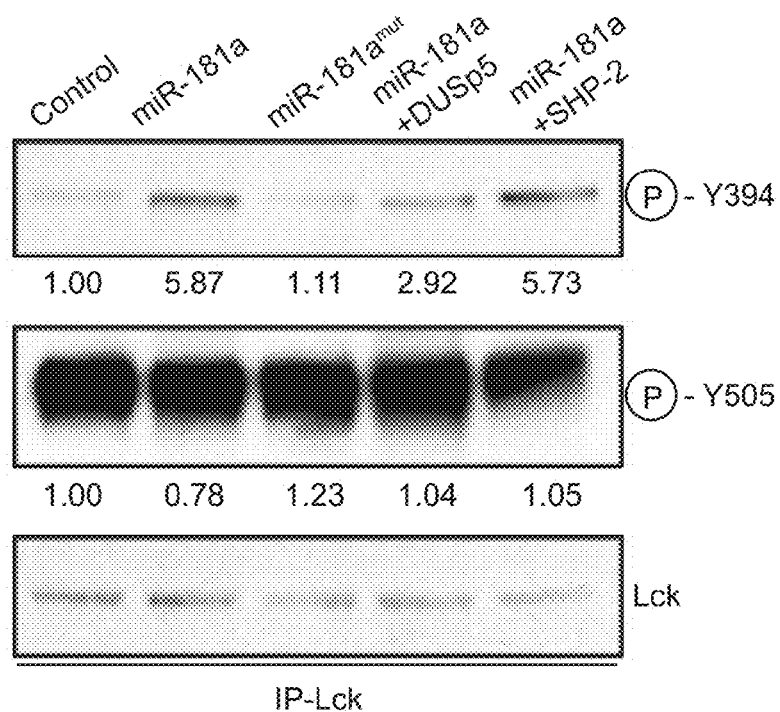
FIGS. 4A-4E MiR-181a increases the basal level phosphorylation of downstream TCR signaling molecules. (A) Western blot analyses of anti-Lck immuno-precipitates to detect site-specific phosphorylation. Phosphorylation of Lck at the activating Y394 or inhibitory Y505 before antigen stimulation were probed with specific antibodies. Lck phosphorylation was also analyzed in the miR-181a T cell blasts with restored DUSP6 or SHP-2 expression. Membranes were stripped and re-probed for Lck as loading controls. (B) Induction of ERK phosphorylation by the antagonist MCC 99R. Virally-infected T cells were mixed with CH27 cells alone or CH27 cells preloaded with 10 μM MCC 99R, spun down to facilitate rapid T:APC contact, incubated at 37° C. for 5 minutes, and analyzed for ERK phosphorylation by Phosphor-Flow. Cells were gated on GFP and CD4 for virally-infected T cells. (C) Effects of miR-181a on the kinetics of ERK phosphorylation upon T cell stimulation by anti-CD3ε cross-linking according to Phospho-Flow analysis. (D) Western blot analyses of anti-Lck immuno-precipitates to detect Lck serine phosphorylation before antigen stimulation. (E) MiR-181a expression inhibits the Lck and SHP-1 interaction. Double selected 5C.C7 T cells were mixed with peptide pre-loaded CH27 cells (10 μM MCC 99R or 1 μM MCC) by quick spin and incubated at 37° C.

MiR-181a Expression Enhances Basal Activation of TCR Signaling Molecules. Down-regulation of these phosphatases is likely to systematically reduce negative feedback regulation since the phosphatases targeted by miR-181a act at distinct steps in the TCR signaling pathway. PTPN22, a potent negative regulator immediately downstream of TCR, can de-phosphorylate Lck and ZAP70 at the activating Y394 and Y493 within the kinase activation loops. A gain-of-function variant of PTPN22 has been shown to reduce T cell sensitivity. Consistent with the role of PTPN22 as a negative regulator of Lck, we found an increase in Y394 phosphorylation in the activation loop of Lck in the miR-181a T cell blasts even before stimulation (FIG. 4A).

Figure 4B:
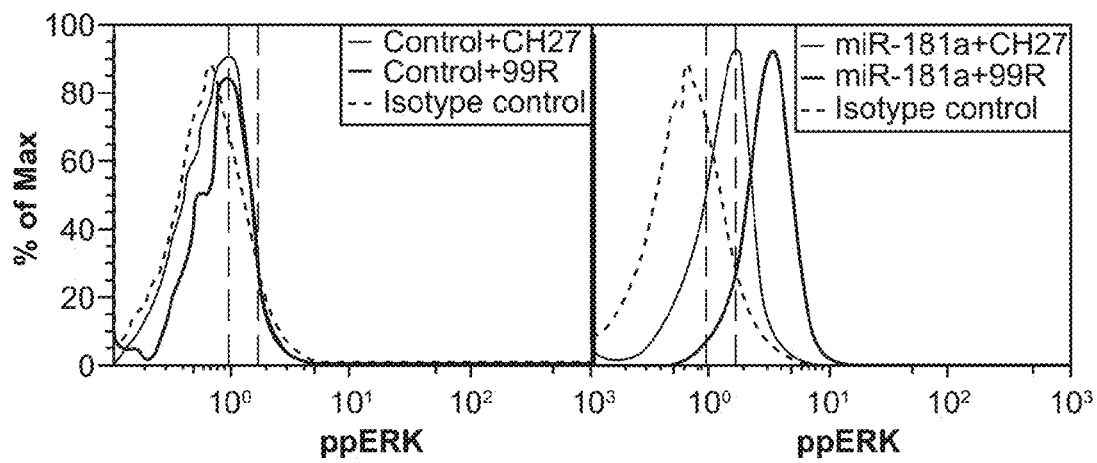
Figure 4C:
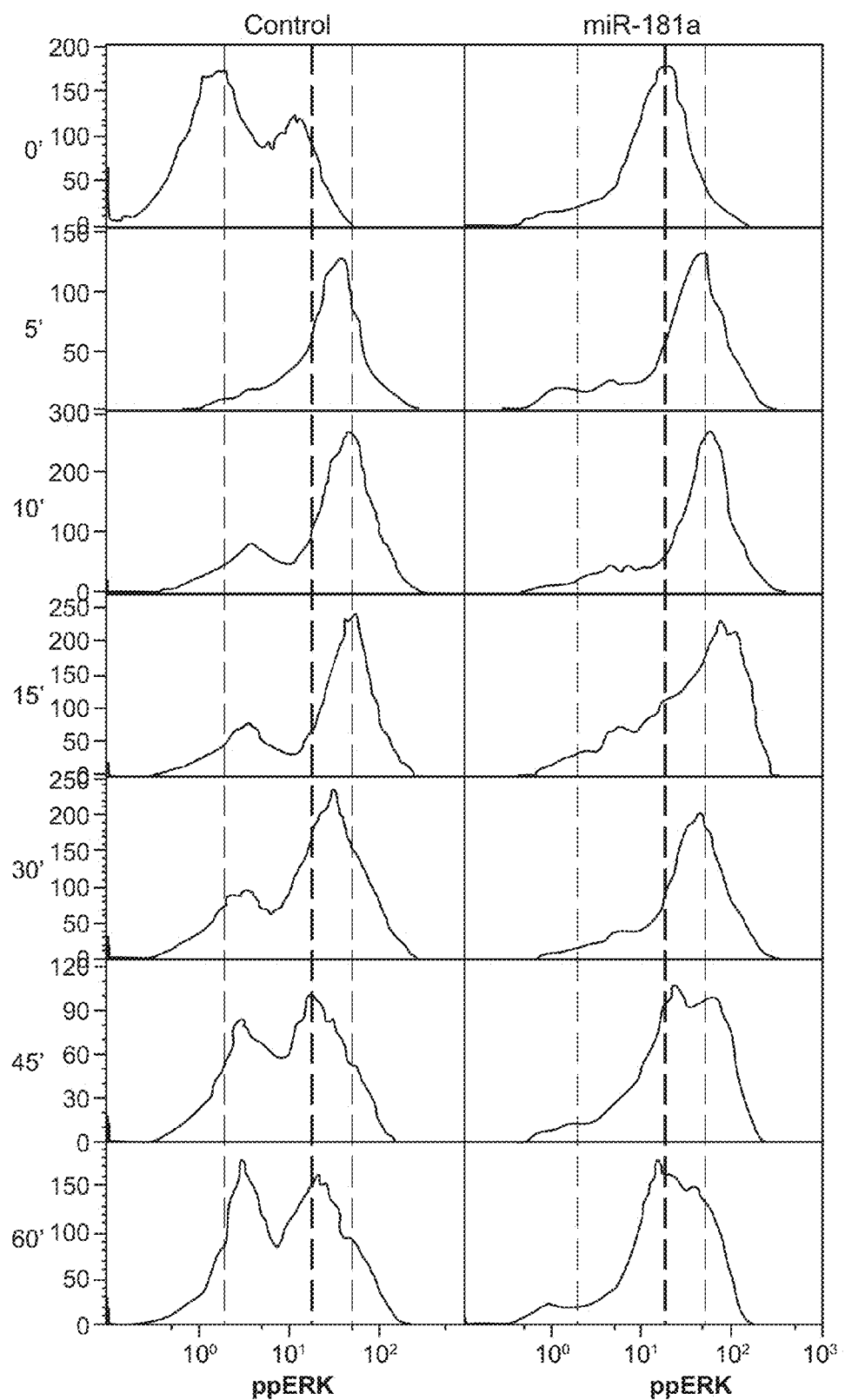
Figure 4D:
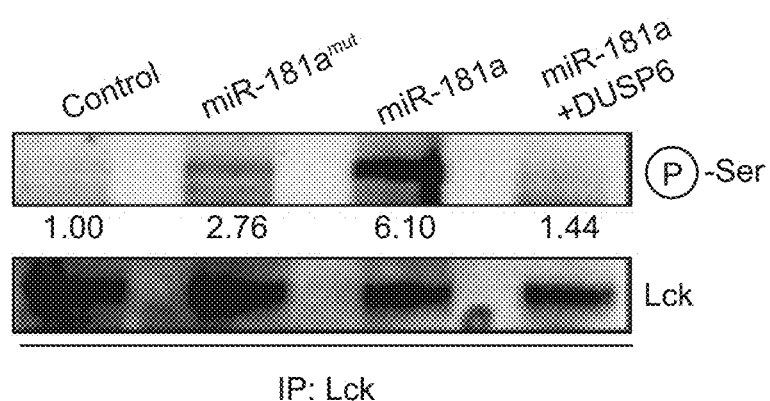
Figure 4E:
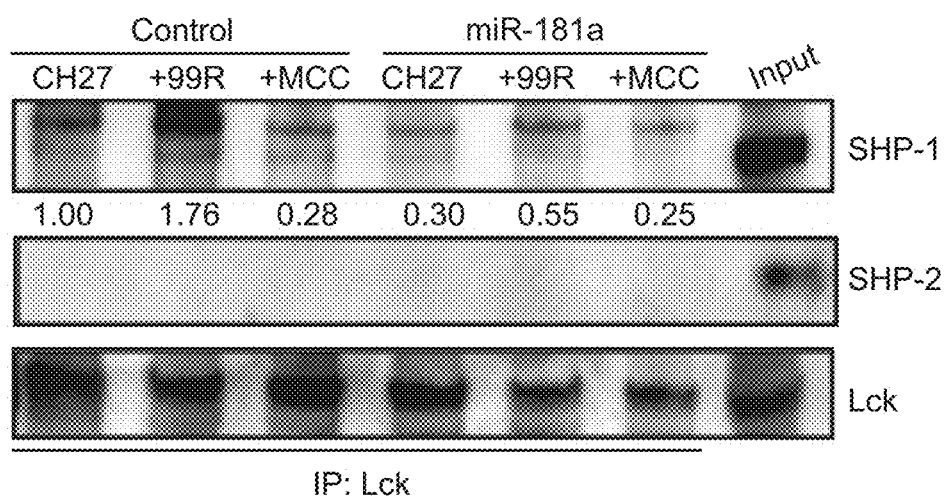

DUSP5 and DUSP6, which are localized in the nucleus and cytosol, respectively, can specifically bind and inactivate ERK1/2 by de-phosphorylating the T202 and Y204 residues in the kinase activation loop. SHP-2 was found to mediate negative costimulatory signals elicited by CTLA-4, but it has not been shown to play direct roles in TCR proximal signaling (FIG. 4E).

To examine how miR-181a may affect ERK1/2 activation, we measured the ERK1/2 phosphorylation level before and after MCC 99R antagonist stimulation using intracellular antibody staining and FACS analysis. T cell blasts were fixed at various time points after stimulation, stained with antibodies against the T202 and Y204 phospho-epitopes of the ERK1/2 kinases, and analyzed by FACS to determine the ERK phosphorylation level. The miR-181a T cell blasts have a significantly higher level of T202 and Y204 phosphorylated ERK proteins prior to stimulation (FIG. 4B blue lines). Interestingly, the antagonist MCC 99R can stimulate ERK phosphorylation in miR-181a transfected T cell blasts or endogenously highly expressed DP thymocytes, but not in control T cell blasts (FIG. 4B orange lines).

Furthermore, we examined whether miR-181a may alter the kinetics of ERK1/2 phosphorylation during T cell activation. T cell blasts were activated by CD3ε cross-linking to avoid any contribution from costimulatory pathways. We noted that the miR-181a T cell blasts have a significantly higher basal level of ERK phosphorylation before stimulation and a slightly higher peak level after stimulation (FIG. 4C). While both the control and miR-181a T cell blasts reached maximal ERK phosphorylation within 15 minutes after stimulation, a delay in ERK dephosphorylation was observed in the miR-181a T cell blasts. More importantly, the phosphorylation level of these cells returns to a higher basal level when compared to controls (FIG. 4C, time points 15-60 minutes). These data demonstrate that ERK phosphorylation is shifted to a higher basal level both before and after stimulation, suggesting that miR-181a induces decreases in phosphatase expression and acts to shift the equilibrium to higher steadystate levels of phospho-ERK. This increased basal level of ERK phosphorylation has additional effects in potentiating TCR proximal signaling. This is indicated by dramatic increases in serine phosphorylation of Lck in miR-181a transduced cells. Co-expression of miR-181a and a DUSP6 gene without the miR-181a target sites in T cell blasts restores DUSP6 expression to the normal level and reduces the basal Lck serine phosphorylation to the background levels, suggesting that the downregulation of DUSP6 is directly responsible for the increase in Lck serine phosphorylation.

While there are four major serine phosphorylation sites in Lck, activated ERK is responsible for Ser-59 phosphorylation under physiological conditions. Previously, Germain and colleagues have proposed that the positive feedback from ERK is crucial for agonist ligands to overcome SHP-1 blockage and have shown that Ser-59 phosphorylation of Lck can block SHP-1 recruitment. In agreement with this observation, we noted a dramatic reduction in the recruitment of SHP-1 to Lck before and after antagonist stimulation in miR-181a T cell blasts (FIG. 4E). It is also notable that restoring DUSP6 expression in these cells results in a decrease in the basal level of Y394 phosphorylation on Lck, suggesting that blocking SHP-1 recruitment to Lck may also contribute to the increased basal level of this phosphotyrosine. These observations suggest an alternative mechanism in which antagonist-induced SHP-1 negative feedback can be overcome or reduced despite the fact that SHP-1 is not directly targeted by miR-181a. Collectively, it seems that the increased basal-level of Lck and ERK activation in the miR-181a T cell blasts reduces the amount of signal that is required for achieving full Lck and ERK activation upon antigen stimulation, thus reducing the activation threshold and increasing signaling strength and T cell sensitivity to weak agonists and antagonists (FIG. 8).

Furthermore, we examined whether miR-181a may alter the kinetics of ERK1/2 phosphorylation during T cell activation. T cell blasts were activated by CD3ε cross-linking to avoid any contribution from costimulatory pathways. We noted that the miR-181a T cell blasts have a significantly higher basal level of ERK phosphorylation before stimulation and a slightly higher peak level after stimulation (FIG. 4B). While both the control and miR-181a T cell blasts reached maximal ERK phosphorylation within 15 minutes after stimulation, a delay in ERK dephosphorylation was observed in the miR-181a T cell blasts. More importantly, the phosphorylation level of these cells returns to a higher basal level when compared to controls (FIG. 4C, time points 15-60 minutes). These data demonstrate that ERK phosphorylation is shifted to a higher basal level both before and after stimulation, suggesting that miR-181a induced decreases in phosphatase expression and activity shift the equilibrium to higher steadystate levels of phospho-ERK. This increased basal level of ERK phosphorylation has additional effects in potentiating TCR proximal signaling. This is indicated by dramatic increases in serine phosphorylation of Lck in miR-181a transduced cells (FIG. 4D). Co-expression of miR-181a and a DUSP6 gene without the miR-181a target sites in T cell blasts restores DUSP6 expression to the normal level (FIG. 6A) and reduces the basal Lck serine phosphorylation to the background levels (FIG. 4D), suggesting that the down-regulation of DUSP6 is directly responsible for the increase in Lck serine phosphorylation. While there are four major serine phosphorylation sites in Lck, activated ERK is responsible for Ser-59 phosphorylation under physiological conditions.

We noted a dramatic reduction in the recruitment of SHP-1 to Lck before and after antagonist stimulation in miR-181a T cell blasts (FIG. 4E). It is also notable that restoring DUSP6 expression in these cells results in a decrease in the basal level of Y394 phosphorylation on Lck, suggesting that blocking SHP-1 recruitment to Lck may also contribute to the increased basal level of this phosphotyrosine (FIG. 4A). These observations suggest an alternative mechanism in which antagonist-induced SHP-1 negative feedback can be overcome or reduced despite the fact that SHP-1 is not directly targeted by miR-181a. Collectively, it seems that the increased basal-level of Lck and ERK activation in the miR-181a T cell blasts reduces the amount of signal that is required for achieving full Lck and ERK activation upon antigen stimulation, thus reducing the activation threshold and increasing signaling strength and T cell sensitivity to weak agonists and antagonists.

Multi-Target Regulation by miR-181a is Crucial for miR-181a Function. To determine whether one or all of the phosphatases regulated by miR-181a are functionally relevant for its conversion of antagonists into agonists, we designed short hairpin siRNAs (shRNAs) to selectively 'knockdown' SHP-1, SHP-2, DUSP5 and DUSP6 mRNA expression. Three shRNA constructs were designed for each target gene and their efficacy in silencing their respective targets was validated by Western blot analyses (FIG. 5A). In each case, we were able to obtain shRNA constructs that can repress target gene expression more efficiently than miR-181a (FIGS. 3B&5A). We then expressed individual shRNAs in T cell blasts by viral transduction, isolated the infected cells to 90-95% purity by drug selection and magnetic bead selection, and challenged the infected T cell blasts with APCs preloaded with MCC 99R (10 μM). We determined the calcium response and then categorized the signal strength using the typical response of control T cells towards the MCC peptide as a reference. As shown in FIG. 5B, over 90% of the miR-181a T cell blasts yielded medium to strong responses when stimulated with MCC 99R, whereas less than 10% of the T cell blasts infected with shRNAs against SHP-2, control shRNAs (FIG. 5B), and control virus yielded similar responses, which represents the background levels. We noticed that shRNAs against SHP-1 and DUSP6 do have modest effects, and about 25% and 38% of the T cell blasts expressing shRNA against DUSP6 or SHP-1 yielded medium to strong responses. However, both the peak values and the degree to which calcium signaling is sustained are reduced even in these reactive T cells when compared to the response in the miR-181a T cell blasts.

Taken together, these data demonstrate that repressing individual phosphatases by shRNA is not sufficient to fully reproduce miR-181a phenotype in T cell blasts and miR-181a is much more efficient than individual shRNAs since it can down-regulate the expression of multiple phosphatases.

Figure 6A:
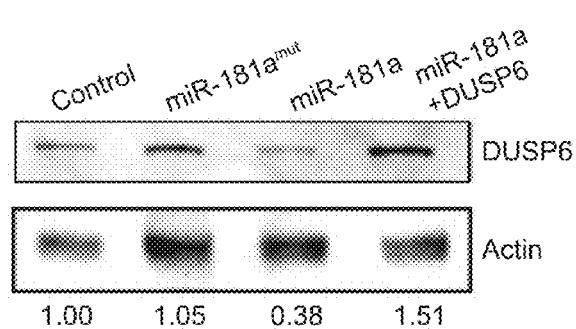
Figure 6B:
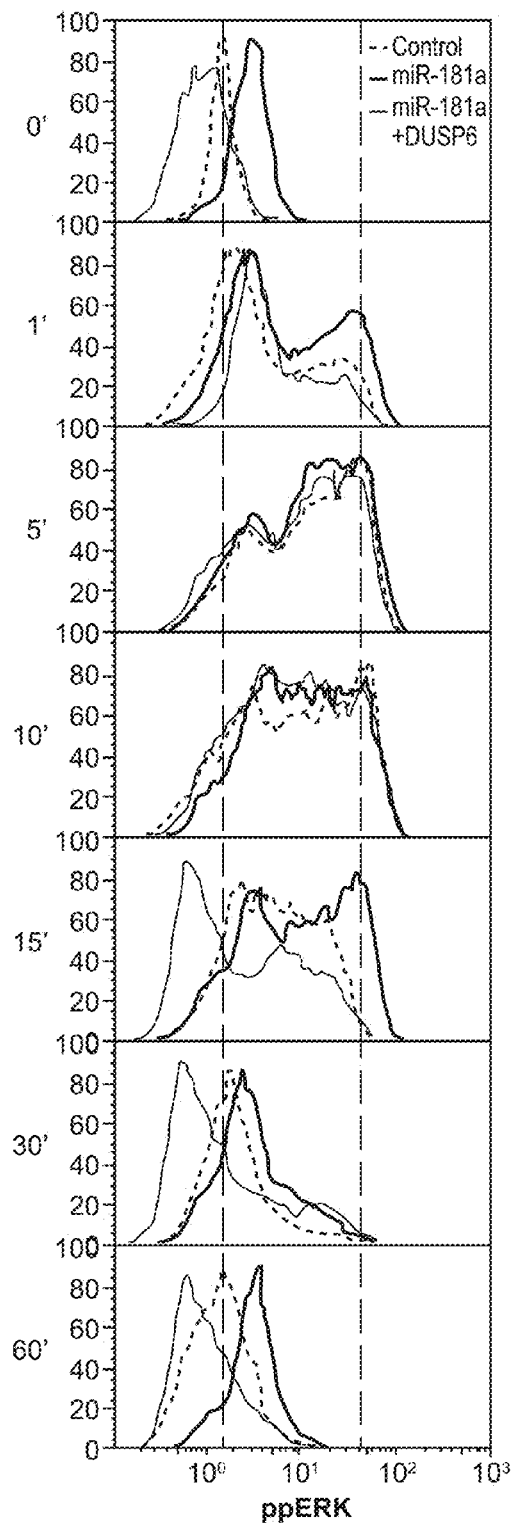
Figure 6C:
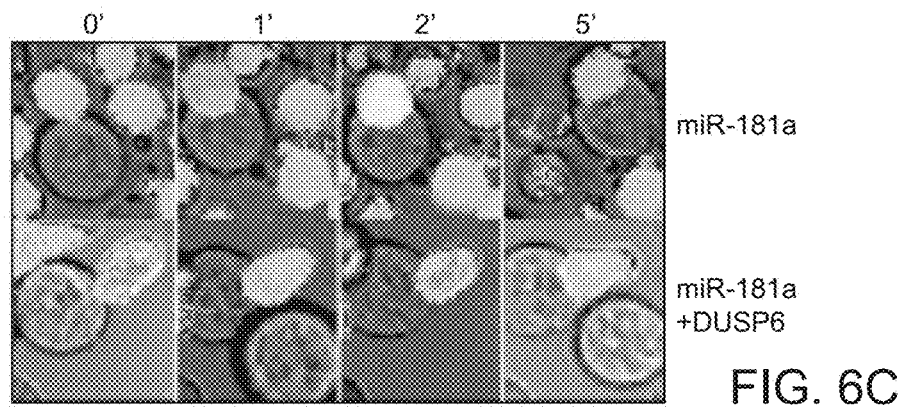
Figure 6D:
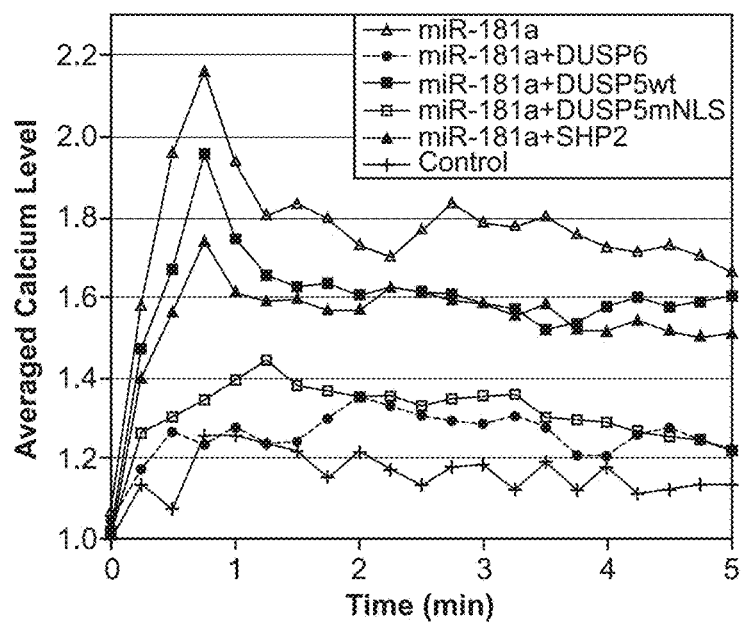
Figure 6E:
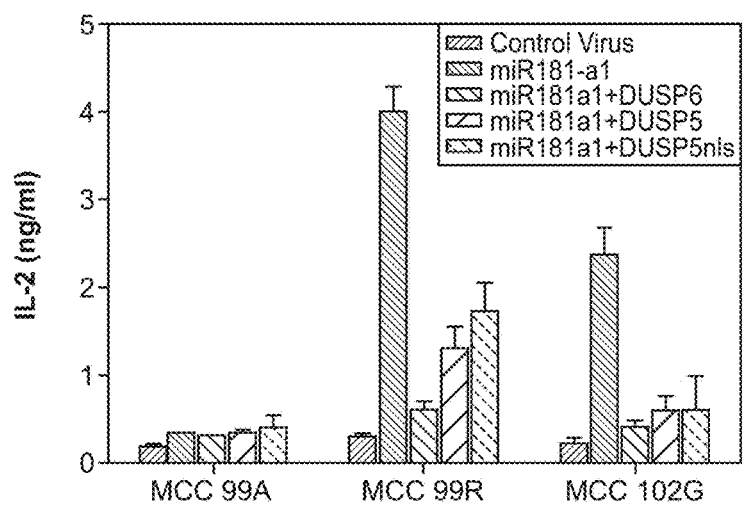

To evaluate whether down-regulation of individual miR-181a targets is necessary for the increase in T cell sensitivity to antagonists, we restored the DUSP6 expression to normal levels in the miR-181a T cell blasts by co-expressing a DUSP6 gene that lacks the miR-181a target sites (FIG. 6A). This resulted in a reduction in the basal level of phospho-ERK, time point zero) and accelerated ERK dephosphorylation/inactivation as indicated by Phospho-Flow analysis (FIG. 6B, time points 10-60 mins). Most importantly, restoring DUSP6 expression in this way completely abolishes the T cell reactivity to MCC 99R (FIG. 6C, D, E). Similarly, restoring DUSP5 expression in the nucleus results in a dramatic reduction in the IL-2 production induced by the MCC 99R antagonist, while it has little effect on cytosolic calcium responses (FIGS. 6D&E), suggesting that wild type DUSP5 acts as a negative regulator controlling IL-2 production in the nucleus with little impact on the immediate TCR signaling. Interestingly, expressing and sequestering DUSP5 protein in the cytosol by nuclear localization signal mutation can largely resemble the TCR sensitivity shift caused by DUSP6 restoring (FIGS. 6D&E). These evidences collectively suggest that the cytosolic level of ERK activation is crucial for the initial TCR signaling upon antigen recognition. In contrast, restoring SHP-2 does not change the basal level of Lck activation (FIG. 6A) or suppress the recognition of MCC 99R, although it does cause a modest reduction in TCR signaling strength (FIG. 6D), suggesting that SHP-2 plays a minor role in antigen discrimination. These results suggest that DUSP6, but not SHP-2, is one of the key players in the negative regulation of TCR signaling.

Inhibition of miR-181a in Thymocytes Impairs Positive and Negative Selection. Our results clearly demonstrate that increasing miR-181a expression induces hypersensitivity in T cells (FIGS. 1&2), while inhibition of this miRNA dampens their sensitivity to antigens (FIG. 7). Interestingly, miR-181a expression is dynamically regulated during T cell development, with immature DP cells having ~10-fold more copies of miR-181a than their mature counterparts (FIG. 1A). Enhanced expression correlates with heightened sensitivity towards pMHC ligands in DP cells, which is thought to be critical in ensuring proper positive and negative selection, and shaping of the mature T cell repertoire. Consequently, we tested miR-181a function in DP cell selection using fetal thymic organ cultures (FTOC) with an antagomir based loss-of-function approach.

Figures 8A, 8B:
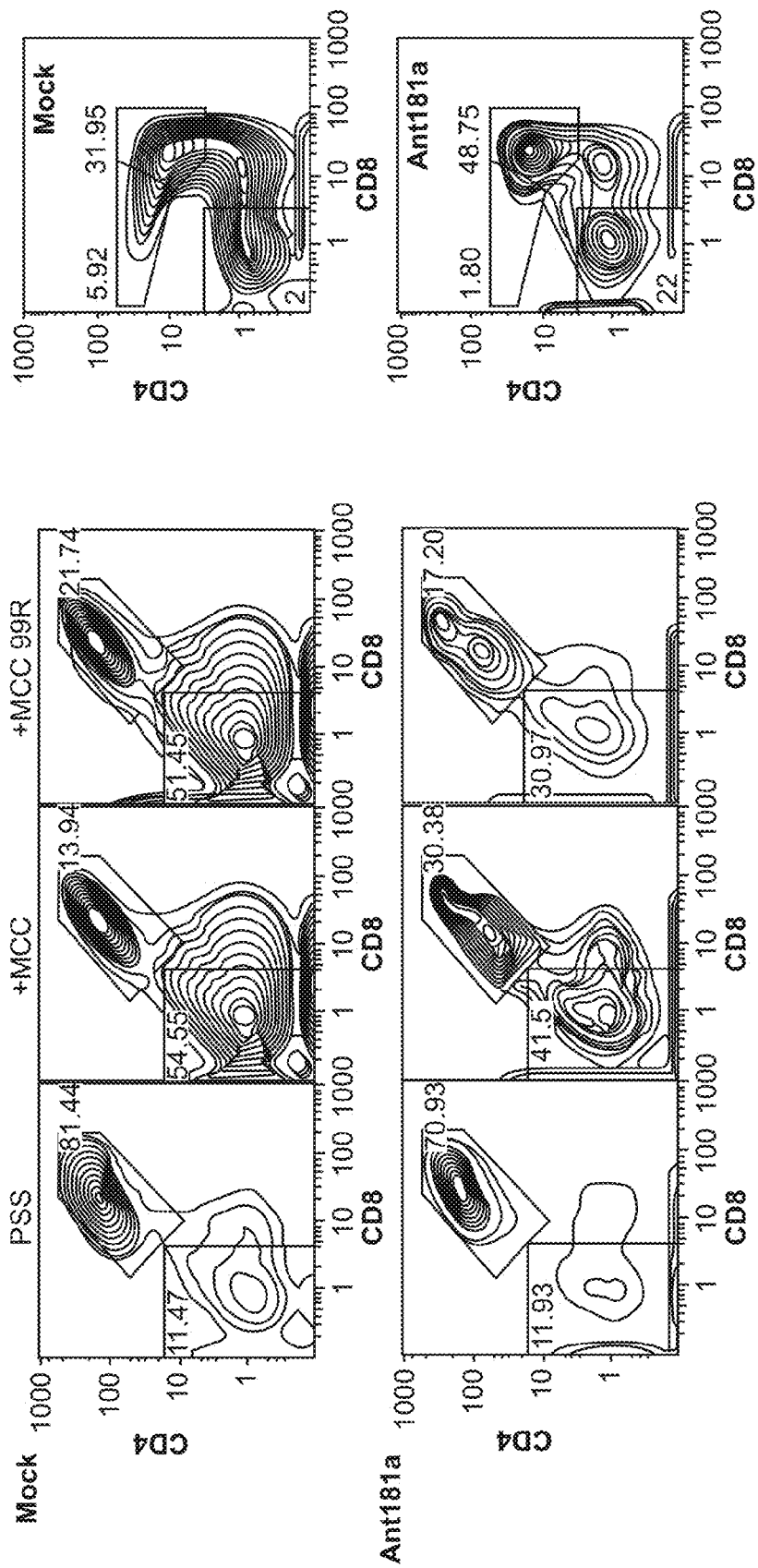

We crossed 5C.C7 TCR transgenic mice onto an invariant chain knockout (Ii−/−) background to arrest thymocytes at the DP stage. Although a moderate increase in the DN cell population was observed, antagomir-181a treatment did not affect the viability of DP thymocytes in this culture system (FIG. 8A). Presenting exogenous 5C.C7 TCR antigens, such as agonist (MCC), weak agonist (MCC 102S) or antagonist (MCC 99R), can induce efficient negative selection within 48 hours. Introducing antagomir-181a to these cultures results in a greater than 2-fold inhibition of negative selection (FIG. 8A). To examine the role of miR-181a in positive selection, day 15 fetal thymi from wild type 5C.C7 embryos were used in this FTOC assay. These mice have normal invariant chain production and are capable of presenting endogenous peptide antigens, thus allowing positive selection. Dampening miR-181a expression with the antagomir- 181a reagent substantially impairs positive selection, reducing the number of mature CD4+SP thymocyte by ~3-fold (FIG. 8B).

Figure 8C:
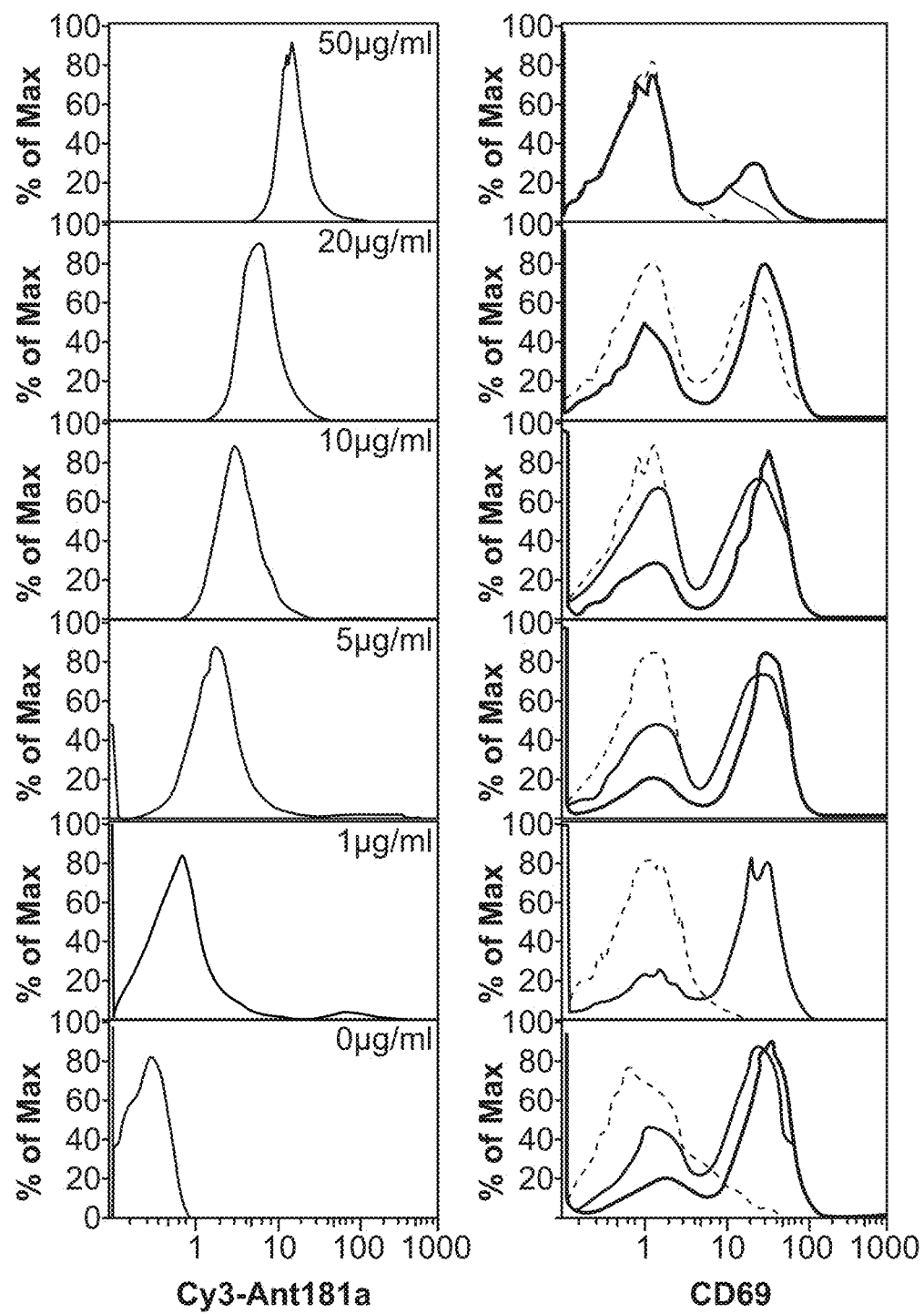
Figure 8D:
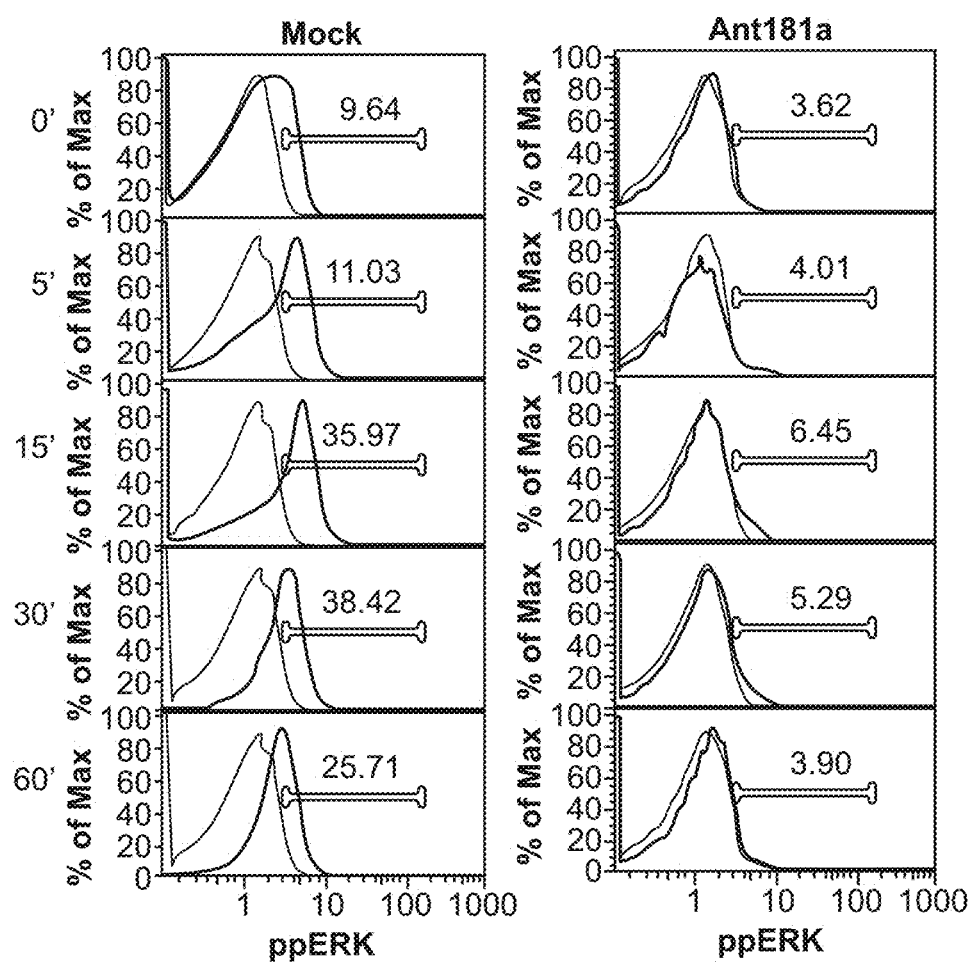

Does this inhibition of selection correlate with a deficiency in TCR signaling? We verified this by observing the response of adult 5C.C7 DP thymocytes to in vitro antigen stimulation. In the presence of antagomir-181a pretreatment, the responsiveness of these cells is dramatically diminished in a dose-dependent manner (FIG. 8C). Is this antagomir-181a induced hyposensitivity related to the same molecular mechanism described for mature T cells? All MiR-181a targeted phosphatases are expressed in DP thymocytes and antagomir-181a treatment elevates their mRNA level significantly. Coordinately, we observed a severe reduction of ERK activation in these antagomir-181a treated DP thymocytes both in basal level of ERK phosphorylation (FIG. 8D, time zero) and antigen-induced ERK phosphorylation (FIG. 8D, time 5' to 60'). Collectively, these results demonstrate that antagomir-mediated reduction of miR-181a expression in immature DP thymocytes attenuates their sensitivity to antigen and inhibits positive and negative selection. Thus miR-181a is an intrinsic modulator of TCR sensitivity during T cell development and differentiation.

Dampening Mature T Cell Sensitivity by miR-181a Inhibition. The above results clearly show that that increasing miR-181a level in T cell blasts by ectopic expression dampens the expression of multiple phosphatases in the TCR signalling pathway, reduces the TCR signalling threshold, and results higher T cell sensitivity to antigens. To test whether miR-181a may act as a 'rheostat' to tune T cell sensitivity, we examined effects of decreasing miR-181a expression on T cell sensitivity to antigens.

Antagomirs—antisense oligos that silence miRNA expression in vivo—were used to reduce miR-181a expression in T cells. We transfected either naïve T cells or mature blasts with an antagomir that targets miR-181a (antagomir-181a) and challenged antagomir treated cells with CH27 APCs loaded with MCC or MCC 102S at various concentrations. We then measured the calcium response by video microscopy (FIG. 7A) and IL-2 production by ELISA (FIG. 7B) to determine the effects of antagomirs on T cell sensitivity to antigens. An antagomir-181 mutant (Mm-antagomir-181a) with a 6 nucleotide mismatch to the 5' seed region of miR-181a was used as a negative control. All antagomirs have a Cy3 label at the 5'-end which allows their transfection efficiencies to be monitored by FACS. We were able to achieve near 100% transfection efficiency and similar intensities for each oligo under the designated experimental conditions. We find that reducing miR-181a expression by antagomir treatment significantly lowers naïve T cell sensitivity to the agonist MCC and the weaker agonist MCC 102S, as indicated by calcium flux and IL-2 production (FIGS. 7A&B). Antagomir-181a also inhibits the increased surface expression of CD69 and CD5—two early T cell activation markers—upon antigen stimulation.

In contrast, the control antagomir has no effects on T cell sensitivity to antigens (FIGS. 7 A&B), showing that the effects of antagomir-181a are specific. Furthermore, reducing miR-181a expression also reduces T cell sensitivity to antigens in the mature T cell blasts, albeit to a lesser degree than that in the naïve T cells. The smaller reduction in antigen sensitivity in mature T cell blasts is probably because that miR-181a level in the mature T cell blasts (10 copies/cell) is much lower than that in the naïve T cells (over 30 copies/cell) (FIG. 1A). Finally, maximum response towards agonist MCC can be induced at a loading concentration close to Kd in naïve T cells (FIG. 7A), while much higher concentrations are required to elicit the maximal responses in mature T cell blasts (FIG. 18B), suggesting that naïve T cells are more sensitive to antigens. Collectively, these results demonstrate that tuning down miR-181a expression in naïve and mature T cells by antagomir-181a reduces T cell sensitivity to antigens and miR-181a expression levels may positively correlate with T cell sensitivity.

Our studies demonstrate that TCR signaling strength and T cell sensitivity to antigens can be modulated at the post-transcriptional level by miR-181a. Further dissecting the targets regulated by miR-181a has revealed that this change in T cell sensitivity requires the simultaneous down-regulation of multiple negative regulators in the TCR signaling pathway. Increasing miR-181a expression in T cell blasts results in decreased phosphatase levels, which leads to an increase in the amount of activated Lck and ERK kinases without antigenic stimulation and a reduction in the threshold required for T cell activation. By reducing negative feedback mechanisms and potentiating positive ones, T cells now exhibit quantitatively and qualitatively different responses to antigen stimulation. These findings have a number of implications for the regulation of the adaptive immune response and the biology of miRNAs. In particular, these data suggest that miR-181a is a T cell sensitivity rheostat. It is known that the same antigenic peptides elicit distinct TCR signals and T cell responses in T cell populations at different developmental stages, suggesting that T cell sensitivity to antigens is intrinsically regulated. Properly tuning T cell sensitivity at various development stages may be critical for regulating the development of tolerance and effector cell function. Interestingly, miR-181a expression is higher in some immature T cell populations that recognize low affinity selfantigens, such as DP thymocytes, but low in the more differentiated T cell populations that are only reactive to high affinity foreign antigens and inert to low affinity self-antigens, such as Th1 and Th2 effector cells (FIG. 1A).

These observations reveal a positive correlation between miR-181a expression and the T cell sensitivity to antigens, thus supporting the notion that miR-181a may act as a rheostat to tune T cell sensitivity during T cell development and maturation, since many of the miR-181a targets we identified are known to be functional components of TCR signaling pathways in various T cell populations. These results demonstrate that miRNAs represent a novel class of gene regulatory molecules that can modulate T cell sensitivity.

Our findings provide new insights into the signaling pathways that determine how TCRs sense quantitative differences in antigen affinity and elicit quantitatively and qualitatively different responses and also how such responses may be intrinsically tuned. These observations suggest that the TCR and its proximal signaling molecules act as a "signal integrator" to sum up the positive and negative signals elicited by antigen stimulation, thus determining the outcome of TCR engagement. It is known that in general, longer half-life pMHC ligands elicit stronger positive signals. We have found that the negative feedback signals in this pathway, controlled in part by multiple phosphatases downstream of TCR, play a key role in regulating TCR signaling and antigen discrimination, suggesting that they set the "excitation threshold" for T cell activation and this "excitation threshold" is likely to be dominant. Supporting this, T cell blasts normally cannot be activated by antagonist pMHCs (FIGS. 2 & 4), suggesting that these ligands cannot generate a sufficient degree of positive signals to overcome the "excitation threshold." However, when the equilibrium is shifted towards a higher steady state of phosphorylated signaling intermediates (ERK1/2, Lck as shown above) by ectopically expressing miR-181a in the T cell blasts (FIGS. 2 & 4), these ligands are now stimulatory and weak agonists are now strongly stimulatory.

One would also predict that dampening these negative signals should lead to an increase in TCR signaling strength, since the degree of positive signaling required for overcoming the "excitation threshold" is also reduced. Indeed, we have shown that antagonist MCC 99R, or weak agonist 102S, or agonist MCC I-Ek complexes have increased signaling strength in the miR-181a T cell blasts, as measured by calcium influx, albeit at quantitatively different levels (FIGS. 1 & 2). Our findings also suggest two venues that can be used to overcome this "excitation threshold" and to activate T cells. One is by reducing the "excitation threshold" such that it can be overcome by the otherwise insufficient positive signals generated from the same antigens. Alternatively, weak positive TCR signals can be potentiated so that the "excitation threshold" can be overcome. Finally, our finding that antagonists can be converted into agonists demonstrates that even antagonists can bind to the TCR long enough to complete the entire TCR signaling cascade when the "excitation threshold" is reduced. Interestingly, endogenous peptide-MHC complexes that are known to synergize with agonist ligands still are not stimulatory to miR-181a transfected T cell blasts (FIG. 2D, E). The affinities and half-lives of these ligands for 5C.C7 TCR are not known, but they are probably considerably less stable than the antagonist ligands.

Many biological processes are controlled at the system level by coordinated regulation of networks of genes. Specifically, TCR signaling and antigen recognition are controlled by sequential phosphorylation and de-phosphorylation events in a spatially and temporally ordered manner. T cells express more than 40 different tyrosine phosphatases and other known or unknown negative regulators of TCR signalling. There are multiple phosphatases for each of the key kinases, such as Lck, ZAP70, ERK, etc. Tuning a T cell's "excitation threshold" presents a particular challenge because of the many signaling molecules that seem to constitute the threshold. It may require the coordinate regulation of multiple negative regulators which share little or no sequence homology. Our findings clearly demonstrate that this task can be carried out very efficiently by a single miRNA, which can regulate multiple target genes, but not by a shRNA, which is designed to target one of the miRNA targets. This is consistent with the notion that each miRNA can regulate hundreds of target genes. Collectively, our findings suggest that miRNAs are evolutionarily selected gene regulatory molecules that can carry out integrated biological functions by regulating gene networks.

Materials and Methods

Mice, Cells and Peptides. 5C.C7 αβ TCR transgenic mice on the B10.BR background were obtained from Taconic. 5C.C7 li$^{-/-}$ mice were obtained by crossing 5C.C7 onto li$^{-/-}$ B10.BR mice. All mice were bred and maintained at the Stanford University Department of Comparative Medicine Animal Facility in accordance with National Institutes of Health guidelines. T cells were harvested from the lymph nodes of 5C.C7 mice and primed with 10 μM MCC peptide. A day after priming, T cells were transduced with retroviral miRNA expressing constructs. Infected T cell blasts were first subjected to blasticidin (12.5 μg/ml, Invitrogen) selection for two days starting at 36-hour post-infection, further enriched by density gradient centrifugation with Histopaque-1119 (Sigma-Aldrich), and finally purified based on H-2K$^b$ expression of the infected T cell blasts by magnetic bead sorting according to the manufacturer's protocol (Biotinylated anti-H-2K$^b$, 10 μg/ml, BD Pharmingen; CELLection biotin binder kit, Dynal Biotech). With this procedure, infected T cell blasts were enriched to at least 95% purity based on FACS analyses. Antigenic peptide variants used in this study were the agonist MCC SEQ ID NO:31 (ANERADLIAYLKQATK), weak agonist MCC 102S SEQ ID NO:32 (ANERADLIAYLKQA$\underline{S}$K), antagonist MCC 99R SEQ ID NO:33 (ANERADLIAYL$\underline{R}$QATK) and MCC 102G SEQ ID NO:34 (ANERADLIAYLKQA$\underline{G}$K), and null peptide MCC 99A SEQ ID NO:35 (ANERADLIAYL$\underline{A}$QATK). Variations in residues are underlined. Peptide-loaded CH27 cells, a mouse B lymphoma cell line, were used as antigen presenting cells in this study.

Plasmid Constructs. The original retroviral miRNA expression construct was modified to incorporate a truncated H-2K$_b$ surface marker and a blasticidin drug resistance gene to allow for magnetic bead assisted sorting and drug selection. These marker genes are driven by the PGK promoter and transcribed as a bicistronic message, with the truncated H2K$_b$ gene placed after the PGK promoter and the blasticidin resistance gene after the EMCV IRES (internal ribosomal entry site). miRNA gene expression is driven by the human H1 pol III promoter. The truncated H-2K$_b$ selection marker is non-functional since it is devoid of a cytoplasmic domain and is of a different MHC haplotype than the T cells in 5C.C7 transgenic mice (H-2Kk). miR-181a$^{mut}$ was generated by altering the 5' second and third nucleotides of the mature miR-181a (from (SEQ ID NO:36) 5'AACAUUCAACGCUGUCGGUGAGU3' to (SEQ ID NO:37) 5'A$\underline{UA}$AUUCAACGCUGUCGGU GAGU3', nucleotide changes are underlined).

Compensatory mutations were introduced to the miR-181a* strand to preserve the secondary structure of pre-miR181a. Mutant miR-181a can be properly expressed and processed as indicated by Northern blot analyses.

The basic firefly luciferase and lin-41 3'UTR fusion were cloned into a MSCV (murine stem cell virus) retroviral vector (FIG. 11B). Putative miR-181a target sequences were PCR amplified from a mouse cDNA library and subcloned to replace the lin-41 3'UTR in the basic reporter construct. Target regions amplified and corresponding PCR primers are listed:

| SEQ ID | | |
|---|---|---|
| | (1) SHP-2-t1 | (NM_011202.2: 5312 to 5533, 3' UTR) |
| 38 | Sense: | 5' AGAGTCACTCGAGTTAATACACTTTAGTGTCAAGA 3' |
| 39 | Antisense: | 5' ATACATCACGCGTCAAGAAAATGATTTTATTCTA 3' |
| | (2) DUSP6-t1 | (NM_026268.1: 2511 to 2748, 3' UTR) |
| 40 | Sense: | 5' AGAGTCACTCGAGTAACTTCAGCTGTGCTAAACA 3' |
| 41 | Antisense: | 5' ATACATCACGCGTTAATAAATTCCAGCTCAA AAC 3' |
| | (3) DUSP5-t1 | (XM_140740: 572 to 979, ORF) |

-continued

```
SEQ ID
  42  Sense:     5' AGAGTCACTCGAGACTGGCAGAAGCTGCGGGAGGA 3'
  43  Antisense: 5' ATACATCACGCGTCCACGGGGATCCACTTGTAGT 3'

(4) DUSP5-t2 (XM_140740: 2141 to 2485, 3' UTR)
  44  Sense:     5' AGAGTCACTCGAGCATGGTATCTCTCTAAAGCAC3'
  45  Antisense: 5' ATACATCACGCGTAAAACAAACCAACCAAGCAAC 3'.

(5) PTPN22-t-1 (NM_008979.1: 266 to 561, ORF)
  46  Sense:     5' AGAGTCACTCGAGCCCAAGAATATCAAGAAAAACAGATACAAGG 3',
  47  Antisense: 5' ATACATCACGCGT TGCGTTTCTCCTGGTTCGGCCCA 3';

(6) PTPN22-t-2 (NM_008979.1: 932 to 1618, ORF)
  48  Sense:     5' AGAGTCACTCGAGCAAACTCAGGAACAGTACGAAC 3',
  49  Antisense: 5' ATACATCACGCGT ATTCAGCTCTTCTGAAGAAACA 3'
```

To selectively restore miR-181a target expression in the miR-181a T cell blasts, a construct that simultaneously expresses miR-181a and the DUSP6, DUSP5 or SHP-2 coding regions were constructed (FIG. 26C). The mouse DUSP6, DUSP5 and SHP-2 coding regions were PCR amplified from a cDNA library generated from day 6 5C.C7 T cell blasts and cloned into the miR-181a expression vector (FIG. 26C) to replace the H-$2K_b$ gene.

Antibodies and Fluorescent Reagents. α-mouse PTPN22 polyclonal antibody was a kind gift from Dr. A. Chan and Dr. K. Hasegawa (Genentech). PE-streptavidin, PECy5-streptavidin, biotin-α-CD3ε, biotin-α-CD28, biotin-α-H-$2K_b$, biotin-α-IL-2, α-CD16/32, α-B7.1, α-B7.2, α-IL-2, FITC-α-CD4, PE-α-CTLA4, α-Lck PY505, PE-α-phospho-ERK1/2 and their isotype controls were from BD Pharmingen. Biotin-syrian hamster IgG control and FITC-conjugated Donkey anti-Rabbit IgG were from Jackson ImmunoResearch. Streptavidin was from Prozyme. For cross-linking experiments, azide was dialyzed away before use. α-Lck (3A5, for immunoprecipitation), α-SHP-2 (polyclonal) and α-phosphoserine (polyclonal) were from Upstate/Chemicon. (-DUSP6 (polyclonal), α-actin and α-Lck (polyclonal for immunoblotting) were from Santa Cruz Biotech. α-PY416 of Src family (PY394 of Lck) and anti-ppERK (T202/Y204) rabbit monoclonal antibody (197G2) were from Cell Signaling Technology. α-DUSP5 was from ABcam. α-SHP-1 (polyclonal) was from R&D Systems. The calcium indicator Fura-2-AM was purchased from Molecular Probes.

Quantitative RT-PCR for miRNA Expression Analysis. The ABI TaqMan miRNA assay was used to measure miR-181a expression in various T cell populations. Purified T cells were spiked with a synthetic miRNA standard at a fixed ratio of pmol per cell. Total RNA samples were then prepared using Trizol reagents. MiRNA expression in each cell population was determined using standard curve methods following the ABI TaqMan miRNA quantitative PCR protocol. Quantitative PCR for targets expression analysis. A two step qPCR approach was taken to quantify the mRNA level of various genes in this study. Total RNA were extracted from control or miR-181a virus infected day6 T cell blasts with PureLink™ RNA extraction kit (Invitrogen) and the first strand cDNA synthesis was performed with Superscript III system (Invitrogen). Using these single strand cDNA as template, quantitative PCR assays were performed with Platinum SYBR Green qPCR Supermix-UDG (Invitrogen) on an iQ5 qPCR machine (Bio-Rad). For each experiment, β-actin was used to normalize the amount of cDNA input. The PCR primers are: 1) for PTPN22, sense primer: 5' GCAGTGGGACATCTGAAATGAAGAGC 3', antisense primer: 5' CGGCTTGGGCCTGTATACAGTCCT 3'; 2) for SHP-2, sense primer: 5' GTTAAGCAAGCTG-GCTGAGCCAC 3', antisense prime: 5' CTGGAGTA-GAGCTTGTCCGACCTTA 3'; 3) for SHP-1, sense primer: 5' CAGGGACGTGACAGTAACATCCC 3', antisense primer: 5' CAGGTCCCCATTGTCTAGTGGG3'; 4) for DUSP5, sense primer: 5' GCCCGCGGGTCTACTTCCT-TAAA 3', antisense primer: 5' ATTTCAACCGGGCCAC-CCTGG 3'; 5) for DUSP6, sense primer: 5' TCCCTGAG-GCCATTTCTTTCATAGATG 3', antisense primer: 5'GCAGCTGGCCCATGAAGTTGAAGT 3' 6) for β-actin, sense primer: 5' TCTAGACTTCGAGCAGGAGATG 3', antisense primer: 5'CTAGGAGCCAGAGCAGTAATCT 3'.

Multi-channel Time-Lapse Microscopy. Calcium imaging and synaptic peptide quantification were performed on a Zeiss Axiovert-100TV station equipped with a CoolSNAP$_{HQ}$ CCD camera (Roper Scientific). Calcium dye Fura-2-AM (5 μg/ml) was loaded into day 6 5C.C7 T cells at room temperature for 30 minutes. Imaging experiments were performed on a humidified stage at 37° C. and 5% $CO_2$. The recording was controlled by MetaMorph software (Universal Imaging Corp). Signals from Fura-2 (ex 340 nm and 380 nm, em 510 nm/80 nm) were collected at 10 or 15 second intervals for up to 15 minutes and PE labelled peptides were imaged (ex 555 nm/28 nm, em 617 nm/73 nm) at variable time points. For each field, 21 stacks of PE images were taken at 1 ⌠m increments and the 3D images were reconstructed to measure the integrated fluorescence intensity. Image analysis was performed using MetaMorph Software Suite. The data points were pooled from four batches of primary cell preparation. For calcium dynamics and concentration integration analysis, in activated T cells, time zero was defined as the time point prior to the first 20% increase of ratioed fluorescent intensity, then the basal line (value=1.00) was drawn by averaging the intensity before time zero. In inactive T cells, time zero was arbitrarily assigned as the T:APC contact point observed in the DIC channel. The integrated value of cytosolic calcium elevation was generated by summing up the changes in relative calcium concentration at each time point within the first 5 minutes of T cell calcium response.

Phospho-Flow Analysis. Phospho-Flow technology was used to monitor T202 Y204 phosphorylation in ERK1/2 (ppERK). Briefly, T cell blasts infected with miR-181a expressing virus (GFP positive) were stimulated with APCs loaded with either antigenic peptides or with anti-CD3ε cross-linking, and fixed with 2% paraformaldehyde at room temperature for 20 minutes. After washes with ice-cold FACS buffer (PBS pH 7.4, 2 mM EDTA, 2% FBS), T cell blasts were blocked with anti-CD16/CD32 (10 μg/ml) for 15 minutes on ice and stained with fluorescent antibodies against the cell surface markers CD4, CD28, etc. After being washed three times with FACS buffer, T cell blasts were suspended in 90% ice-cold methanol and kept on ice for 30 minutes to allow for permeabilization. One million permeabilized cells were further blocked by anti-CD16/CD32 and species-matched serum, stained with phosphor specific ERK antibody, and analyzed by FACS (Cytomics FC500, Beckman Coulter). FACS data was analyzed with FlowJo software (Tree Star, Inc). The ppERK staining results were repeated with an indirect staining approach as reported by Altan-Bonnet et al (Altan-Bonnet and Germain, 2005). In this method, T cell blasts were stained with anti ppERK rabbit monoclonal antibody (Cell Signaling Technology), then followed by donkey Cy5-anti-rabbit IgG staining (Jackson ImmunoResearch) and FACS analysis.

Luciferase reporter assay for target validation. NIH-3T3 cells stably expressing miR-181a and miR-181a mut were generated by viral transduction and multiple rounds of blasticidin selection and then transfected with 0.1 μg of firefly luciferase reporter vector together with 0.025 μg of control Renilla luciferase control vectorusing FuGene 6 reagents (Roche). Cells were lysed at 48 or 72 hours after transfection and analyzed for firefly and Renilla luciferase activities using the Dual-Luciferase Assays (Promega) on a Veritas™ Microplate Luminometer.

Fetal Thymic Organ Culture. Thymi were dissected from day 15 embryos of 5C.C7 αβ TCR mice or day 17 embryos of 5C.C7 αβ TCR li$^{-/-}$ mice. Fetal thymi were cultured on 0.8 micron filters (Millipore) and MF support pads (Millipore) floated on RPMI culture medium. Antagomirs were added to thymi at a final concentration of 50 μg/ml on day 0 of culture, antigenic peptides were added on day 1, and single cell suspensions were prepared for FACS analysis on day 3-5.

Antagomir and Treatment. Antagomirs were synthesized as described (Krutzfeldt et al., 2005). The sequences are as shown in Example 3. All nucleotides used in synthesis are 2'-OMe-modified. Subscript 's' represents a phosphorothioate linkage; "Cy3" indicates Cy3 dye label at the 5' end of the oligo; "Chol" represents cholesterol linked through a hydroxyprolinol linkage. For naïve T cell transfection, cells were cultured for 16 hours in the presence of 5 ng/ml IL-7 and 50 μg/ml Ant181 or Mm Ant181; for DP thymocyte transfection, cells were cultured in RPMI medium for 12 hours in the presence of various amount of antagomir.

Example 3

Synthesis of Antagomirs

The single-stranded RNAs and modified RNA analogues (anatgomirs) were synthesized using U, $C^{Bz}$, $A^{BZ}$ and $G^{iBu}$ with 2'-O-methyl sugar monomers using β-cyanoethyl phosphoramidite chemistry and standard oligonucleotide synthesis protocols unless otherwise specified (Ref: Damha, M. J. & Ogilvie, K. K. Oligoribonucleotide synthesis. The silyl-phosphoramidite method. *Methods Mol. Biol.* 20, 81-114 (1993). The modifications used in this study are listed in Table 1. Quasar-570 (Q570, Cy3) and Quasar-570 (Q670, Cy5) phosphoramidite from Biosearch Technologies was coupled to the 5'-terminal under standards solid phase phosphoramidite synthesis conditions to obtain fluorophore tagged antagomirs, 2, 6-10 and mm-antagomirs 11-14 shown in Table 1 and FIG. 19. Extended 15 min coupling of quasar-570 phosphoramidite at a concentration of 0.1M in $CH_3CN$ in the presence of 5-(ethylthio)-1H-tetrazole activator followed by standard capping, oxidation and deprotection afforded labeled oligonucleotides. The Q570 conjugated sequences were HPLC purified on an in-house packed RPC-Source15 reverse-phase column. The buffers were 20 mM NaOAc in 10% $CH_3CN$ (buffer A) and 20 mM NaOAc in 70% $CH_3CN$ (buffer B). Fractions containing full-length oligonucleotides were pooled together and desalted. Integrity of the compounds were established by analytical HPLC, CGE and ES LC-MS. For duplex generation, equal molar mounts of miR-122 and antagomir were heated in 1×PBS at 95° C. for 5 min and slowly cooled to room temperature.

TABLE 1

Antagomirs and mm-antagomirs for various miRNA targets

| Antagomir/mm-Antagomir | SEQUENCE | TARGET |
| --- | --- | --- |
| 1 | oAsoCsoUoCoAoCoCoGoAoCoAoGoCo GoUoUoGoAoAoUsoGsoUsoUs-Chol | miR-181a |
| 2 | Cy3-oAsoCsoUoCoAoCoCoGoAoCoAoG oCoGoUoUoGoAoAoUsoGsoUsoUs-Chol | miR-181a |
| 3 | oCsoCsoCoCoUoAoUoCoAoCoAoA oUoUoAoGoCoAoUsoUsoAsoAs-Chol | miR-155 |
| 4 | oGsoUsoAoGoUoGoCoUoUoUoCoU oAoCoUoUoUsoAsoUsoGs-Chol | miR-142-5p |
| 5 | oCsoCsoAoUoAoAoAoGoUoAoGo GoAoAoAoCoAoCoUsoAsoCsoAs-Chol | miR-142-3p |
| 6 | Cy5-soAsoCoUoCoAoCoCoGoAoCoAoG oCoGoUoUoGoAoAoUsoGsoUsoUs-Chol | miR-181a |
| 7 | Cy5-soAsoCoUoCoAoCoCoGoAoCoAoG oGoUoUoGoAoAoUsoGsoUsoUs-Chol | miR-181c |
| 8 | Cy5-soCsoCoCoCoUoAoUoCoAoCoAoAo AoUoUoAoGoCoAoUsoUsoAsoAs-Chol | miR-155 |
| 9 | Cy5-soGsoUoAoGoUoGoCoUoUoUoCo UoAoCoUoUoUsoAsoUsoGs-Chol | miR-142-5p |
| 10 | Cy5-soCsoCoAoUoAoAoAoGoUoAoGo GoAoAoAoCoAoCoUsoAsoCsoAs-Chol | miR-142-3p |
| 11 | Cy3-soAsoCoUoCoAoCoCoGoAoCoAoG oCoGoUoUoUoUoAsoUsoAsoUs-Chol | MM-mirR-181a |
| 12 | Cy3-soAsoCoUoCoAoCoCoGoAoCoAoG oGoUoUoGoAoAoUsoGsoUsoUs-Chol | MM-miR-181c |
| 13 | Cy3s-oAsoCoAoAoCoAoCoAoCoCoAoUoU oGoUoCoAoCoAoCoUsoCsoCsoAs-Chol | miR-122 |
| 14 | Cy3s-oAsoCoAoCoAoCoAoAoCoAoCoU oGoUoCoAoCoAoUoUsoCsoCsoAs-Chol | MM-miRr-122 |

Note:
Modifications are as follow:
A) oN = 2'-O-methyl
B) s = PS linkage
C) Cy3 = Quasar 570 dye
D) Cy5 = Quasar 670 dye The compositions and procedures provided in the description can be effectively modified by those skilled in the art without departing from the spirit of the invention embodied in the claims that follow.

This application specifically incorporates by reference U.S. Provisional Application Ser. No. 60/854,407, filed Oct. 24, 2006, U.S. Provisional Application Ser. No. 60/873,764, filed Dec. 8, 2006, and U.S. Provisional Application Ser. No. 60/901,177, filed Feb. 12, 2007.

What is claimed is:

1. A method of decreasing T cell activity to an autoantigen, the method comprising:
reducing the activity of miR-181a in peripheral T cells of an individual with a T cell mediated autoimmune disease by administering a modified oligonucleotide that is complementary to miR-181a, wherein the oligonucleotide is at least 12 but not more than 25 nucleotides in length and has no more than 2 mismatches over its length compared to an equal length portion of miR-181a; and
thereby raising T cell receptor signaling threshold and decreasing T cell sensitivity to antigen.

2. The method of claim 1, wherein said modified oligonucleotide comprises a cholesterol conjugate.

3. The method of claim 1, wherein said modified oligonucleotide comprises one or more phosphorothioate linkages.

4. The method of claim 1, wherein said modified oligonucleotide comprises one or more sugar modifications.

5. The method of claim 1, wherein said modified oligonucleotide has no more than 1 mismatch over its length compared to an equal length portion of miR-181a.

6. The method of claim 1, wherein said modified oligonucleotide is fully complementary over its length compared to an equal length portion of mi R-181a.

7. The method of claim 1, wherein said modified oligonucleotide is at least 20 but not more than 25 nucleotides in length.

8. The method of claim 1, wherein the contacting is performed ex vivo.

* * * * *

SEQUENCE LISTING

<160> NUMBER OF SEQ ID NOS: 70

<210> SEQ ID NO 1
<211> LENGTH: 60
<212> TYPE: RNA
<213> ORGANISM: Mus musculus

<400> SEQUENCE: 1
aacauucaac gcugucggug aguuuggaau ucaaauaaaa accaucgacc guugauugua    60

<210> SEQ ID NO 2
<211> LENGTH: 60
<212> TYPE: RNA
<213> ORGANISM: Mus musculus

<400> SEQUENCE: 2
auaauucaac gcugucggug aguuuggaau ucaaauaaaa accaucgacc guugauuuaa    60

<210> SEQ ID NO 3
<211> LENGTH: 25
<212> TYPE: RNA
<213> ORGANISM: Mus musculus

<400> SEQUENCE: 3
ucaaugccag cuuuauuaag ggugu                                          25

<210> SEQ ID NO 4
<211> LENGTH: 24
<212> TYPE: RNA
<213> ORGANISM: Mus musculus

<400> SEQUENCE: 4
acucuccugg acuucuggag gaug                                           24

<210> SEQ ID NO 5
<211> LENGTH: 21
<212> TYPE: RNA
<213> ORGANISM: Mus musculus

<400> SEQUENCE: 5
acuggucuac agugcugugu u                                              21

<210> SEQ ID NO 6
<211> LENGTH: 25
<212> TYPE: RNA
<213> ORGANISM: Mus musculus

<400> SEQUENCE: 6
gcuguuuaag aggcacaugg auguu                                          25

<210> SEQ ID NO 7
<211> LENGTH: 28
<212> TYPE: RNA
<213> ORGANISM: Mus musculus

<400> SEQUENCE: 7
auuuaccaaa aaacgccaug agggaugu                                       28

<210> SEQ ID NO 8
<211> LENGTH: 27
<212> TYPE: RNA
<213> ORGANISM: Mus musculus

<400> SEQUENCE: 8

```
uuggccuuag gacuucuacg augaaug                                                27

<210> SEQ ID NO 9
<211> LENGTH: 23
<212> TYPE: RNA
<213> ORGANISM: Mus musculus

<400> SEQUENCE: 9
uuccccagcu gugccaugag ugu                                                    23

<210> SEQ ID NO 10
<211> LENGTH: 24
<212> TYPE: RNA
<213> ORGANISM: Mus musculus

<400> SEQUENCE: 10
acgaaacugg aagugugugu augu                                                   24

<210> SEQ ID NO 11
<211> LENGTH: 31
<212> TYPE: RNA
<213> ORGANISM: Mus musculus

<400> SEQUENCE: 11
uuaccucugu acaaaauucu ucagggagug u                                           31

<210> SEQ ID NO 12
<211> LENGTH: 17
<212> TYPE: RNA
<213> ORGANISM: Mus musculus

<400> SEQUENCE: 12
cgcccauuug guggaug                                                           17

<210> SEQ ID NO 13
<211> LENGTH: 31
<212> TYPE: RNA
<213> ORGANISM: Mus musculus

<400> SEQUENCE: 13
acucacagua uccugagugc uguguggaug u                                           31

<210> SEQ ID NO 14
<211> LENGTH: 25
<212> TYPE: RNA
<213> ORGANISM: Mus musculus

<400> SEQUENCE: 14
gcacaucaca gcccugcuga auguu                                                  25

<210> SEQ ID NO 15
<211> LENGTH: 23
<212> TYPE: RNA
<213> ORGANISM: Mus musculus

<400> SEQUENCE: 15
uucccguaaa cccaugugaa ugu                                                    23

<210> SEQ ID NO 16
<211> LENGTH: 22
<212> TYPE: DNA
<213> ORGANISM: Bos Taurus
```

```
<400> SEQUENCE: 16
aacattcaac gctgtcggtg ag                                              22

<210> SEQ ID NO 17
<211> LENGTH: 22
<212> TYPE: RNA
<213> ORGANISM: Bos Taurus

<400> SEQUENCE: 17
aacauucaac gcugucggug ag                                              22

<210> SEQ ID NO 18
<211> LENGTH: 22
<212> TYPE: DNA
<213> ORGANISM: Macaca nemestrina

<400> SEQUENCE: 18
aacattcaac gctgtcggtg ag                                              22

<210> SEQ ID NO 19
<211> LENGTH: 22
<212> TYPE: RNA
<213> ORGANISM: Macaca nemestrina

<400> SEQUENCE: 19
aacauucaac gcugucggug ag                                              22

<210> SEQ ID NO 20
<211> LENGTH: 22
<212> TYPE: DNA
<213> ORGANISM: Saguinus labiatus
<220> FEATURE:
<223> OTHER INFORMATION: NCBI Taxonomy ID 78454; common name red-chested
      mustached tamarin

<400> SEQUENCE: 20
aacattcaac gctgtcggtg ag                                              22

<210> SEQ ID NO 21
<211> LENGTH: 22
<212> TYPE: RNA
<213> ORGANISM: Saguinus labiatus
<220> FEATURE:
<223> OTHER INFORMATION: NCBI Taxonomy ID 78454; common name red-chested
      mustached tamarin

<400> SEQUENCE: 21
aacauucaac gcugucggug ag                                              22

<210> SEQ ID NO 22
<211> LENGTH: 22
<212> TYPE: DNA
<213> ORGANISM: Macaca mulatta

<400> SEQUENCE: 22
aacattcaac gctgtcggtg ag                                              22

<210> SEQ ID NO 23
<211> LENGTH: 22
<212> TYPE: RNA
<213> ORGANISM: Macaca mulatta

<400> SEQUENCE: 23
aacauucaac gcugucggug ag                                              22
```

<210> SEQ ID NO 24
<211> LENGTH: 22
<212> TYPE: DNA
<213> ORGANISM: Pan troglodytes

<400> SEQUENCE: 24
aacattcaac gctgtcggtg ag                                              22

<210> SEQ ID NO 25
<211> LENGTH: 22
<212> TYPE: RNA
<213> ORGANISM: Pan troglodytes

<400> SEQUENCE: 25
aacauucaac gcugucggug ag                                              22

<210> SEQ ID NO 26
<211> LENGTH: 22
<212> TYPE: DNA
<213> ORGANISM: Pan paniscus

<400> SEQUENCE: 26
aacattcaac gctgtcggtg ag                                              22

<210> SEQ ID NO 27
<211> LENGTH: 22
<212> TYPE: RNA
<213> ORGANISM: Pan paniscus

<400> SEQUENCE: 27
aacauucaac gcugucggug ag                                              22

<210> SEQ ID NO 28
<211> LENGTH: 22
<212> TYPE: DNA
<213> ORGANISM: Gorilla gorilla

<400> SEQUENCE: 28
aacattcaac gctgtcggtg ag                                              22

<210> SEQ ID NO 29
<211> LENGTH: 22
<212> TYPE: RNA
<213> ORGANISM: Gorilla gorilla

<400> SEQUENCE: 29
aacauucaac gcugucggug ag                                              22

<210> SEQ ID NO 30
<211> LENGTH: 23
<212> TYPE: DNA
<213> ORGANISM: Homo sapiens

<400> SEQUENCE: 30
aacattcaac gctgtcggtg agt                                             23

<210> SEQ ID NO 31
<211> LENGTH: 23
<212> TYPE: RNA
<213> ORGANISM: Homo sapiens

<400> SEQUENCE: 31

-continued aacauucaac gcugucggug agu                                          23

<210> SEQ ID NO 32
<211> LENGTH: 23
<212> TYPE: DNA
<213> ORGANISM: Mus musculus

<400> SEQUENCE: 32
aacattcaac gctgtcggtg agt                                          23

<210> SEQ ID NO 33
<211> LENGTH: 23
<212> TYPE: RNA
<213> ORGANISM: Mus musculus

<400> SEQUENCE: 33
aacauucaac gcugucggug agu                                          23

<210> SEQ ID NO 34
<211> LENGTH: 16
<212> TYPE: PRT
<213> ORGANISM: Mus musculus

<400> SEQUENCE: 34

Ala Asn Glu Arg Ala Asp Leu Ile Ala Tyr Leu Lys Gln Ala Gly Lys
 1               5                  10                  15

<210> SEQ ID NO 35
<211> LENGTH: 16
<212> TYPE: PRT
<213> ORGANISM: Mus musculus

<400> SEQUENCE: 35

Ala Asn Glu Arg Ala Asp Leu Ile Ala Tyr Leu Ala Gln Ala Thr Lys
 1               5                  10                  15

<210> SEQ ID NO 36
<211> LENGTH: 23
<212> TYPE: RNA
<213> ORGANISM: Mus musculus

<400> SEQUENCE: 36
aacauucaac gcugucggug agu                                          23

<210> SEQ ID NO 37
<211> LENGTH: 23
<212> TYPE: RNA
<213> ORGANISM: Mus musculus

<400> SEQUENCE: 37
auaauucaac gcugucggug agu                                          23

<210> SEQ ID NO 38
<211> LENGTH: 35
<212> TYPE: DNA
<213> ORGANISM: Artificial Sequence
<220> FEATURE:
<223> OTHER INFORMATION: Synthetic nucleotide

<400> SEQUENCE: 38
agagtcactc gagttaatac actttagtgt caaga                              35

<210> SEQ ID NO 39
<211> LENGTH: 34

<210> SEQ ID NO 39
<211> LENGTH: 34
<212> TYPE: DNA
<213> ORGANISM: Artificial Sequence
<220> FEATURE:
<223> OTHER INFORMATION: Synthetic nucleotide

<400> SEQUENCE: 39
atacatcacg cgtcaagaaa atgattttat tcta            34

<210> SEQ ID NO 40
<211> LENGTH: 34
<212> TYPE: DNA
<213> ORGANISM: Artificial Sequence
<220> FEATURE:
<223> OTHER INFORMATION: Synthetic nucleotide

<400> SEQUENCE: 40
agagtcactc gagtaacttc agctgtgcta aaca            34

<210> SEQ ID NO 41
<211> LENGTH: 34
<212> TYPE: DNA
<213> ORGANISM: Artificial Sequence
<220> FEATURE:
<223> OTHER INFORMATION: Synthetic nucleotide

<400> SEQUENCE: 41
atacatcacg cgttaataaa ttccagctca aaac            34

<210> SEQ ID NO 42
<211> LENGTH: 35
<212> TYPE: DNA
<213> ORGANISM: Artificial Sequence
<220> FEATURE:
<223> OTHER INFORMATION: Synthetic nucleotide

<400> SEQUENCE: 42
agagtcactc gagactggca gaagctgcgg gagga           35

<210> SEQ ID NO 43
<211> LENGTH: 34
<212> TYPE: DNA
<213> ORGANISM: Artificial Sequence
<220> FEATURE:
<223> OTHER INFORMATION: Synthetic nucleotide

<400> SEQUENCE: 43
atacatcacg cgtccacggg gatccacttg tagt            34

<210> SEQ ID NO 44
<211> LENGTH: 34
<212> TYPE: DNA
<213> ORGANISM: Artificial Sequence
<220> FEATURE:
<223> OTHER INFORMATION: Synthetic nucleotide

<400> SEQUENCE: 44
agagtcactc gagcatggta tctctctaaa gcac            34

<210> SEQ ID NO 45
<211> LENGTH: 34
<212> TYPE: DNA
<213> ORGANISM: Artificial Sequence
<220> FEATURE:
<223> OTHER INFORMATION: Synthetic nucleotide

<400> SEQUENCE: 45

```
atacatcacg cgtaaaacaa accaaccaag caac                           34

<210> SEQ ID NO 46
<211> LENGTH: 44
<212> TYPE: DNA
<213> ORGANISM: Artificial Sequence
<220> FEATURE:
<223> OTHER INFORMATION: Synthetic nucleotide

<400> SEQUENCE: 46
agagtcactc gagcccaaga atatcaagaa aaacagatac aagg                44

<210> SEQ ID NO 47
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 47
atacatcacg cgttgcgttt ctcctggttc ggccca                         36

<210> SEQ ID NO 48
<211> LENGTH: 35
<212> TYPE: DNA
<213> ORGANISM: Artificial Sequence
<220> FEATURE:
<223> OTHER INFORMATION: Synthetic nucleotide

<400> SEQUENCE: 48
agagtcactc gagcaaactc aggaacagta cgaac                          35

<210> SEQ ID NO 49
<211> LENGTH: 35
<212> TYPE: DNA
<213> ORGANISM: Artificial Sequence
<220> FEATURE:
<223> OTHER INFORMATION: Synthetic nucleotide

<400> SEQUENCE: 49
atacatcacg cgtattcagc tcttctgaag aaaca                          35

<210> SEQ ID NO 50
<211> LENGTH: 23
<212> TYPE: RNA
<213> ORGANISM: Artificial Sequence
<220> FEATURE:
<223> OTHER INFORMATION: Synthetic nucleotide

<400> SEQUENCE: 50
acucaccgac agcguugaau guu                                       23

<210> SEQ ID NO 51
<211> LENGTH: 22
<212> TYPE: RNA
<213> ORGANISM: Artificial Sequence
<220> FEATURE:
<223> OTHER INFORMATION: Synthetic nucleotide

<400> SEQUENCE: 51
ccccuaucac aauuagcauu aa                                        22

<210> SEQ ID NO 52
<211> LENGTH: 20
<212> TYPE: RNA
<213> ORGANISM: Artificial Sequence
```

```
<220> FEATURE:
<223> OTHER INFORMATION: Synthetic nucleotide

<400> SEQUENCE: 52
guagugcuuu cuacuuuaug                                              20

<210> SEQ ID NO 53
<211> LENGTH: 22
<212> TYPE: RNA
<213> ORGANISM: Artificial Sequence
<220> FEATURE:
<223> OTHER INFORMATION: Synthetic nucleotide

<400> SEQUENCE: 53
ccauaaagua ggaaacacua ca                                           22

<210> SEQ ID NO 54
<211> LENGTH: 22
<212> TYPE: RNA
<213> ORGANISM: Artificial Sequence
<220> FEATURE:
<223> OTHER INFORMATION: Synthetic nucleotide

<400> SEQUENCE: 54
acucaccgac agguugaaug uu                                           22

<210> SEQ ID NO 55
<211> LENGTH: 23
<212> TYPE: RNA
<213> ORGANISM: Artificial Sequence
<220> FEATURE:
<223> OTHER INFORMATION: Synthetic nucleotide

<400> SEQUENCE: 55
acucaccgac agcguuuuua uau                                          23

<210> SEQ ID NO 56
<211> LENGTH: 22
<212> TYPE: RNA
<213> ORGANISM: Artificial Sequence
<220> FEATURE:
<223> OTHER INFORMATION: Synthetic nucleotide

<400> SEQUENCE: 56
acucaccgac agguugaaug uu                                           22

<210> SEQ ID NO 57
<211> LENGTH: 23
<212> TYPE: RNA
<213> ORGANISM: Artificial Sequence
<220> FEATURE:
<223> OTHER INFORMATION: Synthetic nucleotide

<400> SEQUENCE: 57
acaaacacca uugucacacu cca                                          23

<210> SEQ ID NO 58
<211> LENGTH: 23
<212> TYPE: RNA
<213> ORGANISM: Artificial Sequence
<220> FEATURE:
<223> OTHER INFORMATION: Synthetic nucleotide

<400> SEQUENCE: 58
acacacaaca cugucacauu cca                                          23
```

<210> SEQ ID NO 59
<211> LENGTH: 26
<212> TYPE: DNA
<213> ORGANISM: Artificial Sequence
<220> FEATURE:
<223> OTHER INFORMATION: Synthetic nucleotide

<400> SEQUENCE: 59
gcagtgggac atctgaaatg aagagc                                              26

<210> SEQ ID NO 60
<211> LENGTH: 24
<212> TYPE: DNA
<213> ORGANISM: Artificial Sequence
<220> FEATURE:
<223> OTHER INFORMATION: Synthetic nucleotide

<400> SEQUENCE: 60
cggcttgggc ctgtatacag tcct                                                24

<210> SEQ ID NO 61
<211> LENGTH: 23
<212> TYPE: DNA
<213> ORGANISM: Artificial Sequence
<220> FEATURE:
<223> OTHER INFORMATION: Synthetic nucleotide

<400> SEQUENCE: 61
gttaagcaag ctggctgagc cac                                                 23

<210> SEQ ID NO 62
<211> LENGTH: 25
<212> TYPE: DNA
<213> ORGANISM: Artificial Sequence
<220> FEATURE:
<223> OTHER INFORMATION: Synthetic nucleotide

<400> SEQUENCE: 62
ctggagtaga gcttgtccga cctta                                               25

<210> SEQ ID NO 63
<211> LENGTH: 23
<212> TYPE: DNA
<213> ORGANISM: Artificial Sequence
<220> FEATURE:
<223> OTHER INFORMATION: Synthetic nucleotide

<400> SEQUENCE: 63
cagggacgtg acagtaacat ccc                                                 23

<210> SEQ ID NO 64
<211> LENGTH: 22
<212> TYPE: DNA
<213> ORGANISM: Artificial Sequence
<220> FEATURE:
<223> OTHER INFORMATION: Synthetic nucleotide

<400> SEQUENCE: 64
caggtcccca ttgtctagtg gg                                                  22

<210> SEQ ID NO 65
<211> LENGTH: 23
<212> TYPE: DNA
<213> ORGANISM: Artificial Sequence
<220> FEATURE:
<223> OTHER INFORMATION: Synthetic nucleotide

```
<400> SEQUENCE: 65
gcccgcgggt ctacttcctt aaa                                              23

<210> SEQ ID NO 66
<211> LENGTH: 21
<212> TYPE: DNA
<213> ORGANISM: Artificial Sequence
<220> FEATURE:
<223> OTHER INFORMATION: Synthetic nucleotide

<400> SEQUENCE: 66
atttcaaccg ggccaccctg g                                                21

<210> SEQ ID NO 67
<211> LENGTH: 27
<212> TYPE: DNA
<213> ORGANISM: Artificial Sequence
<220> FEATURE:
<223> OTHER INFORMATION: Synthetic nucleotide

<400> SEQUENCE: 67
tccctgaggc catttctttc atagatg                                          27

<210> SEQ ID NO 68
<211> LENGTH: 24
<212> TYPE: DNA
<213> ORGANISM: Artificial Sequence
<220> FEATURE:
<223> OTHER INFORMATION: Synthetic nucleotide

<400> SEQUENCE: 68
gcagctggcc catgaagttg aagt                                             24

<210> SEQ ID NO 69
<211> LENGTH: 22
<212> TYPE: DNA
<213> ORGANISM: Artificial Sequence
<220> FEATURE:
<223> OTHER INFORMATION: Synthetic nucleotide

<400> SEQUENCE: 69
tctagacttc gagcaggaga tg                                               22

<210> SEQ ID NO 70
<211> LENGTH: 22
<212> TYPE: DNA
<213> ORGANISM: Artificial Sequence
<220> FEATURE:
<223> OTHER INFORMATION: Synthetic nucleotide

<400> SEQUENCE: 70
ctaggagcca gagcagtaat ct                                               22
```